(12) United States Patent
Alkhatib

(10) Patent No.: US 12,171,656 B2
(45) Date of Patent: Dec. 24, 2024

(54) RADIOPAQUE ELEMENTS ON PROSTHETIC HEART VALVES

(71) Applicant: St. Jude Medical, Cardiology Division, Inc., St. Paul, MN (US)

(72) Inventor: Yousef F. Alkhatib, Edina, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 182 days.

(21) Appl. No.: 17/727,056

(22) Filed: Apr. 22, 2022

(65) Prior Publication Data

US 2022/0338981 A1    Oct. 27, 2022

Related U.S. Application Data

(60) Provisional application No. 63/178,096, filed on Apr. 22, 2021.

(51) Int. Cl.
*A61F 2/24* (2006.01)

(52) U.S. Cl.
CPC .... *A61F 2/2418* (2013.01); *A61F 2220/0075* (2013.01); *A61F 2250/0098* (2013.01)

(58) Field of Classification Search
CPC ........... A61F 2/2418; A61F 2220/0075; A61F 2250/0098
See application file for complete search history.

(56) References Cited

U.S. PATENT DOCUMENTS

| | | | |
|---|---|---|---|
| 10,314,701 B2 | 6/2019 | Von Segesser | |
| 10,639,148 B2 | 5/2020 | Braido | |
| 2006/0020327 A1 | 1/2006 | Lashinski | |
| 2008/0275540 A1 | 11/2008 | Wen | |
| 2009/0171432 A1 | 7/2009 | Von Segesser | |
| 2010/0121436 A1 | 5/2010 | Tuval | |
| 2010/0172556 A1 | 7/2010 | Cohen | |
| 2010/0249908 A1 | 9/2010 | Chau | |
| 2010/0331972 A1 | 12/2010 | Pintor | |
| 2012/0078352 A1 | 3/2012 | Wang | |
| 2014/0243974 A1 | 8/2014 | Wood | |
| 2014/0296706 A1 | 10/2014 | Chronos | |
| 2019/0298968 A1 | 10/2019 | Morin | |
| 2021/0030535 A1 | 2/2021 | Liu | |
| 2022/0175521 A1* | 6/2022 | Baldwin | A61F 2/2418 |
| 2022/0175524 A1* | 6/2022 | Harewood | A61B 34/20 |

FOREIGN PATENT DOCUMENTS

WO    2007054015    5/2007

* cited by examiner

*Primary Examiner* — Suba Ganesan
(74) *Attorney, Agent, or Firm* — SLEMAN & LUND LLP

(57) ABSTRACT

A prosthetic heart valve for replacing a native valve includes a stent, a valve assembly, and a radiopaque element. The stent has a plurality of commissure attachment features. The valve assembly includes a plurality of leaflets and first and second cuffs. The first cuff has a proximal edge relatively close to the inflow end of the stent. The second cuff may be annularly disposed about the stent radially outward of the first cuff and radially outward of the stent. The proximal edge of the first cuff is coupled to the proximal edge of the second cuff substantially continuously along a circumference of the inflow end of the stent so that a pocket is formed between the first cuff and the second cuff. The radiopaque element is disposed within the pocket and aligned in a longitudinal direction of the stent with at least one of the plurality of commissure attachment features.

17 Claims, 59 Drawing Sheets

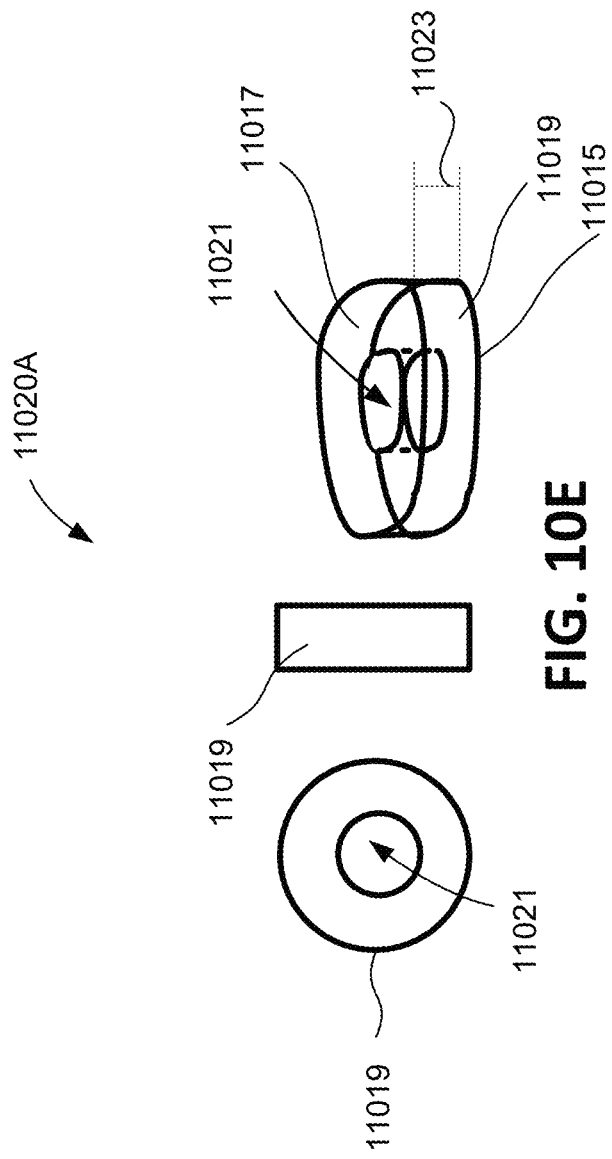

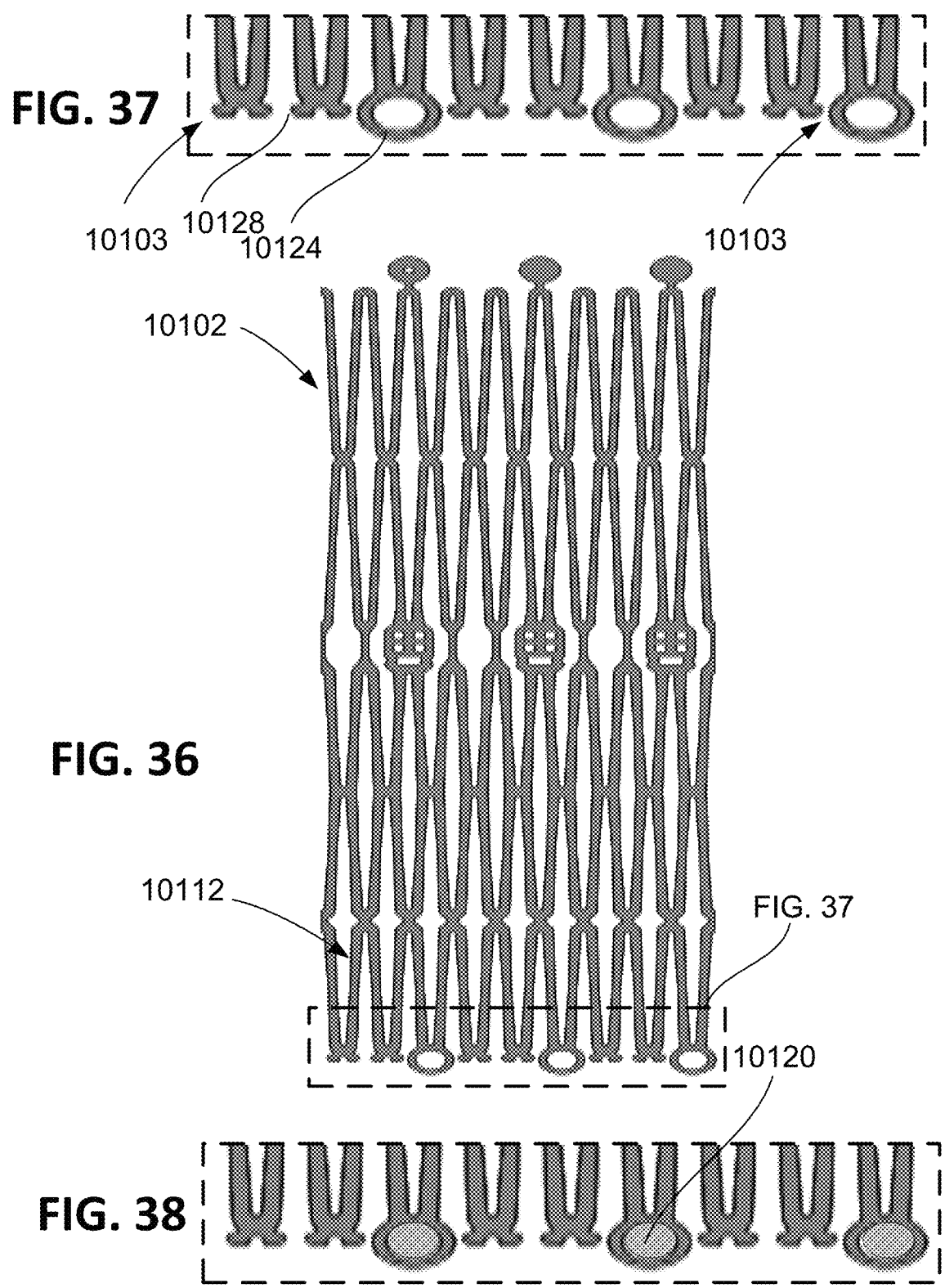

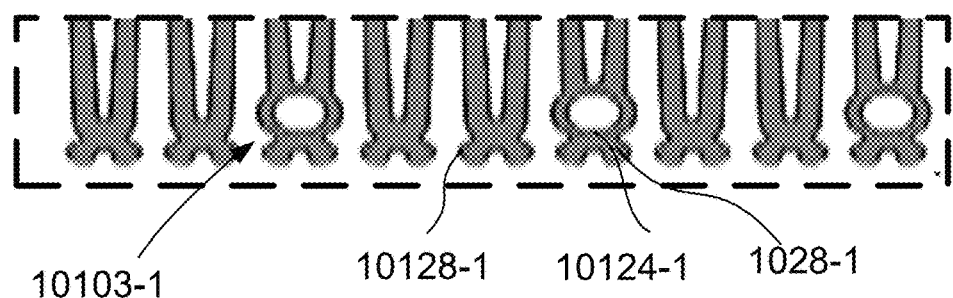
FIG. 40A
10103-1   10128-1   10124-1   1028-1
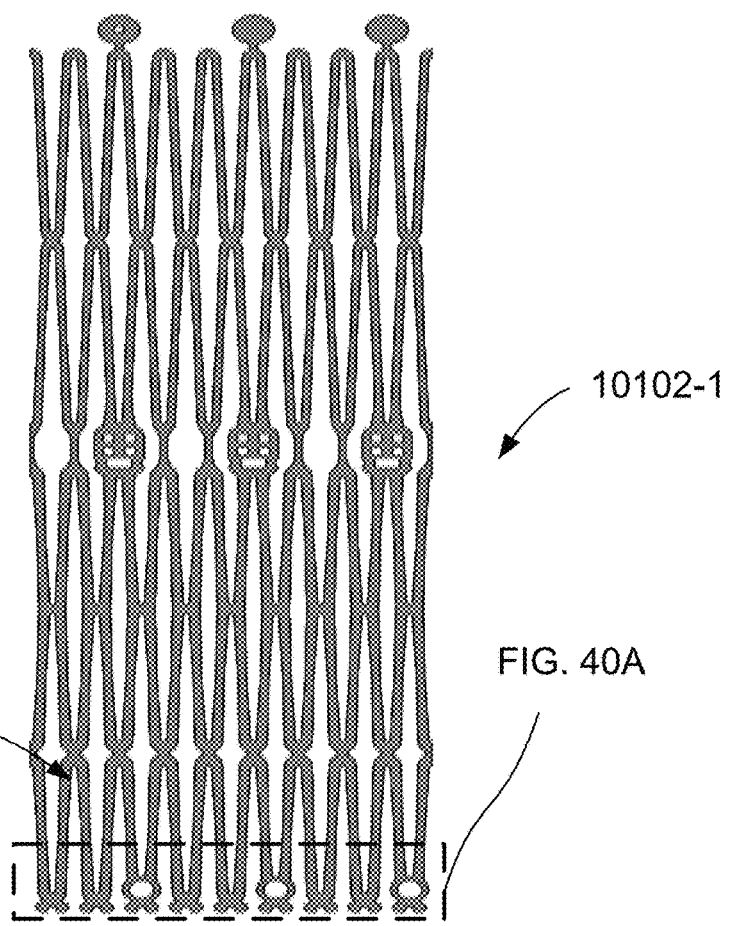
FIG. 39
10112-1
FIG. 40A
10102-1
10120-1
10124-1
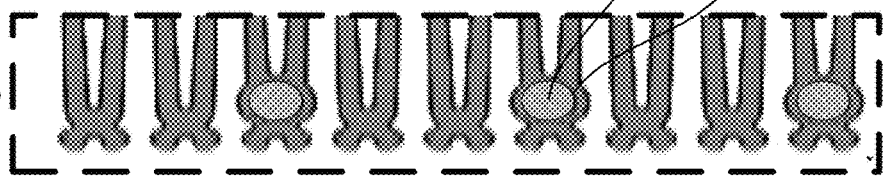
FIG. 40B

RADIOPAQUE ELEMENTS ON PROSTHETIC HEART VALVES

The present application claims the benefit of the filing date of U.S. Provisional Patent Application No. 63/178,096, filed Apr. 22, 2021, the disclosure of which is hereby incorporated herein by reference.

BACKGROUND OF THE DISCLOSURE

The present disclosure relates in general to a heart valve for heart valve replacement and, in particular, to prosthetic heart valves. More particularly, the present disclosure relates to methods and devices for facilitating prosthetic heart valve implantation procedures using radiopaque elements.

When a native heart valve in an individual is diseased or damaged, a prosthetic heart valve may be implanted in that individual to replace the native heart valve. Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are two common types of stents on which the valve structures are ordinarily mounted: a self-expanding stent and a balloon-expandable stent. To load such valves into a delivery apparatus and deliver them into a patient, the valve is first collapsed or crimped to reduce its circumferential size.

When a collapsed prosthetic valve has reached the desired implant site in the patient (e.g., at or near the annulus of the patient's heart valve that is to be replaced by the prosthetic valve), the prosthetic valve can be deployed or released from the delivery apparatus and re-expanded to full operating size. For balloon-expandable valves, this generally involves releasing the valve, assuring its proper location, and then expanding a balloon positioned within the valve stent. For self-expanding valves, on the other hand, the stent automatically expands as a sheath covering the valve is withdrawn.

Surgeons face many challenges when implanting a prosthetic heart valve. Accurate placement at the time of deployment, as well as the final position of the prosthetic heart valve, are paramount.

BRIEF SUMMARY

According to an aspect of the disclosure, a prosthetic heart valve for replacing a native valve includes a stent, a valve assembly, and a radiopaque element. The stent has an inflow end, an outflow end, a plurality of cells formed by cell struts, a plurality of commissure attachment features, and a collapsed condition and an expanded condition. The valve assembly may be disposed within the stent and further include a plurality of leaflets, a first cuff, and a second cuff. The first cuff may have a proximal edge relatively close to the inflow end of the stent and a distal edge relatively distant from the inflow end. The first cuff being may be annularly disposed adjacent the stent. The second cuff has a proximal edge relatively close to the inflow end of the stent and a distal edge relatively distant from the inflow end. The second cuff may be annularly disposed about the stent radially outward of the first cuff and radially outward of the stent, wherein the proximal edge of the first cuff is coupled to the proximal edge of the second cuff substantially continuously along a circumference of the inflow end of the stent so that a pocket is formed between the first cuff and the second cuff. The radiopaque element is disposed within the pocket and aligned in a longitudinal direction of the stent with at least one of the plurality of commissure attachment features.

According to another aspect of the disclosure, a prosthetic heart valve for replacing a native valve includes a stent, a valve assembly, and a plurality of radiopaque elements. The stent extends in a longitudinal direction of the stent between an inflow end and an outflow end. The stent has a plurality of cells formed by cell struts, a plurality of commissure attachment features, and a collapsed condition and an expanded condition. The valve assembly may be disposed within the stent and include a plurality of leaflets; and a cuff annularly disposed adjacent the stent. The plurality of radiopaque elements may be attached to the cuff, and each of the plurality of radiopaque elements may be aligned in a longitudinal direction of the stent with a corresponding one of the plurality of commissure attachment features. The inflow end of the stent includes a plurality of tips defining a plane, and edges of at least two of the plurality of radiopaque elements are positioned a same distance away from the plane.

According to another aspect of the disclosure, a prosthetic heart valve includes a stent, a valve assembly, and a plurality of radiopaque elements. The stent has an inflow end, an outflow end, a plurality of cells formed by cell struts, a plurality of commissure attachment features, and a collapsed condition and an expanded condition, wherein the inflow end of the stent includes a plurality of tips defining a plane. The valve assembly is disposed within the stent and includes a plurality of leaflets and first and second cuffs. The first cuff has a proximal edge relatively close to the inflow end of the stent and a distal edge relatively distant from the inflow end. The first cuff is annularly disposed adjacent the stent. The second cuff has a proximal edge relatively close to the inflow end of the stent and a distal edge relatively distant from the inflow end. The second cuff is annularly disposed about the stent radially outward of the first cuff and radially outward of the stent. The proximal edge of the first cuff is coupled to the proximal edge of the second cuff substantially continuously along a circumference of the inflow end of the stent so that a pocket is formed between the first cuff and the second cuff. The plurality of radiopaque elements are sutured to the first cuff and/or the second cuff and each of the plurality of radiopaque elements is aligned in a longitudinal direction of the stent with a corresponding one of the plurality of commissure attachment features. An edge of each of the plurality of radiopaque elements is circumferentially aligned with one another at a same distance away from the plane.

According to an aspect of the disclosure, a prosthetic heart valve for replacing a native valve includes a stent, a valve assembly disposed within the stent, and a radiopaque element. The stent has an inflow end, an outflow end, a plurality of cells formed by cell struts, a collapsed condition and an expanded condition. The valve assembly includes a plurality of leaflets, a first cuff, and a second cuff. The first cuff has a proximal edge facing toward the inflow end of the stent and a distal edge facing toward the outflow end of the stent. The first cuff is annularly disposed adjacent the stent. The second cuff has a proximal edge facing toward the inflow end of the stent and a distal edge facing toward the outflow end of the stent. The second cuff is annularly disposed about the stent radially outward of the first cuff and radially outward of the stent. A radiopaque element is disposed on the second cuff, such that the radiopaque element is moveable relative to the stent.

According to another aspect of the disclosure, a prosthetic heart valve for replacing a native valve includes a stent, a valve assembly disposed within the stent, and a plurality of radiopaque elements. The stent extends in a longitudinal direction between an inflow end and an outflow end. The stent includes a plurality of cells formed by cell struts and has a collapsed condition and an expanded condition. The valve assembly includes a plurality of leaflets and a cuff annularly disposed adjacent the stent. A plurality of radiopaque elements is attached to the cuff.

According to another aspect of the disclosure, a prosthetic heart valve for replacing a native valve includes a stent, a valve assembly disposed within the stent, a first cuff, a second cuff, a pocket formed between the first cuff and the second cuff, and a radiopaque element disposed within the pocket. The stent has an inflow end, an outflow end, a plurality of cells formed by cell struts, a collapsed condition, and an expanded condition. The valve assembly includes a plurality of leaflets, a first cuff and a second cuff. The first cuff has a proximal edge facing toward the inflow end of the stent and a distal edge facing toward the outflow end of the stent. The first cuff is annularly disposed adjacent the stent. The second cuff has a proximal edge facing toward the inflow end of the stent and a distal edge facing toward the outflow end of the stent. The second cuff is annularly disposed about the stent radially outward of the first cuff and radially outward of the stent. The proximal edge of the first cuff is coupled to the proximal edge of the second cuff substantially continuously along a circumference of the inflow end of the stent so that a pocket is formed between the first cuff and the second cuff. A radiopaque element is disposed within the pocket.

According to another aspect of the disclosure, a prosthetic heart valve for replacing a native valve includes a stent, a valve assembly disposed within the stent, and a plurality of radiopaque elements. The stent has an inflow end, an outflow end, a plurality of cells formed by cell struts, a collapsed condition, and an expanded condition. The valve assembly includes a plurality of leaflets; and a cuff annularly disposed adjacent the stent. The plurality of radiopaque elements is disposed on the cuff, at least one of the plurality of leaflets, the stent, or a combination of two or more of the foregoing.

According to another aspect of the disclosure, a prosthetic heart valve for replacing a native valve includes a stent, a valve assembly disposed within the stent, and a radiopaque element. The stent extends in a longitudinal direction between an inflow end and an outflow end. The stent includes a plurality of cells formed by cell struts and a plurality of commissure attachment features and has a collapsed condition and an expanded condition. The valve assembly includes a plurality of leaflets and a cuff that has a proximal edge facing toward the inflow end of the stent and a distal edge facing toward the outflow end of the stent. The cuff is annularly disposed adjacent the stent. The radiopaque element is positioned on the cuff in alignment with one of the plurality of commissure attachment features along an axis extending in the longitudinal direction through the one of the plurality of commissure attachment features.

BRIEF DESCRIPTION OF THE DRAWINGS

Various embodiments of the presently disclosed prosthetic heart valve may be more fully understood with reference to the following detailed description when read with the accompanying drawings, in which:

FIG. 10E are schematic views of an example radiopaque element according to an aspect of the disclosure;

FIG. 36 is a developed view of a collapsed stent with openings for receiving radiopaque elements according to an embodiment of the disclosure;

FIG. 37 is an enlarged view of an end portion of the stent of FIG. 36;

FIG. 38 is a view similar to FIG. 37 having radiopaque elements within the stent openings;

FIG. 39 is a developed view of a collapsed stent with openings for receiving radiopaque elements according to an embodiment of the disclosure;

FIG. 40A is an enlarged view of an end portion of the stent of FIG. 39;

FIG. 40B is a view similar to FIG. 40A having radiopaque elements within the stent openings;

Unless otherwise noted herein, each of the stents and prosthetic heart valves are shown in the figures in an expanded condition.

DETAILED DESCRIPTION

As used herein in connection with a prosthetic heart valve, the term "inflow end" refers to the end of the heart valve through which blood enters when the valve is functioning as intended, and the term "outflow end" refers to the end of the heart valve through which blood exits when the valve is functioning as intended. As used herein, the term "proximal" refers to the inflow end of a prosthetic heart valve or to elements of a prosthetic heart valve that are relatively close to the inflow end, and the term "distal" refers to the outflow end of a prosthetic heart valve or to elements of a prosthetic heart valve that are relatively close to the outflow end. As used herein, the terms "generally," "substantially," and "about" are intended to mean that slight deviations from absolute are included within the scope of the term so modified. Like numbers refer to similar or identical elements throughout. When used herein in the context of a prosthetic heart valve, or a component thereof, the lengthwise, longitudinal, or axial direction refers to a direction parallel to a longitudinal axis passing through the center of the stent or heart valve from the inflow end to the outflow end, and the circumferential direction refers to a direction extending along the circumference of the prosthetic heart valve.

Although the following disclosure is made with reference to collapsible and expandable prosthetic heart valves, it is not intended to be so limited. Rather, the features disclosed herein may also be applied, where applicable, to surgical heart valves having a stent or frame that is not collapsible/expandable. Also, although the following disclosure is made with reference to a collapsible/expandable prosthetic aortic valve, the disclosure is also applicable to other collapsible/expandable cardiac valves, including the mitral valve, tricuspid valve, and the pulmonary valve.

Figure 1:
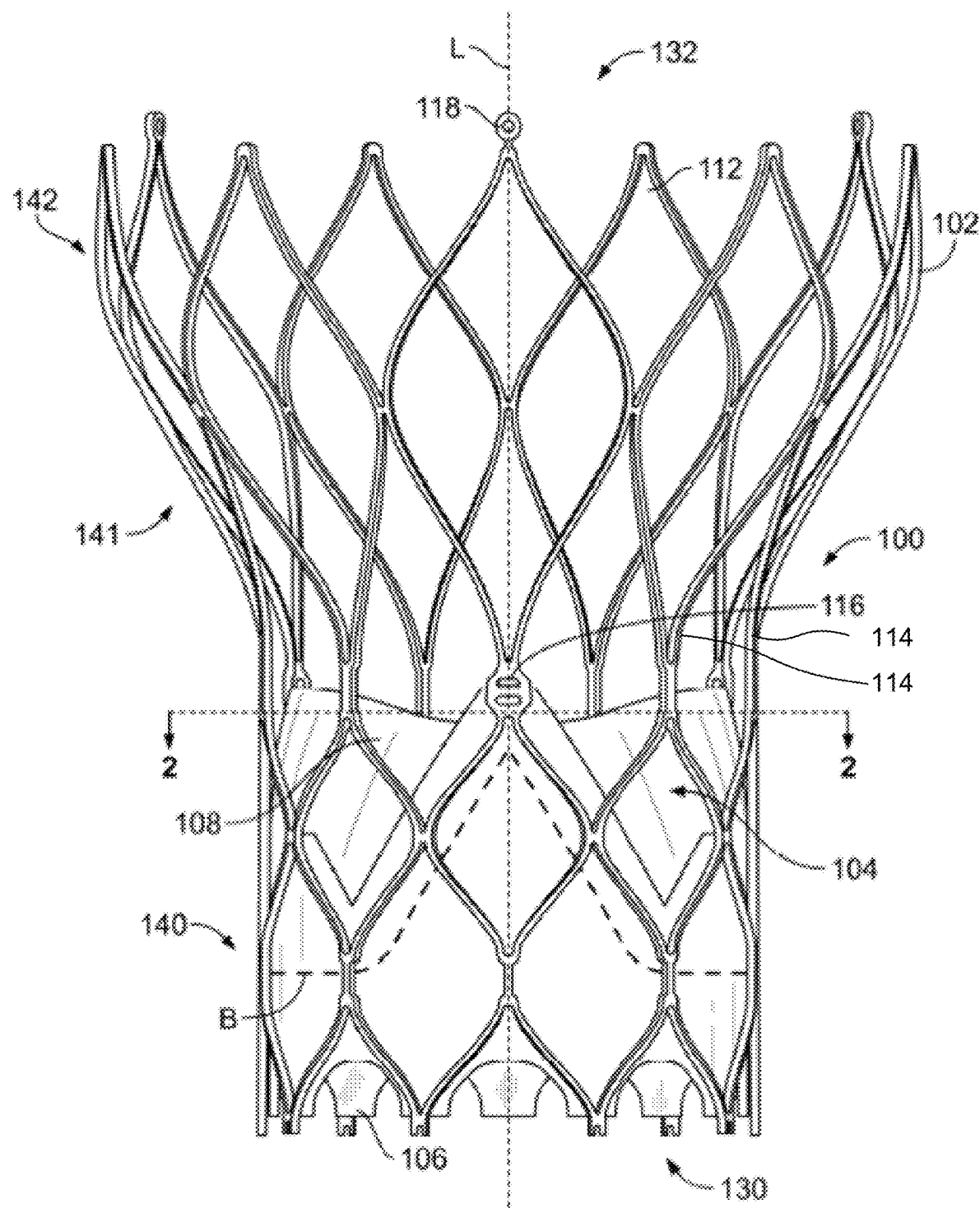
FIG. 1 is a front view of a collapsible prosthetic heart valve according to the prior art.

FIG. 1 shows a collapsible stent-supported prosthetic heart valve 100 according to the prior art, the prosthetic heart valve being shown in an expanded condition. Prosthetic heart valve 100 is designed to replace the function of the native aortic valve of a patient. Prosthetic heart valve 100 includes a stent 102 which serves as a frame for the valve elements. Stent 102 extends along a lengthwise or longitudinal axis L from an inflow or annulus end 130 to an outflow or aortic end 132, and includes an annulus section 140 adjacent inflow end 130 and an aortic section 142 adjacent outflow end 132. Annulus section 140 may be in the form of a cylinder having a substantially constant diameter along its length, and may have a relatively small transverse cross-section in the expanded condition in comparison to the transverse cross-section of aortic section 142. A transition section 141 may taper outwardly from annulus section 140 to aortic section 142. Each of the sections of stent 102 includes a plurality of cells 112 formed by interconnected struts 114. Each cell 112 may include four struts 114 connected together generally in a diamond shape so as to form a cell that may be readily collapsed and expanded. It will be appreciated that a smaller or larger number of struts may be used to form cells having a different shape. The cells 112 in each section of stent 102 may be connected to one another in one or more annular rows around the stent. For example, as shown in FIG. 1, annulus section 140 may have two annular rows of complete cells 112, with the cells in one annular row offset by one-half cell width in the circumferential direction from the cells in adjacent annular rows. Aortic section 142 and transition section 141 may each have one or more annular rows of complete or partial cells 112. The cells in aortic section 142 may be larger than the cells in annulus section 140, so as to better enable prosthetic valve 100 to be positioned within the aortic annulus without the structure of stent 102 interfering with blood flow to the coronary arteries. At least partly due to the shape of cells 112, stent 102 elongates in the direction of longitudinal axis L as the cells collapse when the stent transitions from the expanded condition to the collapsed condition and shortens in the direction of longitudinal axis L as the stent transitions from the collapsed condition to the expanded condition.

Stent 102 may include one or more retaining elements 118 at outflow end 132, the retaining elements being sized and shaped to cooperate with retaining structures provided on a delivery device (not shown). The engagement of retaining elements 118 with the retaining structures on the delivery device may help maintain prosthetic heart valve 100 in assembled relationship with the delivery device, minimize longitudinal movement of the prosthetic heart valve relative to the delivery device during unsheathing or resheathing procedures, and help prevent rotation of the prosthetic heart valve relative to the delivery device as the delivery device is advanced to the target location and during deployment. One such delivery device is described in U.S. Patent Publication No. 2012/0078352, the entire contents of which are hereby incorporated by reference herein.

Stent 102 may also include a plurality of commissure attachment features 116 for mounting the commissures of the valve assembly to the stent. As can be seen in FIG. 1, each commissure attachment feature 116 may lie at the intersection of four cells 112, two of the cells being adjacent one another in the same annular row, and the other two cells being in different annular rows and lying in end-to-end relationship. Commissure attachment features 116 may be positioned entirely within annulus section 140 or at the juncture of annulus section 140 and transition section 141, and may include one or more openings or apertures which facilitate the suturing of the leaflet commissures to stent 102. Stent 102 may be formed as a unitary structure, for example, by laser cutting or etching a tube of a superelastic and/or shape-memory metal alloy, such as a nickel-titanium alloy of the type sold under the designation nitinol. Such a unitary structure may be referred to as a "non-woven" structure in that it is not formed by weaving or winding one or more filaments.

Prosthetic heart valve 100 includes a valve assembly 104 positioned in the annulus section 140 of stent 102. Valve assembly 104 includes a plurality of leaflets 108 that collectively function as a one-way valve by coapting with one another, and a cuff 106 positioned on the luminal surface of stent 102 surrounding leaflets 108. As prosthetic heart valve 100 is intended to replace the aortic valve (which ordinarily is a tri-leaflet valve), it is shown in FIG. 1 with three leaflets 108. Adjacent leaflets 108 join one another at leaflet commissures. Each of the leaflet commissures may be sutured to a respective one of the three commissure attachment features 116. Between the leaflet commissures, each leaflet 108 may be sutured to stent 102 and/or to cuff 106 along a leaflet belly B, indicated with broken lines in FIG. 1. Leaflets 108 may be joined to stent 102 and/or to cuff 106 by techniques known in the art other than suturing. Above belly B, leaflets 108 are free to move radially inward to coapt with one another along their free edges. When prosthetic heart valve 100 is implanted in the native aortic valve annulus, blood flows in an antegrade direction from inflow end 130, past leaflets 108, and toward outflow end 132. This occurs when the pressure in the left ventricle is greater than the pressure in the aorta, forcing leaflets 108 to open. When the pressure in the aorta is greater than the pressure in the left ventricle, leaflets 108 are forced closed and coapt with one another along their free edges, blocking blood from flowing through prosthetic heart valve 100 in a retrograde direction from outflow end 132 to inflow end 130. It will be appreciated that prosthetic heart valves according to aspects of the present disclosure may have more or less than the three leaflets 108 and commissure attachment features 116 shown in FIG. 1 and described above.

Although cuff 106 is shown in FIG. 1 as being disposed on the luminal or inner surface of annulus section 140, the cuff may be disposed on the abluminal or outer surface of the annulus section or may cover all or part of either or both of the luminal and abluminal surfaces of the annulus section. The cuff may be formed from tissue or from a fabric, such as a biocompatible polymer fabric. Cuff 106 may be scalloped at the inflow end 130 of stent 102, and may have a zig-zag structure at its outflow end, following certain stent struts 114 up to commissure attachment features 116 and other stent struts closer to the inflow end of the stent at circumferential positions between the commissure attachment features. As is shown in FIG. 1, in one example, the entirety of valve assembly 104, including the leaflet commissures, is positioned in the annulus section 140 of stent 102. When open, leaflets 108 may remain substantially completely within annulus section 140, or they may be designed to extend into transition section 141. In the embodiment shown, substantially the entirety of valve assembly 104 is positioned between the inflow end 130 of stent 102 and commissure attachment features 116, and none of the valve assembly is positioned between the commissure attachment features 116 and the outflow end 132 of the stent.

In operation, prosthetic heart valve 100 described above may be used to replace a native heart valve, such as an aortic valve; a surgical heart valve; or a heart valve that has undergone a surgical procedure. Prosthetic heart valve 100 may be delivered to the desired site (e.g., near the native aortic annulus) using any suitable delivery device. During delivery, prosthetic heart valve 100 is disposed inside the delivery device in the collapsed condition. The delivery device may be introduced into the patient using any known percutaneous procedure, such as a transfemoral, transapical, or transseptal delivery procedure. Once the delivery device has reached the target site, the user may deploy prosthetic heart valve 100. Upon deployment, prosthetic heart valve 100 expands (or is balloon-expanded) into secure engagement within the native aortic annulus. When prosthetic heart valve 100 is properly positioned inside the heart, it works as a one-way valve, allowing blood to flow in one direction and preventing blood from flowing in the opposite direction.

Figure 2:
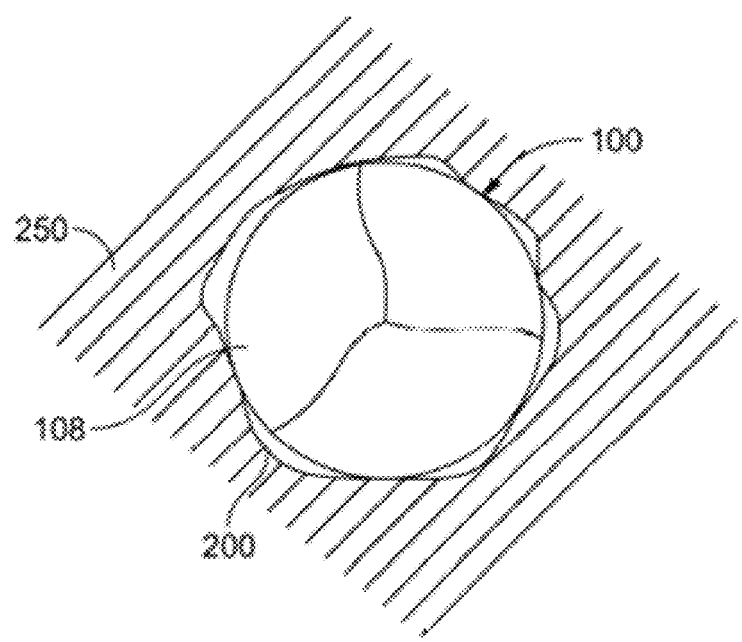
FIG. 2 is a highly schematic transverse cross-sectional view of the prior art prosthetic heart valve implanted in a patient, taken along line 2-2 of FIG. 1.

FIG. 2 is a highly schematic transverse cross-sectional illustration taken along line 2-2 of FIG. 1 and showing prosthetic heart valve 100 with leaflets 108 disposed within native valve annulus 250. The leaflets 108 may be formed from tissue or from a fabric, such as a biocompatible polymer fabric. As can be seen, the substantially circular annulus section 140 of stent 102 is disposed within a non-circular native valve annulus 250. At certain locations around the perimeter of prosthetic heart valve 100, gaps 200 are formed between the heart valve and native valve annulus 250. Retrograde blood flow through these gaps and around the outside of the valve assembly 104 of prosthetic heart valve 100 can result in paravalvular leakage ("PV leak") or regurgitation and other inefficiencies which can reduce cardiac performance. Such improper fit may be due to suboptimal native valve annulus geometry, for example, as a result of the calcification of the tissue of native valve annulus 250 or the presence of unresected native leaflets.

Figure 3A:
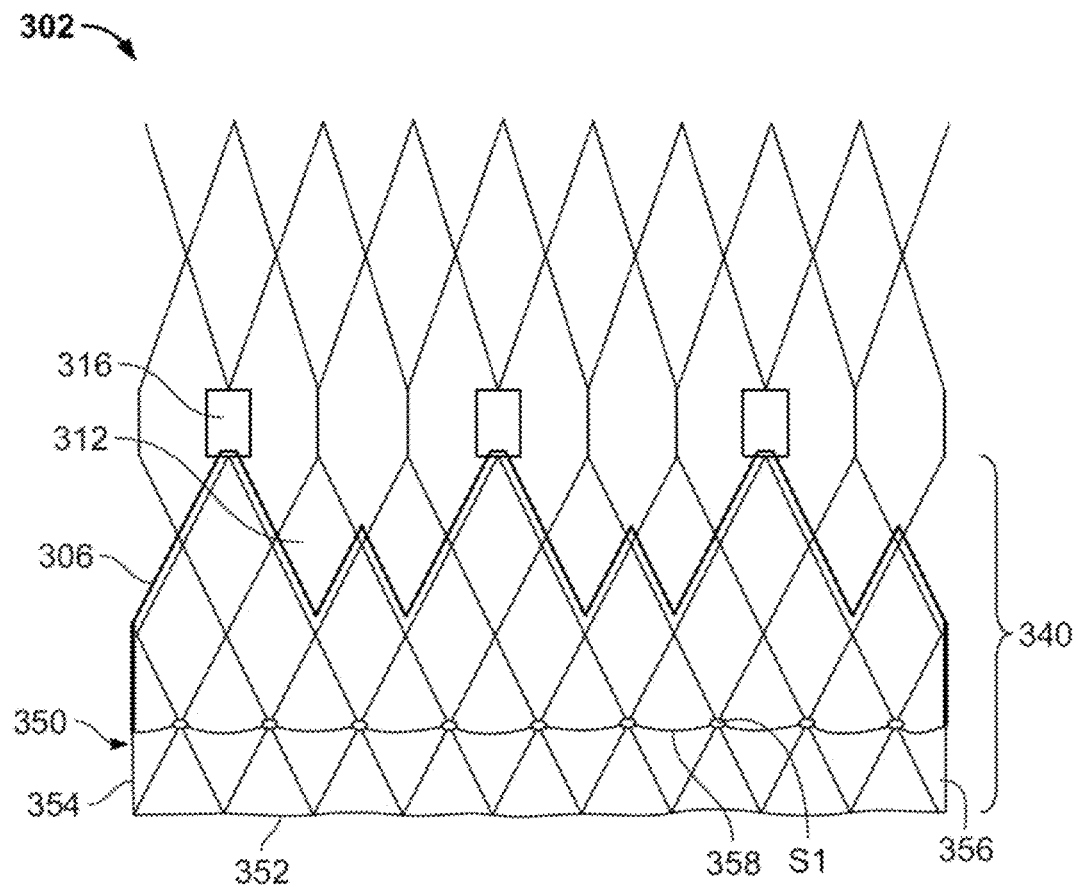
FIG. 3A is a schematic developed view of a stent with an outer cuff according to the prior art.

FIG. 3A illustrates the stent 302 of a prior art prosthetic heart valve. Stent 302 may be used in a prosthetic heart valve that is similar or identical to prosthetic heart valve 100 described above, with certain exceptions. For example, the annulus section 340 of stent 302 may include three rows of cells 312 instead of two rows, although in some embodiments stent 302 may include only two rows of cells in the annulus section. Although commissure attachment features 316 of stent 302 are illustrated as open rectangles in FIG. 3A, the commissure attachment features may have a form similar to commissure attachment features 116 shown in FIG. 1, or any other suitable form having any number of rows or columns of eyelets and/or eyelets of different sizes and/or shapes positioned in any arrangement on the commissure attachment feature. A cuff 306 similar or identical to cuff 106 may be positioned on the luminal or internal surface of stent 302, as shown in FIG. 3A, and/or on the abluminal surface of the stent. Rather than a scalloped inflow end as with cuff 106, however, cuff 306 may have a straight inflow end. In order to help minimize or eliminate PV leak, for example through the gaps 200 shown in FIG. 2, additional material may be coupled to the exterior of stent 302 as an outer cuff 350. (Outer cuff 350 is shown as if transparent in FIG. 3A so that the structure of stent 302 is visible.) In the illustrated example, outer cuff 350 may have a substantially rectangular shape and may be wrapped around the circumference of stent 302 at the inflow end of the stent so as to overlap in the longitudinal direction of the stent 302 with cuff 306. Outer cuff 350 may be a single piece of material having a proximal edge 352, two side edges 354, 356, and a distal edge 358. The proximal edge 352 of outer cuff 350 may be coupled to stent 302 and/or to inner cuff 306 at or near the inflow end of the stent, for example by a continuous line of sutures (not shown), with the side edges 354 and 356 of the outer cuff joined to one another so that retrograde blood flow entering the space between the outer cuff and the inner cuff cannot pass in the retrograde direction beyond the combined cuffs. In order to allow retrograde blood flow to enter the space between outer cuff 350 and inner cuff 306, the distal edge 358 of the outer cuff 350 may be attached to stent 302 and/or to inner cuff 306 at locations that are spaced apart in the circumferential direction. The distal edge 358 of outer cuff 350 may, for example, be sutured to stent 302 at attachment points S1 located where each cell 312 in the proximal-most row of cells intersects with an adjacent cell in that same row. In the illustrated example, since there are nine cells 312 in the proximal-most row, there are nine separate attachment points S1 at which the distal edge 358 of outer cuff 350 is sutured or otherwise attached to stent 302. Retrograde blood flow around the abluminal surface of stent 302 may enter the pocket or space between outer cuff 350 and inner cuff 306 via the spaces between adjacent attachment points S1. Once retrograde blood flow enters this space, outer cuff 350 may tend to billow outwardly, helping to fill any of gaps 200 between the prosthetic heart valve and native valve annulus 250. Although the foregoing description uses the term "inner" in connection with cuff 306, that is merely intended to indicate that cuff 306 is positioned radially inward of outer cuff 350. Inner cuff 306 may be located either on the luminal or abluminal side of stent 302, or on both sides.

Although described as a single piece of material above, outer cuff 350 may comprise multiple pieces of material that, when joined together, form a similar shape and provide a similar function as described above for the outer cuff. Also, rather than being formed of a single substantially rectangular piece of material that is wrapped around the circumference of stent 302, outer cuff 350 may be formed as a continuous annular web without side edges 354, 356. Preferably, outer cuff 350 has an axial height measured from its proximal edge 352 to its distal edge 358 that is approximately half the axial height of a cell 312 in the proximal-most row of cells in stent 302 as measured along the major axis of the cell between two of its apices when the cell is in an expanded condition. However, outer cuff 350 may have other suitable heights, such as the full axial height of a cell 312 in the proximal-most row of cells, or more or less than the full axial height of a cell 312 in the proximal-most row of cells. Still further, although inner cuff 306 and outer cuff 350 are described above as separate pieces of material joined to stent 302 and to each other, the cuffs may be formed integrally with one another from a single piece of material that is wrapped around the proximal edge of the stent, with the distal edge 358 of the outer portion of the cuff joined to the stent and/or to the inner portion of the cuff at attachment points S1 as described above. With this configuration, the proximal edge 352 of outer cuff 350 does not need to be sutured to stent 302, although it still may be preferable to provide such attachment. Inner cuff 306 and outer cuff 350 may be formed of the same or different materials, including any suitable biological material or polymer such as, for example, polytetrafluoroethylene (PTFE), ultra-high molecular weight polyethylene (UHMWPE), polyurethane, polyvinyl alcohol, silicone, or combinations thereof.

Figure 3B:
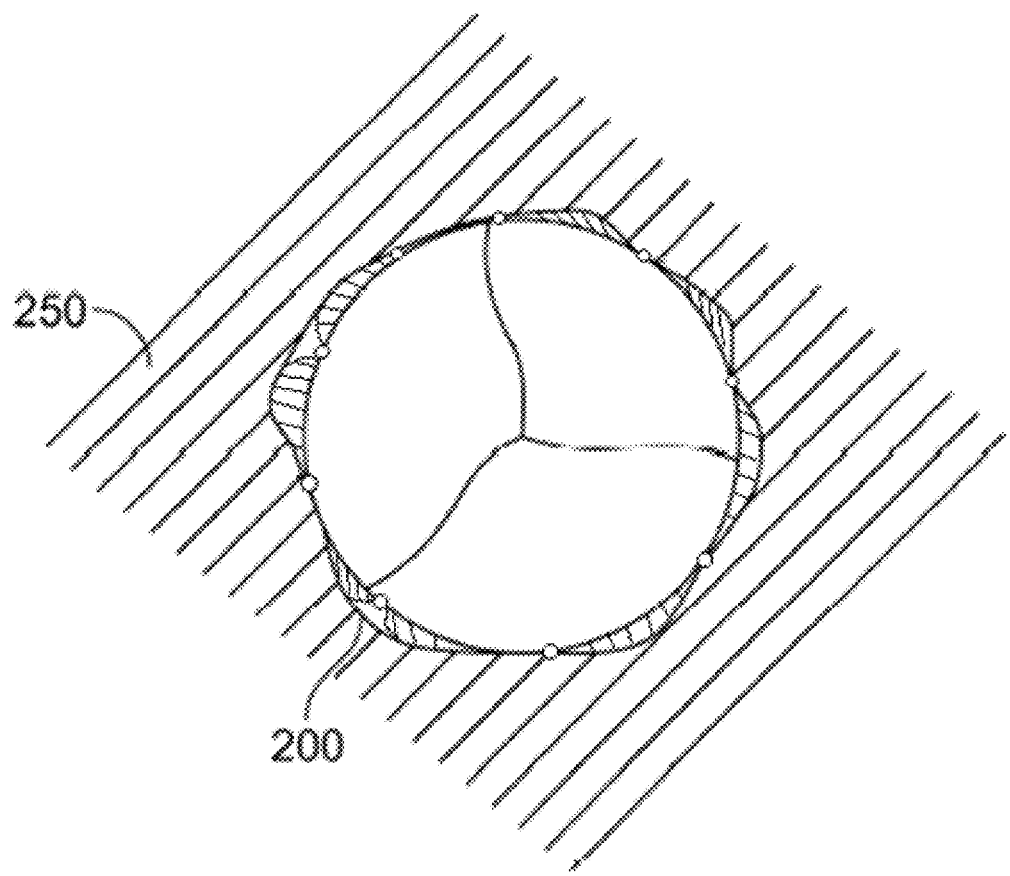
FIG. 3B is a highly schematic transverse cross-sectional view of a prosthetic heart valve including the stent and cuff of FIG. 3A implanted in a patient.

As shown in FIG. 3B, when a prosthetic heart valve including stent 302, inner cuff 306, and outer cuff 350 is implanted in a native valve annulus 250, retrograde blood flow may cause the outer cuff to billow radially outward and fill gaps 200. However, the attachment of the distal edge 358 of outer cuff 350 to stent 302 and/or to inner cuff 306 at attachment points S1 may prevent the outer cuff 350 from billowing outwardly at those points. If any gap 200 is radially aligned with, or nearly radially aligned with, an attachment point S1, outer cuff 350 may not be able to fill that gap. This situation is seen in FIG. 3B near the top left and bottom left of stent 302.

Figure 3C:
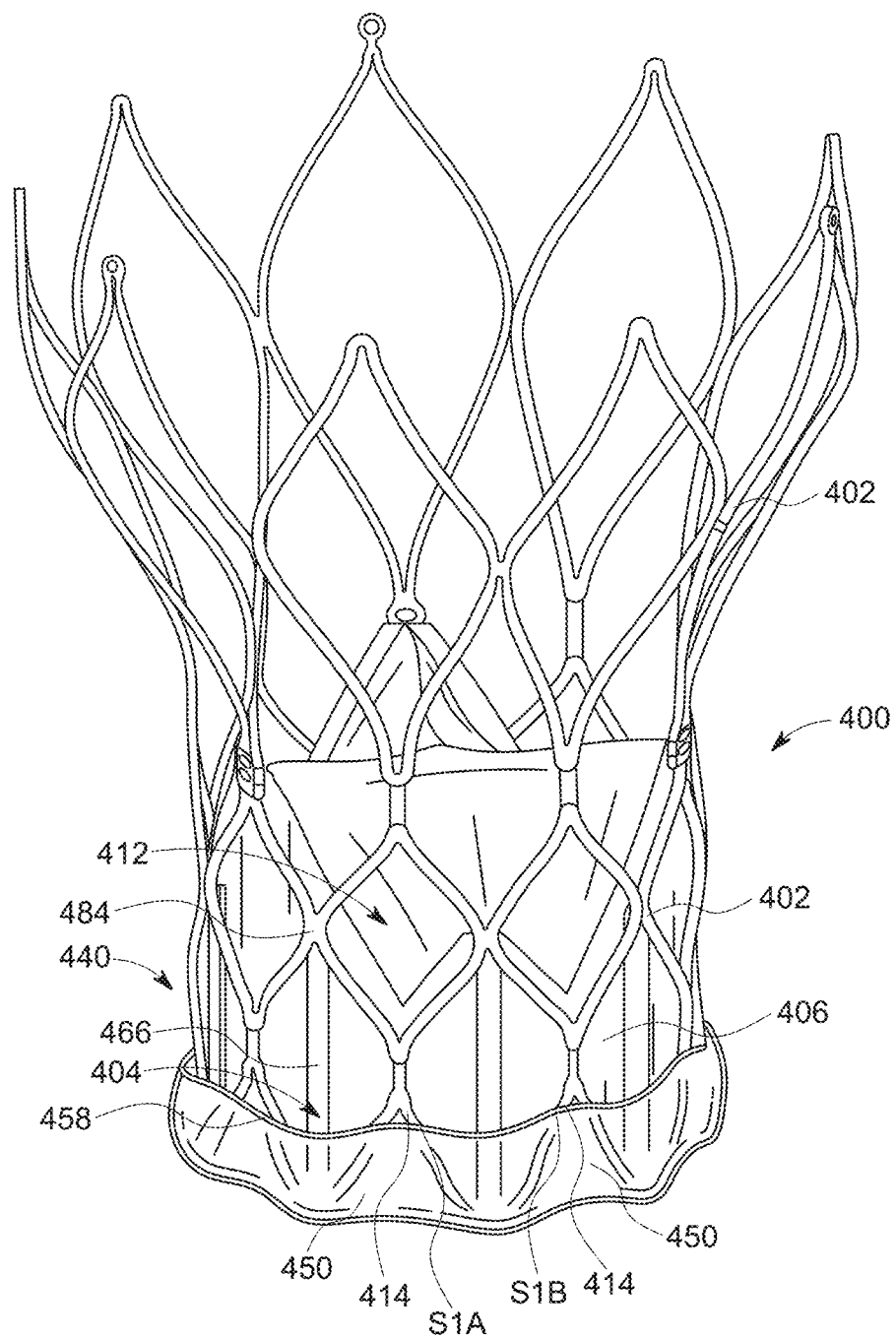
FIG. 3C is a perspective view of a prosthetic heart valve according to the prior art.

FIG. 3C illustrates another collapsible stent-supported prosthetic heart valve 400 according to the prior art, the prosthetic heart valve being shown in an expanded condition. The prosthetic heart valve 400 is similar to the valve shown in FIG. 3A and incudes a space or pocket 404 between the inner cuff 406 and outer cuff 450, as previously discussed. This forms a continuous expandable pocket 404 between the cuff portion 450 and the abluminal surface 484 of the stent 402 about the annulus section 440. Instead of being sutured to stent 402 at attachment points located where each cell 412 in the proximal-most row of cells intersects with an adjacent cell in that same row, the distal edge 458 may be sutured to adjacent struts 414 at attachment points S1A and S1B of each cell. As in the previous example, the pocket 404 is open facing in the distal direction circumscribing the stent 402, while closed facing in the proximal direction. The pocket 404 receives fluid pressure in the patient's aorta when deployed as an aortic valve to expand and seal around calcified nodules. Additional features can also be implemented to better enable the cuff of the prosthetic heart valve to fill any gaps that may remain once the heart valve has been implanted in a native valve annulus. For example, the distal edge 458 of the outer cuff 450 can be attached at different attachment points on stent 402.

Radiopaque Elements on Valve Cuff

According to aspects of the disclosure, placement of radiopaque elements on the cuff of a collapsible prosthetic heart valve can assist a surgeon with accurately positioning the heart valve within a human body. Such radiopaque elements can block radiation, rather than allowing radiation to pass through them, which causes the radiopaque element to be visible under a fluoroscope or on x-rays. Rather than being constrained to direct attachment to the underlying geometry and structure of the stent, the placement of radiopaque elements onto the fabric or tissue of a prosthetic heart valve allows greater freedom in selecting the areas at which radiopaque elements may be positioned on a valve. For example, radiopaque elements do not need to be directly attached to a strut of the stent, and may be positioned between struts, such as in the middle of a cell. Additionally, radiopaque elements are not limited in size to the underlying size of the stent structure and/or the portion of the stent to which the radiopaque element is attached. Larger radiopaque elements can be utilized, such as radiopaque elements that are larger than the width of a strut or the connection between two struts. Larger radiopaque elements can more easily be seen and detected under a fluoroscope, in x-rays, or with another medical imaging technique. Further, radiopaque elements can be strategically placed so as to minimize the overall profile of the prosthetic heart valve when the valve is collapsed for loading into the delivery system. This also allows for better visibility when the valve is collapsed and in the process of being deployed. These are just a few examples of the possibilities that may be achieved by placement of radiopaque elements on the fabric or tissue of a prosthetic heart valve. Examples of various radiopaque elements and their arrangements on the cuff are disclosed herein.

Figure 4:
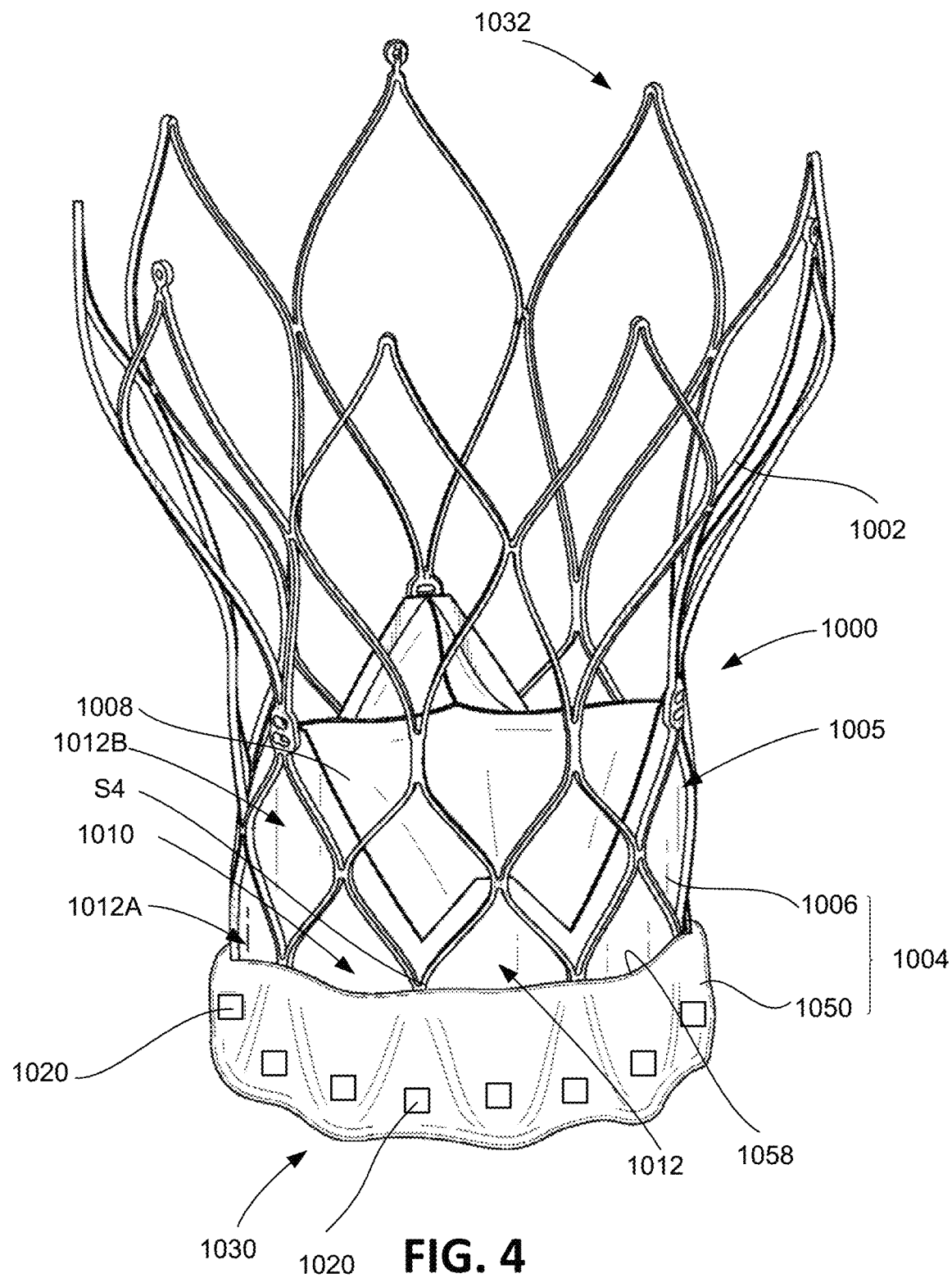
FIG. 4 is a perspective view of a prosthetic heart valve according to an embodiment of the disclosure.
Figure 5:
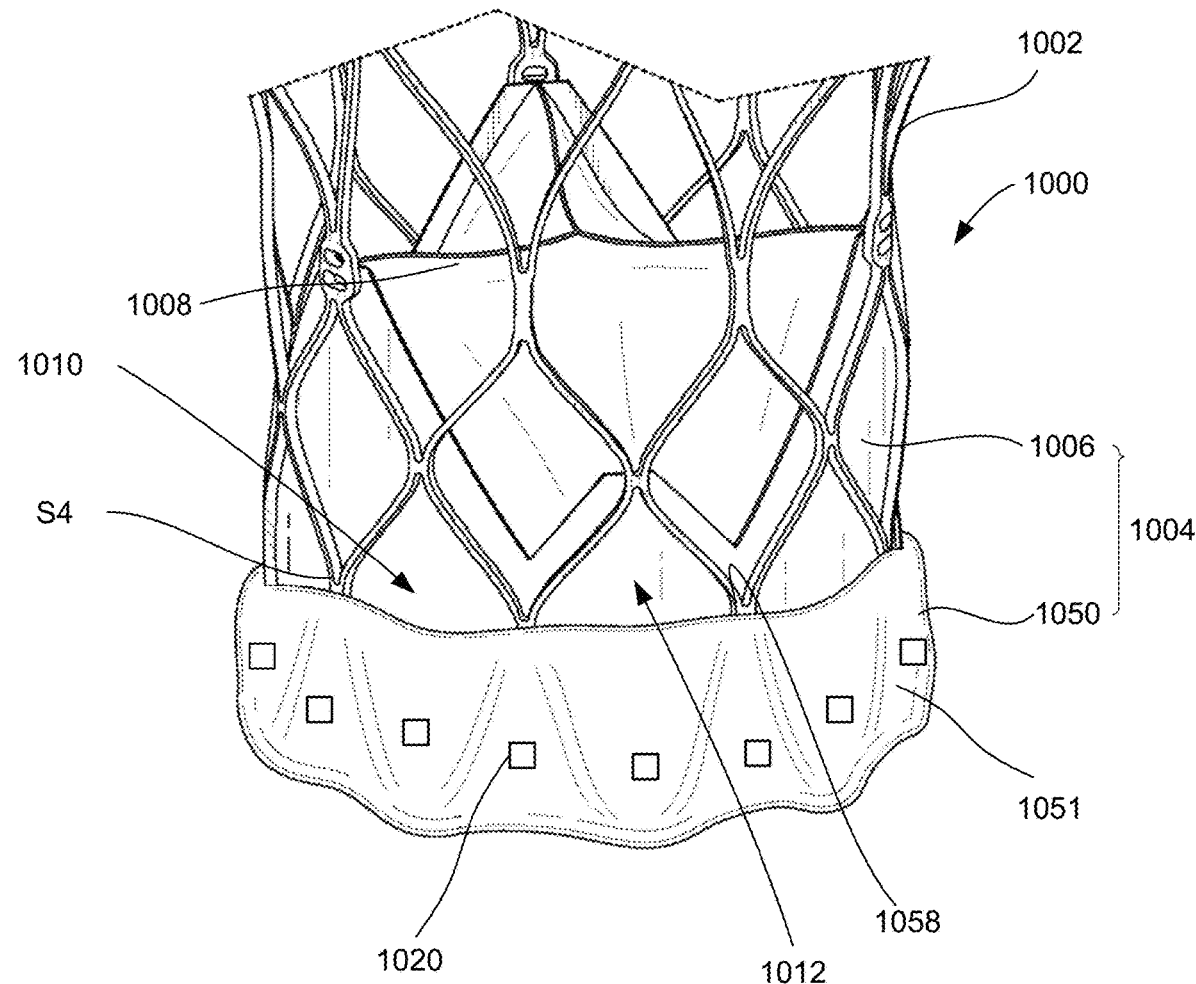
FIG. 5 is an enlarged perspective view of a portion of the prosthetic heart valve of FIG. 4.
Figure 6:
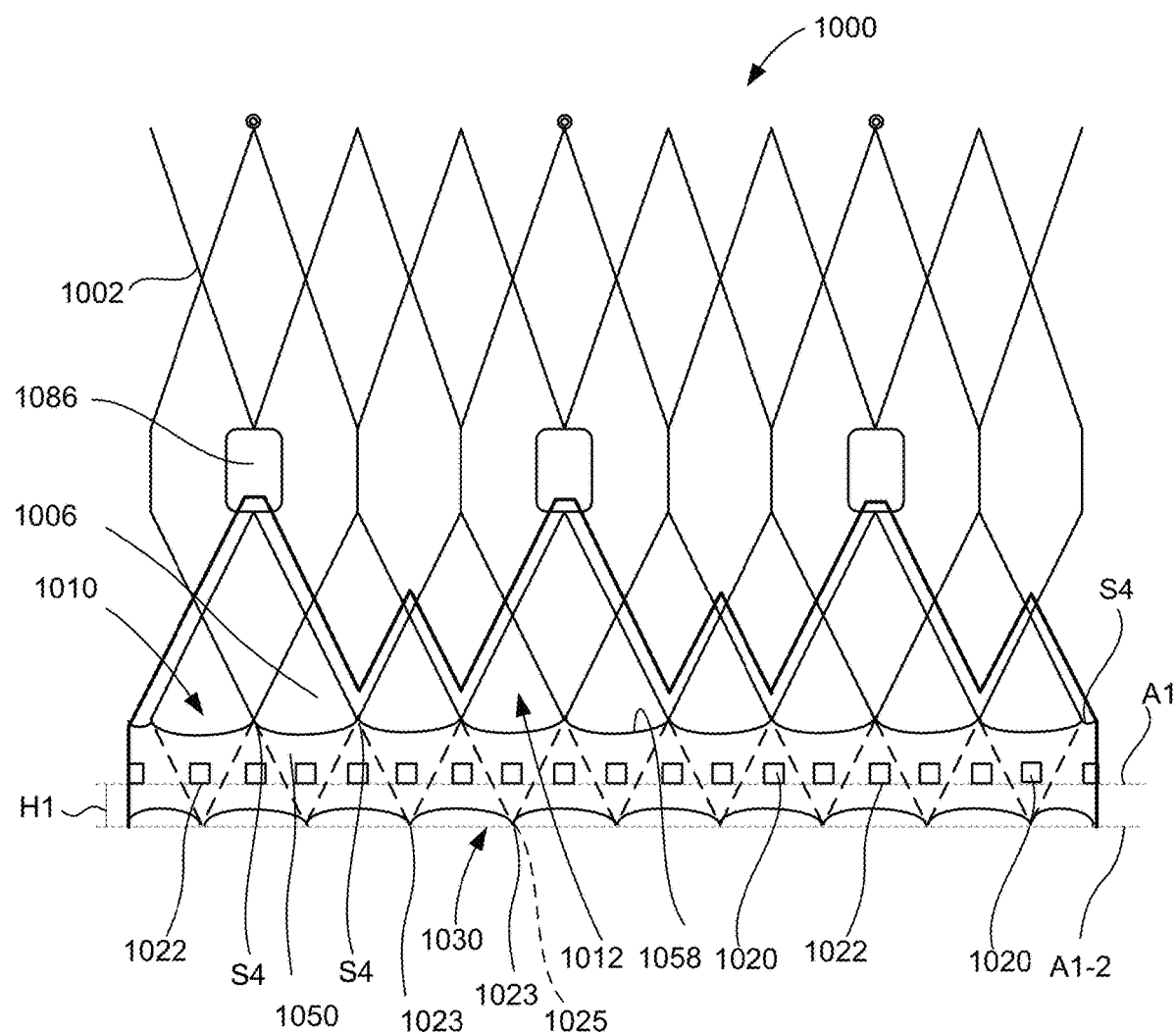
FIG. 6 is a schematic developed view of a stent and cuff as shown in FIG. 4.
Figure 7:
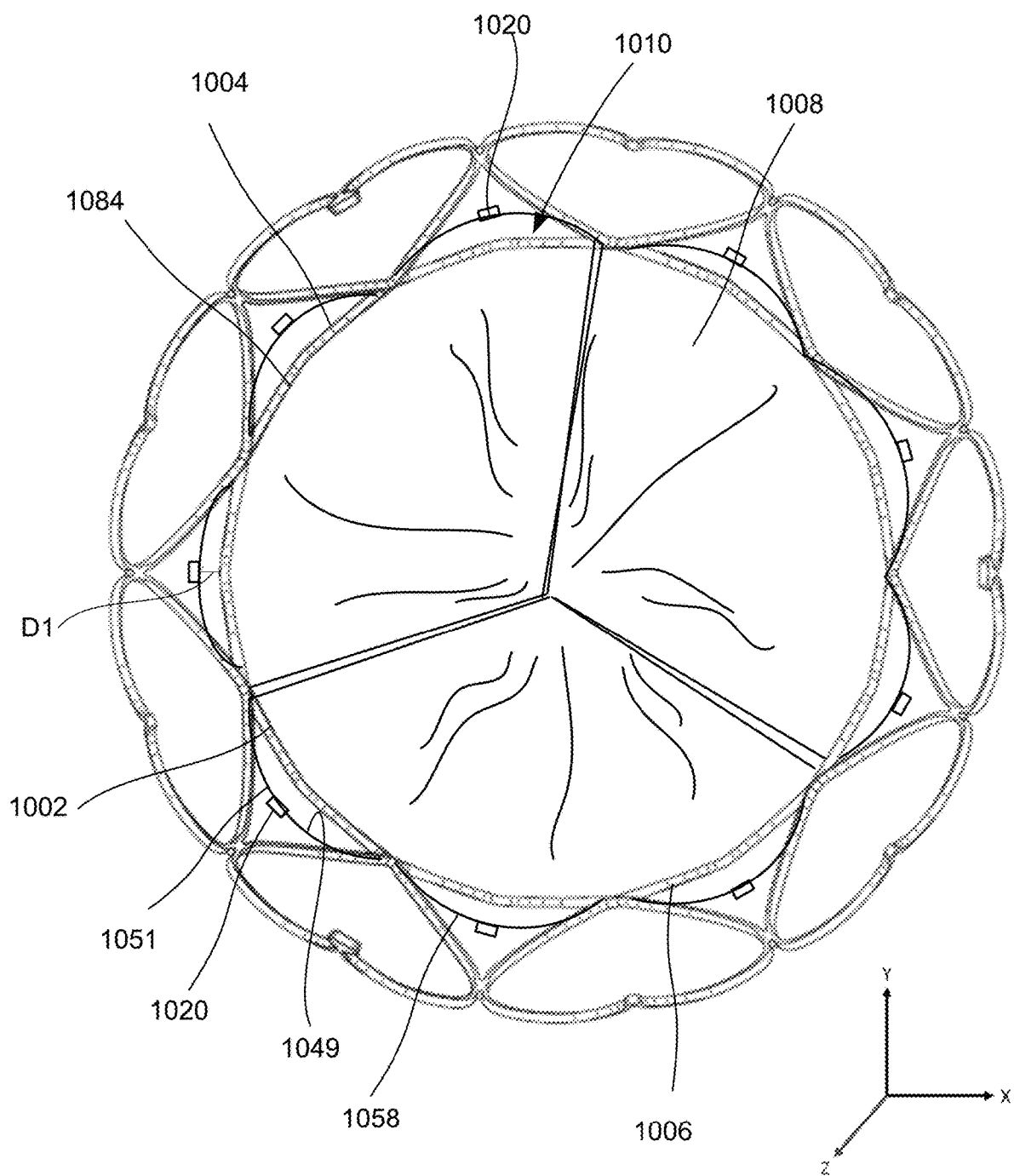
FIG. 7 is a schematic top view of the prosthetic heart valve of FIG. 4.

Referring to FIG. 4 and the corresponding enlarged view of FIG. 5, a stent-supported heart valve 1000 according to aspects of the disclosure is shown. Valve 1000 includes a similar underlying stent structure as the stent 102 in FIG. 1, stent 302 in FIG. 3A, and stent 402 in FIG. 3C, except that in this example, stent cells 1012 in the first row 1012A along the inflow end 1030 are joined together along a single point, similar to the stent cells 1012 in the directly adjacent second row 1012B. As shown, heart valve 1000 includes a stent 1002 and a valve assembly 1005, which further includes a plurality of leaflets 1008, and a cuff 1004. The leaflets and cuff may be formed from tissue or from a fabric, such as a biocompatible polymer fabric. In this example, the cuff 1004 includes an inner cuff 1006 and an outer cuff 1050, but in other examples, only the inner cuff 1006 may be present. As in the previous examples, the distal edge 1058 of outer cuff 1050 may, for example, be sutured to stent 1002 at attachment points S4 located where each cell 1012 in the proximal-most row of cells intersects with an adjacent cell in that same row. In the illustrated example, as best shown in the schematic view of FIG. 6, nine cells 1012 extend in the proximal-most row around the circumference of the annulus section of the heart valve 1000. The distal edge 1058 of outer cuff 1050 is sutured or otherwise attached to stent 1002 at nine attachments points S4. Retrograde blood flow around the abluminal surface of stent 1002 may enter the space or pocket 1010 formed between outer cuff 1050 and inner cuff 1006 via the spaces between adjacent attachment points S4. As shown in FIG. 7, outer cuff 1050 has an inner surface 1049 and an outer surface 1051. Outer cuff 1050 is spaced a distance D1 away from stent 1002 to form an opening between the outer cuff 1050 and inner cuff 1006. In this example, outer cuff 1050 defines an outer wall of pocket 1010 and inner cuff 1006 defines an inner wall of pocket 1010. Since distal edge 1058 is attached to stent 1002 only at points S4, a portion of the distal edge 1058 of outer cuff 1050 and also pocket 1010 can move in the x, y, and z directions, relative to the inner cuff 1006 and stent 1002. The distance D1 can therefore vary, depending on whether the prosthetic heart valve is collapsed, expanded, or at a position between collapsed and expanded.

To assist the surgeon in better identifying the location of heart valve 1000, and particularly, the position and orientation of the heart valve within a human body, including proper alignment of the heart valve 1000 with the aorta prior to deployment, heart valve 1000 may further include at least one element having radiopaque properties positioned on the cuff 1004, including the inner cuff 1006, the outer cuff 1050, or a combination of both the inner cuff 1006 and the outer cuff 1050. In this example, with reference back to FIGS. 4-6, radiopaque elements 1020 may be positioned on the outer surface 1051 of outer cuff 1050 and pocket 1010. The radiopaque elements 1020 may be positioned circumferentially around the outer cuff 1050 and the annulus section of heart valve 1000. Some of the radiopaque elements 1020 can be arranged to overlie the interior of cells 1012 or be radially aligned with the interior of the cells, while other radiopaque elements 1020 can be positioned between two adjacent cells 1012. All of radiopaque elements 1020 are shown at about the same distance from the inflow end 1030 of heart valve 1000, but in other examples, radiopaque elements 1020 may be positioned in any pattern or arrangement on the cuff 1004. For example, the distance of radiopaque elements 1020 from inflow end 1030 may be staggered, and/or the radiopaque elements may be provided in less than all of the cells, and/or in less than all or in no spaces between the cells.

Radiopaque elements 1020 may be attached to one or more positions on the pocket 1010 formed in cuff 1004 so that they are capable of moving relative to stent 1002 of heart valve 1000, as well as relative to the leaflets 1008 and cells 1012 of stent 1002. With reference to FIG. 7, the radiopaque elements 1020 are shown attached to the outer surface 1051 of pocket 1010 and outer cuff 1050, but can also be attached to the inner surface 1049, as will be seen in other embodiments. The placement of radiopaque elements 1020 on the pocket 1010 allows the radiopaque elements 1020 to move in the x, y, and z directions relative to the inner cuff 1006 and stent 1002. Radiopaque elements 1020 can therefore move with pocket 1010 and outer cuff 1050 toward the abluminal surface 1084 of stent 1002 and inner cuff 1006, away from the abluminal surface 1084 of stent 1002 and inner cuff 1006, toward the inflow end 1030 of valve 1000, and toward the outflow end 1032 of valve 1000. Radiopaque elements 1020 can therefore be spaced up to a distance D1 away from the stent 1002 of heart valve 1000, with the distance D1 being limited by the size of the pocket 1010 and outer cuff 1050. Distance D1 is therefore variable and will change as radiopaque elements 1020 move with pocket 1010.

Positioning radiopaque elements on the outer surface 1051 of outer cuff 1050 can be beneficial to reduce the overall profile of the collapsed valve. When the heart valve is collapsed, the thicknesses of the radiopaque element can adversely increase the overall profile of the collapsed valve, especially in situations where two or more radiopaque elements may become stacked or vertically aligned one on top of the other when the valve is collapsed. When the outer cuff 1050 and pocket 1010 are collapsed and radiopaque elements 1020 are positioned on the outer surface 1051 of outer cuff 1050, the pocket 1010 will become slightly elongate and form flaps of material projecting radially outward around the circumference of the collapsed valve. One way of avoiding stacking, for example, may be to fold the flap against the collapsed heart valve 1000 such that the radiopaque elements 1020 do not become radially stacked or overlie one other. Instead, in the collapsed condition, the radiopaque elements can be arranged around the circumference of the collapsed valve 1000 so that they are directly adjacent one another. This can help to minimize the overall size of collapsed heart valve 1000, as well as allow for placement of radiopaque elements in strategic places that will not impact the overall profile of the heart valve when the heart valve is collapsed for loading into the delivery system.

Radiopaque elements can also be strategically placed onto heart valve 1000 and cuff 1050 to assist the surgeon with seeing desired portions of the prosthetic heart valve under fluoroscopy or other medical imaging technique, as well as seeing the position of the heart valve within the body. For example, radiopaque elements 1020 may be positioned to provide increased visibility of the leading edge of the stent 1002 under medical imaging, as well as greater control over implant depth relative to the native valve annulus. As shown in FIG. 6, radiopaque elements 1020 may have their lower edges 1022 circumferentially aligned with one another along a reference line A1 that extends circumferentially around the inflow end 1030 of the stent 1002. Reference line A1 may be positioned a distance H1 away from a second reference line A1-2 that extends circumferentially between each lowermost point 1023 at the stent tip 1025 of inflow end 1030 of the stent 1002. The distance H1 can vary, but can be set, for example, at 3 mm for the target depth.

Figure 8:
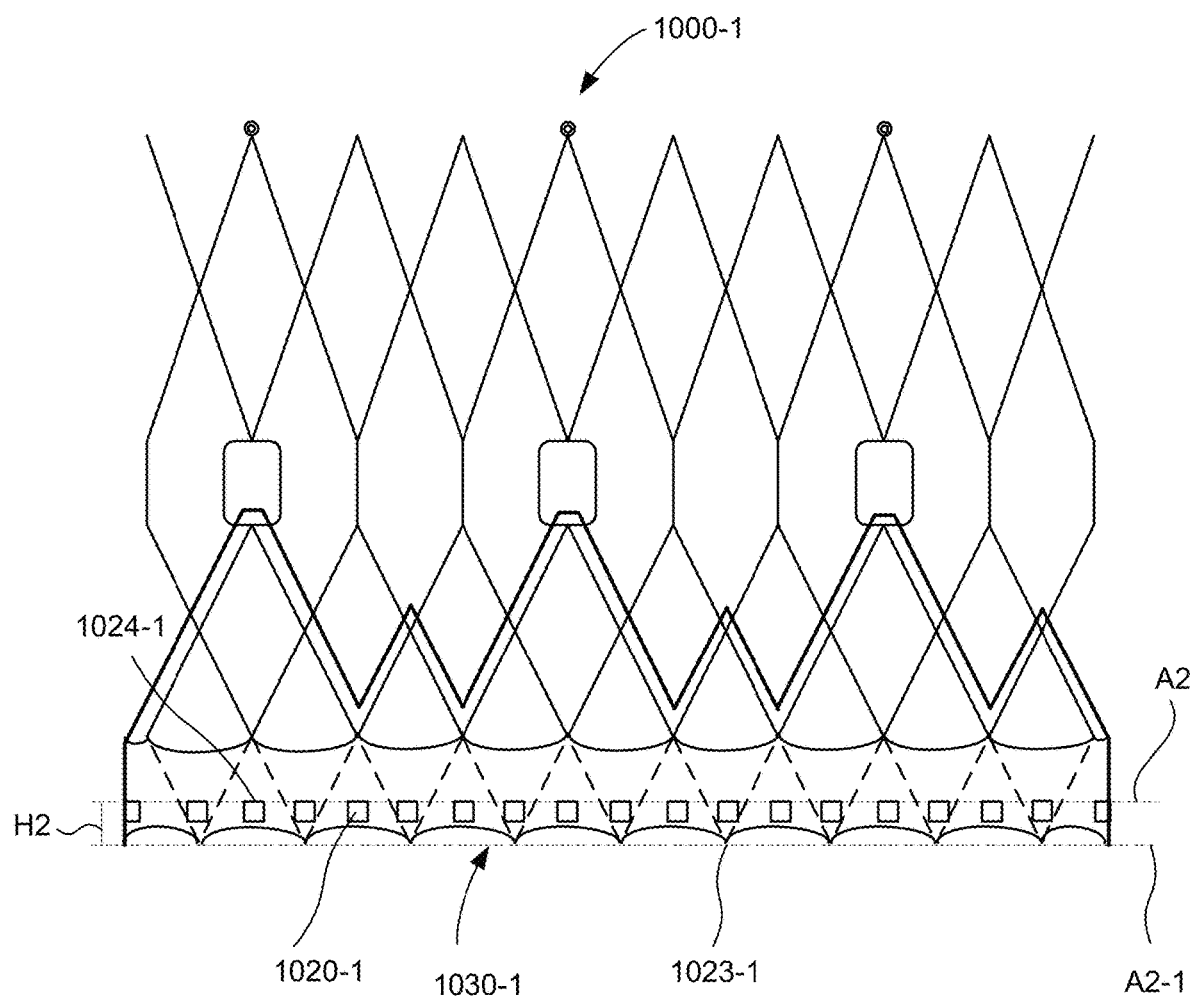
FIG. 8 is a schematic developed view of a stent and cuff according to another embodiment of the disclosure.

In other examples, such as shown in FIG. 8, the top edges 1024-1 of the radiopaque elements 1020-1 may be circumferentially aligned along reference line A2 positioned at a distance H2 from a reference line A2-1 that extends circumferentially between each lowermost point 1023-1 of inflow end 1030-1. This can allow a surgeon to use the top edges 1024-1 of radiopaque elements 1020-1 to determine the appropriate depth for implanting heart valve 1000-1.

Figure 9:
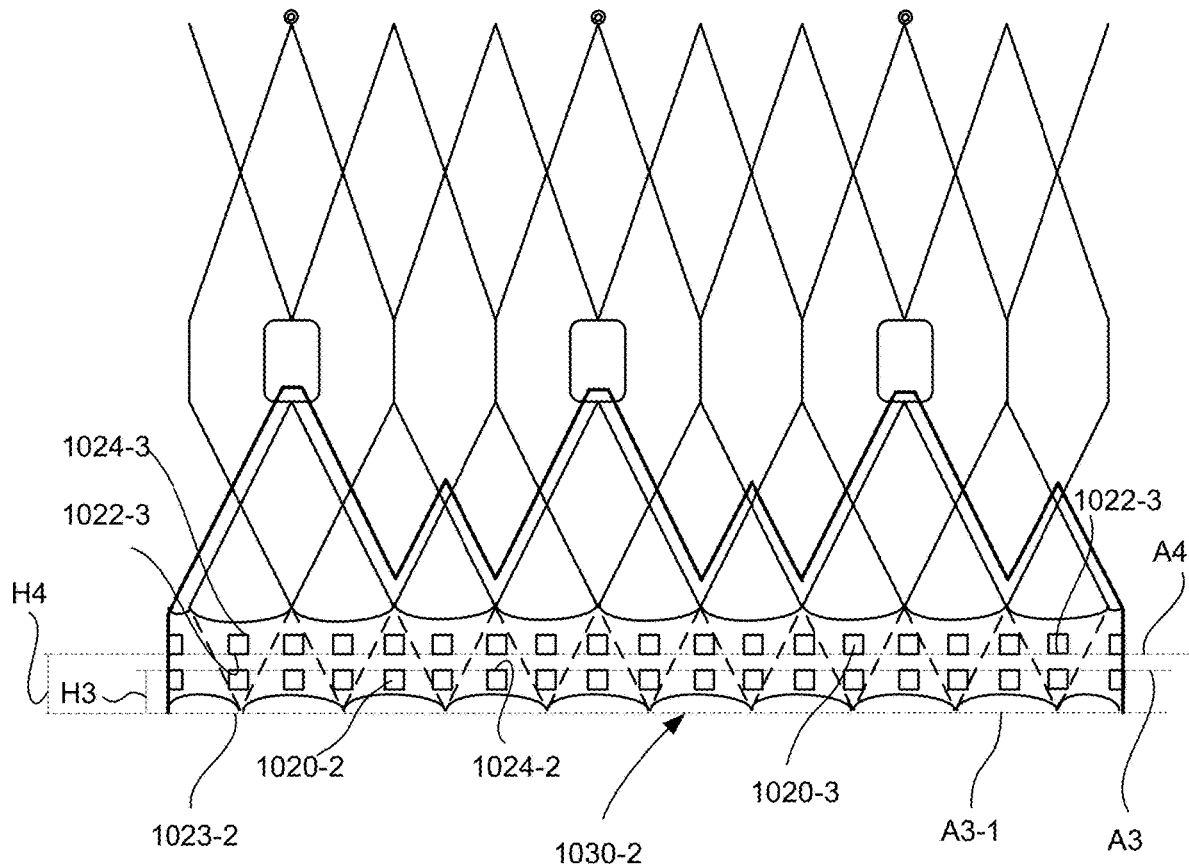
FIG. 9 is a schematic developed view of a stent and cuff according to another embodiment of the disclosure.

FIG. 9 shows yet another example that includes two rows of radiopaque elements. A first row of radiopaque elements 1020-2 may include top edges 1024-2 circumferentially aligned with one another along a reference line A3 positioned at a distance H3 from reference line A3-1 at the inflow end 1030-2 of the stent. Reference line A3-1 may extend circumferentially around inflow end 1030-2, and in this example, reference line A3-1 extends between each lowermost point 1023-2 of inflow end 1030-2. The second row of radiopaque elements 1020-3 may include bottom edges 1022-3 circumferentially aligned with one another along a reference line A4, which is positioned at a distance H4 away from reference line A3-1 at the inflow end 1030-2 of the stent. The space between and bounded by the top edges 1024-2 of radiopaque elements 1020-2 and the bottom edges 1022-3 of radiopaque elements 1020-3 can provide a visual indicator of a desired or acceptable range of depth that would be suitable for implantation purposes. For example, where H3 is 3 mm and H4 is 4 mm, the acceptable depth at which heart valve 1000 may be implanted is 3-4 mm. In other examples, depths H1-H4 can vary depending on the desired purpose, if any, for positioning the radiopaque elements on the outer cuff 1050.

The radiopaque elements may be comprised of any materials that possess radiopaque properties. For example, the radiopaque elements may be formed from a metal incorporating stainless steel, but the metal may be comprised of any radiopaque material, including other metals, including titanium or aluminum, or metal alloys. Each radiopaque element may be a radiopaque clad marker that incorporates a metal, such as gold, platinum, platinum-iridium, tantalum, tantalum-tungsten, or other metals or metal alloys bonded to an underlying metal, such as stainless steel or nitinol. Examples of radiopaque clad markers include tantalum-clad stainless steel and gold-clad nitinol. Radiopaque elements can comprise radiopaque sutures. In one example, a suture material made may be embedded or loaded with a material that will appear on a fluoroscope, x-ray, or other medical image. For example, the suture material may be comprised of polyethylene or polymer fiber that is loaded with a radiopaque material. Barium sulfate is one example of a radiopaque material that can be provided on or in a radiopaque suture material, but other radiopaque materials can be loaded on or in the sutures to achieve a radiopaque suture. Similarly, other types of suture material in combination with any radiopaque material can be utilized.

Figure 10A:
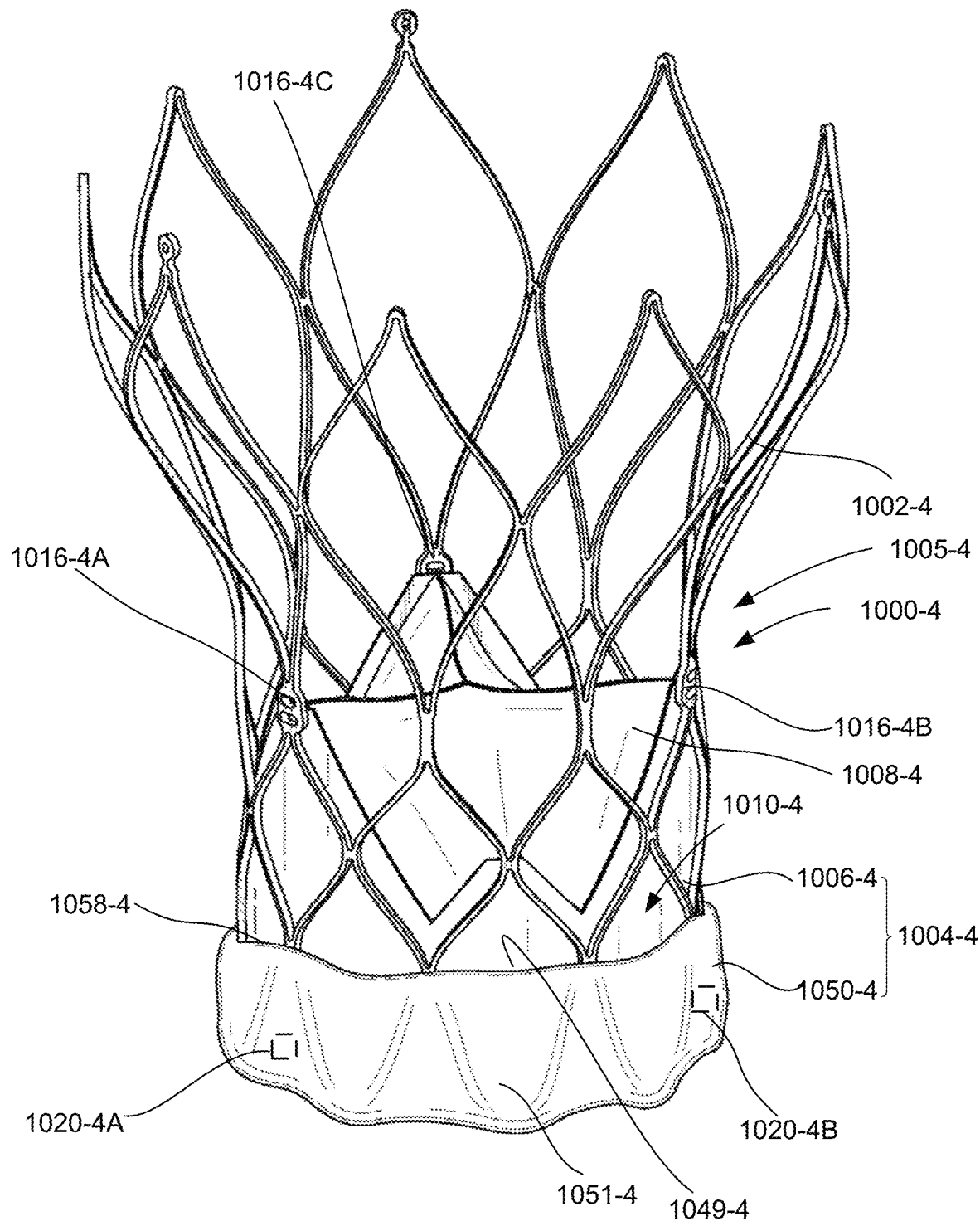
FIG. 10A is a perspective view of a prosthetic heart valve according to an embodiment of the disclosure.
Figure 10B:
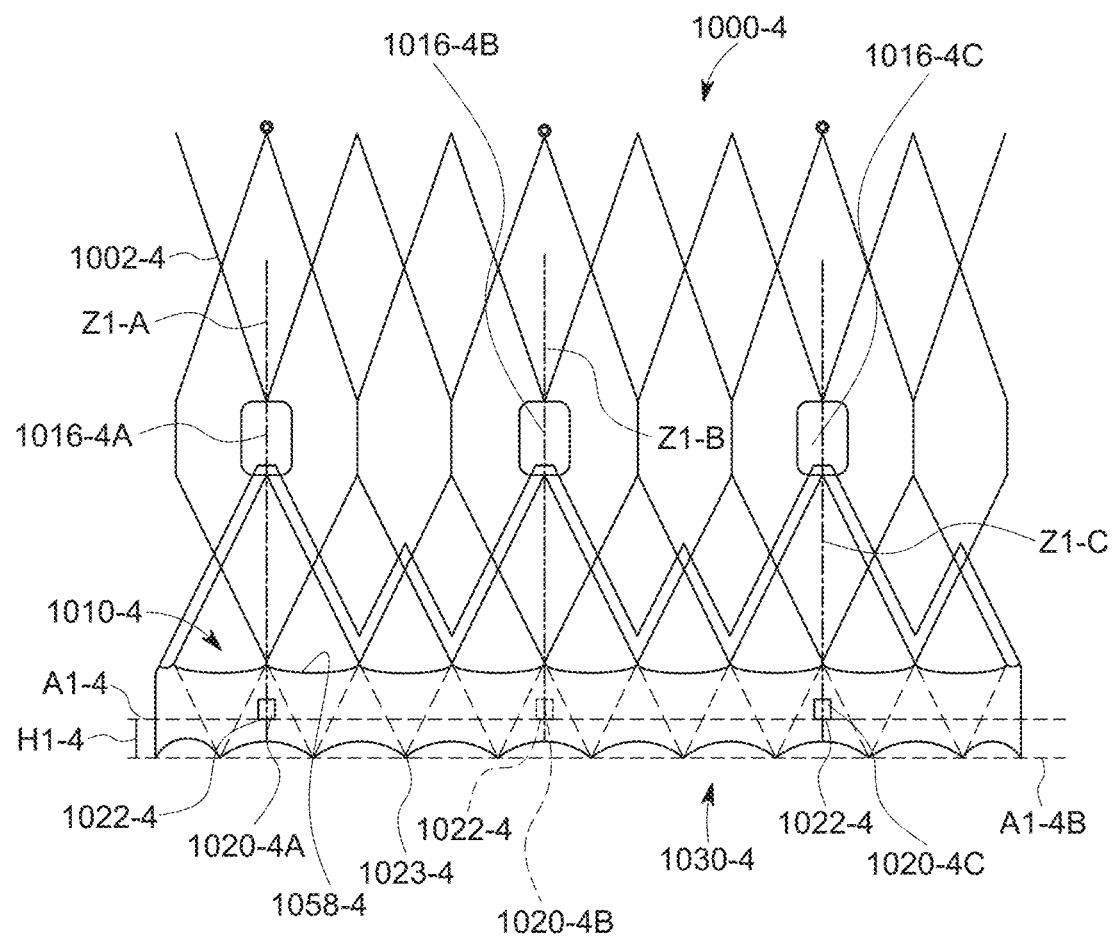
FIG. 10B is a schematic developed view of a stent and cuff as shown in FIG. 10A.
Figure 10C:
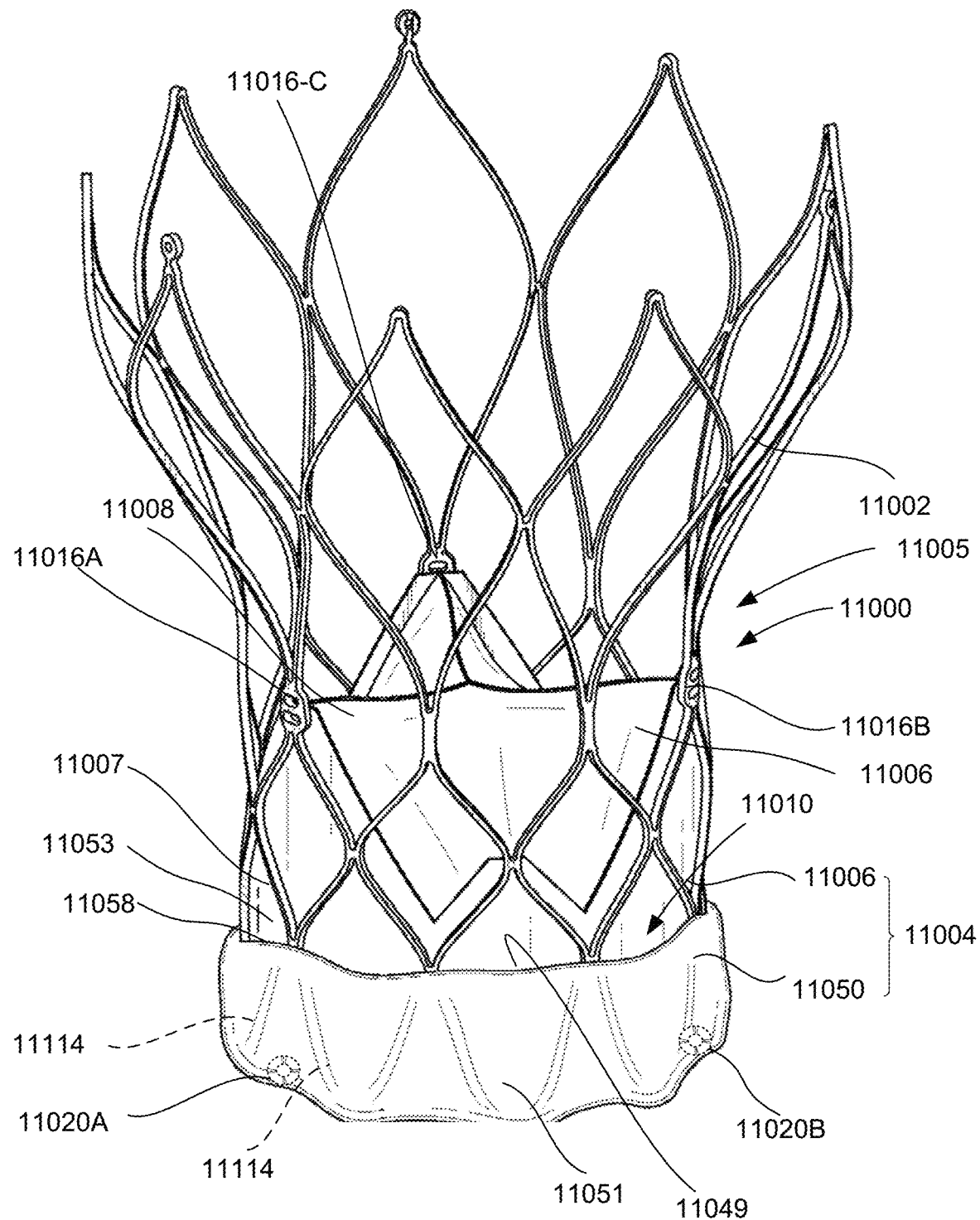
FIG. 10C is a perspective view of a prosthetic heart valve according to an embodiment of the disclosure.

FIGS. 10A-10B illustrate another stent-supported heart valve 1000-4 according to aspects of the disclosure. Stent-supported heart valve 1000-4 includes a similar underlying stent structure 1002-4 as the stent 1002 in FIGS. 4-9. As the present example differs only in the arrangement of radiopaque elements around the outer cuff 1050-4, a detailed discussion of the underlying features of the stent 1002-4 and heart valve assembly 1005-4 (including leaflets 1008-4 and cuff 1004-4 (which in this example includes an inner cuff 1006-4 and an outer cuff 1050-4)) are not discussed.

At least one radiopaque element may be aligned with at least one of the commissure attachment features on the stent 1002-4 to assist a surgeon with identifying the location of the at least one commissure attachment feature. In one example, three radiopaque elements 1020-4A, 1020-4B, and 1020-4C can each be vertically aligned along a longitudinal axis extending through any portion of the respective commissure attachment features on the stent 1002-4. For example, as shown in FIG. 10B, first radiopaque element 1020-4A may be aligned along an axis Z1-A extending through a portion of first commissure attachment feature 1016-4A, second radiopaque element 1020-4B may be aligned with second commissure attachment feature 1016-4B along axis Z1-B, and third radiopaque element 1020-4C may be aligned along axis Z1-C with a third commissure attachment feature 1016-4C. Positioning the radiopaque element 1020-4A, 1020-4B, 1020-4C in alignment with the respective commissure attachment features 1016-4A, 1016-4B, 1016-4C can help a surgeon identify the location of all three prosthetic valve commissures. In this example, the center of each commissure attachment feature is aligned with the center of each corresponding radiopaque element. But, in other examples, any portions of the commissure attachment feature and radiopaque element may be generally aligned along the longitudinal axis extending through the commissure attachment feature.

The radiopaque elements aligned with one or more commissure attachment features can be positioned on any portions of the prosthetic heart valve, such as the cuff (inner cuff 1006-4 and/or outer cuff 1050-4), the leaflets 1008-4, or the stent 1002-4. In this example, at least one radiopaque element, and particularly the first radiopaque element 1020-4A, is positioned on an outer surface 1051-4 of the outer cuff 1050-4. Third radiopaque element 1020-4C is additionally positioned on the outer surface 1051-4 of the outer cuff 1050-4. At least one radiopaque element, and particularly second radiopaque element 1020-4B, may be positioned on an interior surface 1049-4 of the outer cuff 1050-4 and within the pocket 1010-4 formed between the outer cuff 1050-4 and the inner cuff 1006-4. In other examples, all three radiopaque elements are positioned on the interior surface 1049-4 of the outer cuff 1050-4 and within the pocket 1010-4 or alternatively, all three radiopaque elements 1020-4A, 1020-4B, and 1020-4C may be positioned on the outer surface 1051-4 of the outer cuff 1050-4.

Although not required, in some examples, each of the radiopaque elements 1020-4A, 1020-4B, and 1020-4C may additionally have their lower edges 1022-4 circumferentially aligned with one another along a circumferential reference line A1-4A that extends around the inflow end 1030-4 of the stent 1002-4. Reference line A1-4A may be positioned a distance H1-4 away from a second reference line A1-4B that extends circumferentially between each lowermost point 1023-4 of inflow end 1030-4 of the stent 1002-4. The distance H1-4 can vary, but can be set, for example, at 3 mm from the very edge of the implant represented by line A1-4B to aid the user in positioning the implant at a 3 mm target depth. In other examples, all three radiopaque elements may have an upper edge aligned with one another, or only two radiopaque elements may have at least one edge aligned with one another, or none of the upper or lower edges of the radiopaque elements 1020-4A, 1020-4B, 1020-4C may be aligned with one another. In still other examples, one or more of the radiopaque elements may be positioned on the inner cuff 1006-4 that is exposed above the top edge 1058-4 of the outer cuff 1050-4, as will be further discussed herein, or on the inner cuff 1006-4 within the pocket 1010-4, such that the radiopaque element is not visible or only partially visible adjacent the top edge 1058-4 of the outer cuff 1050-4.

FIGS. 10C-10G illustrate another stent-supported heart valve 11000 according to aspects of the disclosure. Stent-supported heart valve 11000 includes a similar underlying stent structure 11002 as the stent 1002 in FIGS. 4-9 and 10A-10B. As the present example differs only in the specific arrangement of radiopaque elements around the cuff 11004 and how the radiopaque elements are attached to the cuff, a detailed discussion of the underlying features of the stent 11002 and heart valve assembly 11005 (including leaflets 11008 and cuff 11004 (which in this example includes an inner cuff 11006 and an outer cuff 11050)) are not discussed.

Figure 10D:
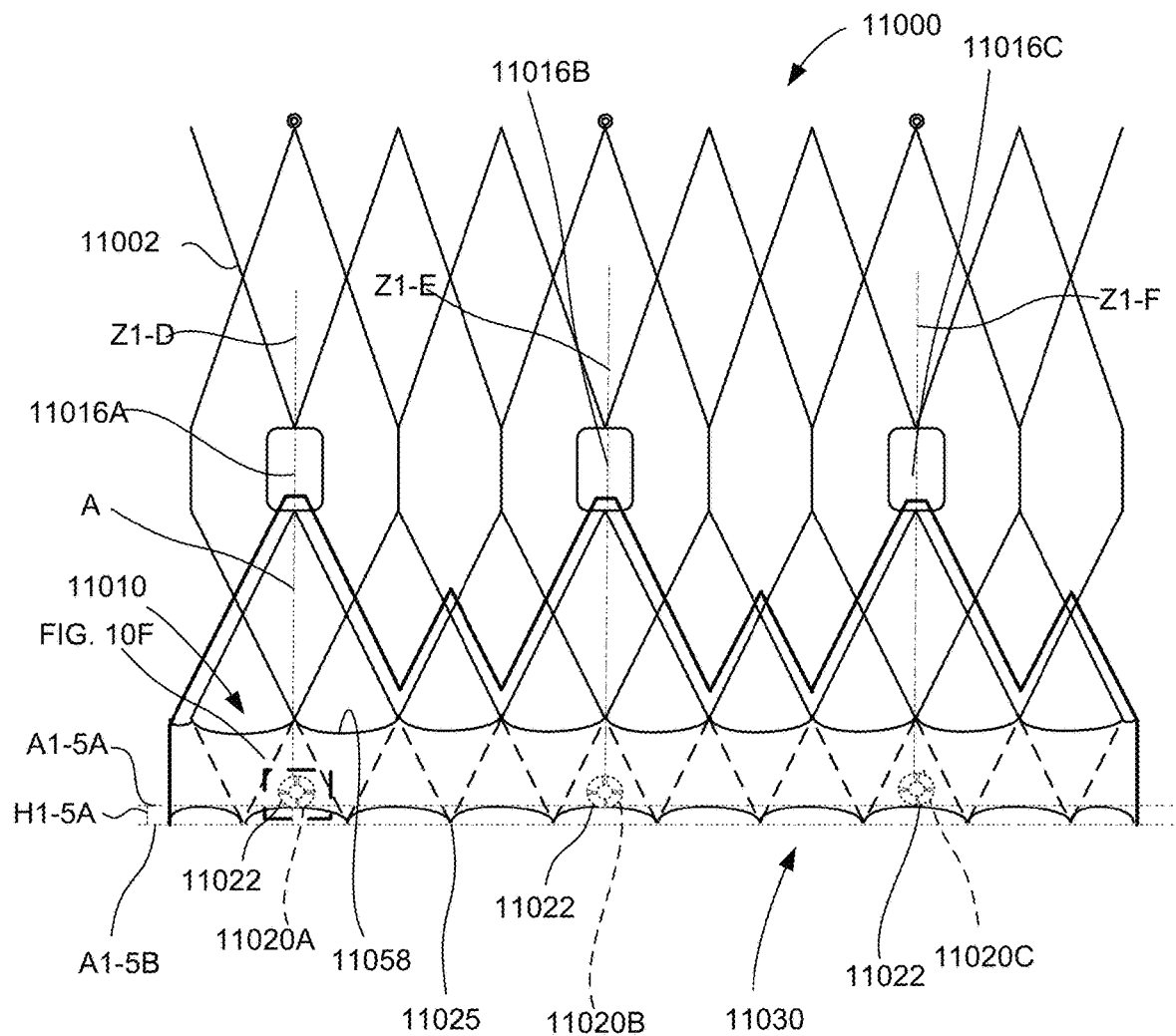
FIG. 10D is a schematic developed view of a stent and cuff as shown in FIG. 10C.

At least one radiopaque element may be aligned with at least one of the commissure attachment features on the stent 11002 to assist a surgeon with identifying the location of the at least one commissure attachment feature. In one example, three radiopaque elements 11020A, 11020B, and 11020C can each be vertically aligned along a longitudinal axis extending through any portion of the respective commissure attachment features on the stent 11002. For example, as shown in FIG. 10D, first radiopaque element 11020A may be aligned along an axis Z1-D extending through a portion of first commissure attachment feature 11016A, second radiopaque element 11020B may be aligned with second commissure attachment feature 11016B along axis Z1-E, and third radiopaque element 11020C may be aligned along axis Z1-F with a third commissure attachment feature 11016C. Positioning each of the radiopaque elements 11020A, 11020B, 11020C in alignment with the respective commissure attachment features 11016A, 11016B, 11016C can help a surgeon identify the location of all three prosthetic valve commissures. In this example, the center of each commissure attachment features is aligned with the center of each corresponding radiopaque element. But, in other examples, any portions of the commissure attachment feature and radiopaque element may be generally aligned along the longitudinal axis extending through the commissure attachment feature.

Each of the radiopaque elements that are aligned with one or more commissure attachment features can be positioned on any portion of the prosthetic heart valve, such as the cuff (inner cuff 11006 and/or outer cuff 11050), the leaflets 11008, or the stent 11002. In some examples, at least one radiopaque element may be positioned between an interior surface 11049 of the outer cuff 11050 and an outer surface 11007 of the inner cuff 11006, or within the pocket 11010 formed between the outer cuff 11050 and the inner cuff 11006. In this example, all three radiopaque elements are positioned between the interior surface 11049 of the outer cuff 11050 and the outer surface 11007 of the inner cuff 11006, as well as within the pocket 11010, but in other examples, one or more of the radiopaque elements 11020A, 11020B, and 11020C may be positioned on the outer surface 11051 of the outer cuff 11050 or an interior surface 11005A (FIG. 10G) of the inner cuff 11006.

The radiopaque elements may take on any shape, as further discussed in connection with FIGS. 12A-12H. At least one of the radiopaque elements may be in the shape of a circle, and in some examples may further include an opening. In this example, as shown in FIG. 10D, all three radiopaque elements 11020A, 11020B, 11020C are circular in shape and include an opening 11021 extending through the thickness 11023 of the radiopaque element. FIG. 10E illustrates a schematic example of radiopaque element 11020A, which is identical in this example, to radiopaque elements 11020B and 11020C. A top plan view, a side view, and a perspective view of the radiopaque element 11020A are shown. Radiopaque element 11020A includes a thickness 11023 and a central opening 11021 extending through the thickness of the radiopaque element. One or more of the radiopaque elements may be attached to the inner cuff 11006 and/or outer cuff 11050 and/or within the pocket 11010, and/or other part of the prosthetic heart valve, such as by suturing or use of an adhesive. In this example, the opening 11021 provides a means for the radiopaque element to be sutured to the prosthetic heart valve, and particularly to the cuff 11004 attached to the prosthetic heart valve.

Figure 10F:
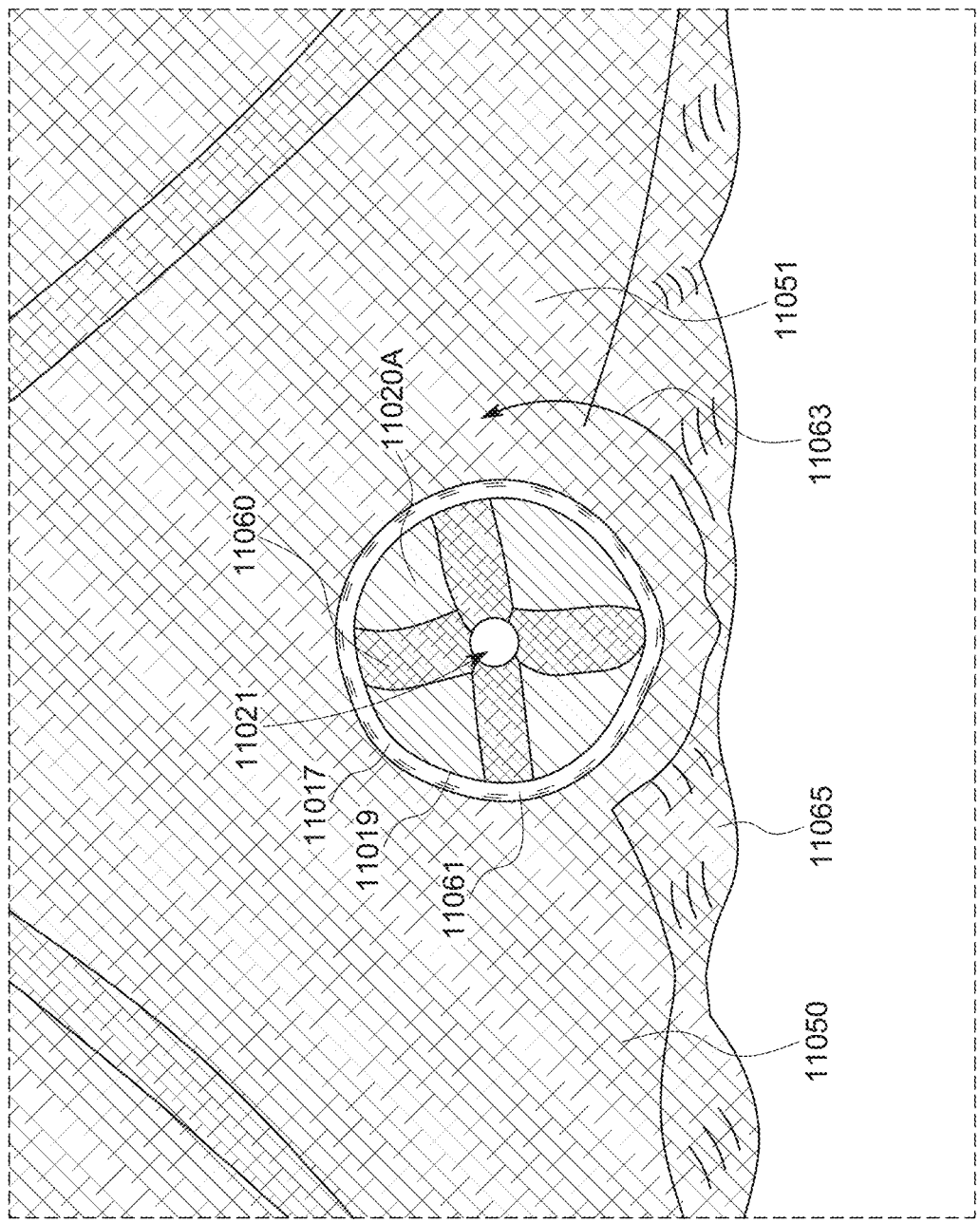
FIG. 10F is an enlarged plan view of a portion of the prosthetic heart valve of FIG. 10D.
Figure 10G:
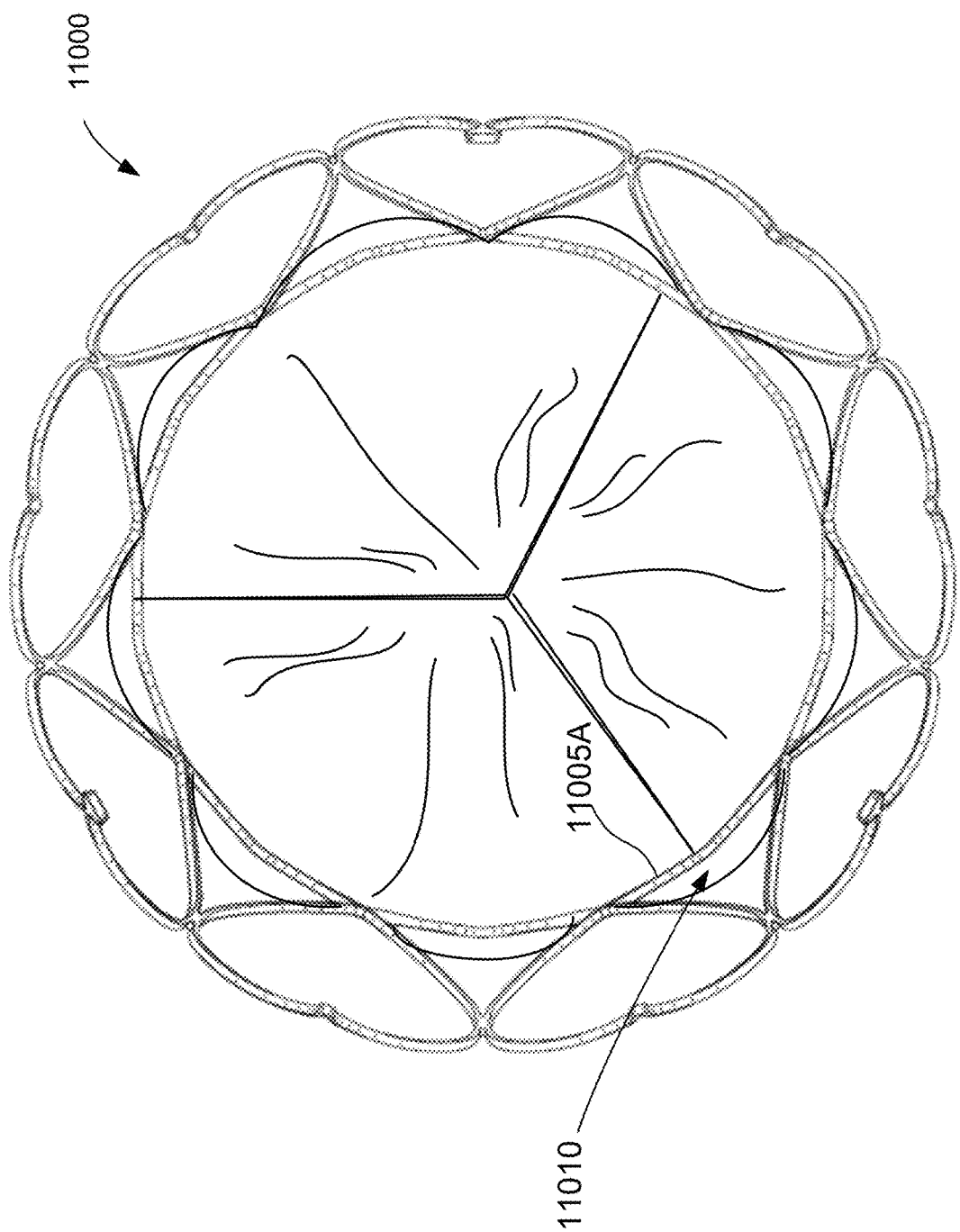
FIG. 10G is a schematic top view of the prosthetic heart valve shown in FIG. 10C.

Various sutures, suture patterns, and methods of suturing may be used to secure radiopaque elements to the prosthetic valve. At least one of the radiopaque elements may be sutured to the cuff 11004, and in this example, all three radiopaque elements 11020A, 11020B, and 11020C are sutured to the cuff 11004. As shown in FIG. 10F, an enlarged view of a portion of FIG. 10D, radiopaque element 11020A is positioned within the pocket 11010 and sutures 11060 extend along the outer surface 11051 of the outer cuff 11050 and the interior surface 11005A (FIG. 10G) of the inner cuff 11006, such that the radiopaque element may be positioned between struts 11002 of adjacent cells.

The arrangement of the sutures 11060 can collectively create a suture pattern. The suture pattern, in this example, is in the shape of a cross, but any suture pattern can be utilized. With the radiopaque element positioned within the pocket 11010 and between the inner cuff 11006 and outer cuff 11050, the suture 11060 may extend along the outer surface 11051 of the outer cuff and the interior surface 11005A of interior cuff 11006. In one example, as shown, the suture may extend from adjacent the outer peripheral edge 11019 of the radiopaque element 11020A, over the top surface 11017 of the radiopaque element and the outer cuff 11050, through the opening 11021, and around the bottom surface 11015 of the radiopaque element and the interior surface 11005A of the inner cuff 11006. This suture pattern may be repeated at symmetric intervals around the circumference of the radiopaque element to form the shape of the cross, but in other examples a non-symmetric suture pattern may be used and any number of sutures in any number of positions relative to the radiopaque element may be used. For example, instead of a cross-shape pattern, the suture pattern may be formed around the circumference of the radiopaque element by continuously and repeatedly extending through the opening 11021 and around the exterior surface 11051 of the outer cuff 11050 and the interior surface 11005A of the inner cuff 11006.

Additionally, or alternatively, another suture 11061 or suture pattern may extend around the outer peripheral edge of the radiopaque element. Although not required, including both sutures 11060, 11601 provides redundancy to ensure that the radiopaque element is secured to the prosthetic heart valve and to minimize the risk of embolization. In this example, because the radiopaque element 11020A is in the shape of a disc or circle, the suture pattern is circular and extends circumferentially around the peripheral edge 11019 of the radiopaque element. As shown, the suture extends along the outer surface 11051 of the outer cuff 11050, and will also extend along and through the interior surface (not shown) of the inner cuff 11006.

In one example, the suture 11061 extends in the direction of arrow 11063. Suture 11061 may be a continuous suture that extends from the lower inflow edge 11065 of the outer cuff 11050 and inner cuff 11006, around the perimeter 11019 of the radiopaque element 11020A, and back down around to the lower inflow edge 11065 of the prosthetic valve. Suture 11061 can continue along the lower inflow edge 11065 of the prosthetic heart valve, such as where the outer cuff 11050 and inner cuff 11006 join together. The suture 11061 can then similarly extend around other radiopaque elements in the valve structure.

Although not required, in some examples, at least two of the radiopaque elements 11020A, 11020B, and 11020C may additionally have their lower edges 11024 circumferentially aligned with one another along a circumferential reference line A1-5A that extends around the inflow end 11030 of the stent 11002. In the example shown in FIG. 10D, all three radiopaque elements may have a lowermost edge 11022 aligned with one another. Reference line A1-5A may be positioned a distance H1-5A away from a second reference line A1-5B that extends circumferentially between each lowermost point 11025 of inflow end 11030 of the stent 11002. The distance H1-5A can vary, but can be set, for example, at 3 mm from the very edge of the implant represented by line A1-5B to aid the user in positioning the implant at a 3 mm target depth. In other examples, all three radiopaque elements may have upper edges aligned with one another, or only two radiopaque elements may have upper and/or lower edges aligned with one another, or none of the upper or lower edges of the radiopaque elements 11120A, 11020B, 11020C may be aligned with one another. In still other examples, one or more of the radiopaque elements may be positioned on the inner cuff 11006 that is exposed above the top edge 11058 of the outer cuff 11050, as will be further discussed herein, or on the inner cuff within the pocket 11010, such that it is not visible or is only partially visible adjacent the top edge 11058 of the outer cuff 11050.

Figure 11A:
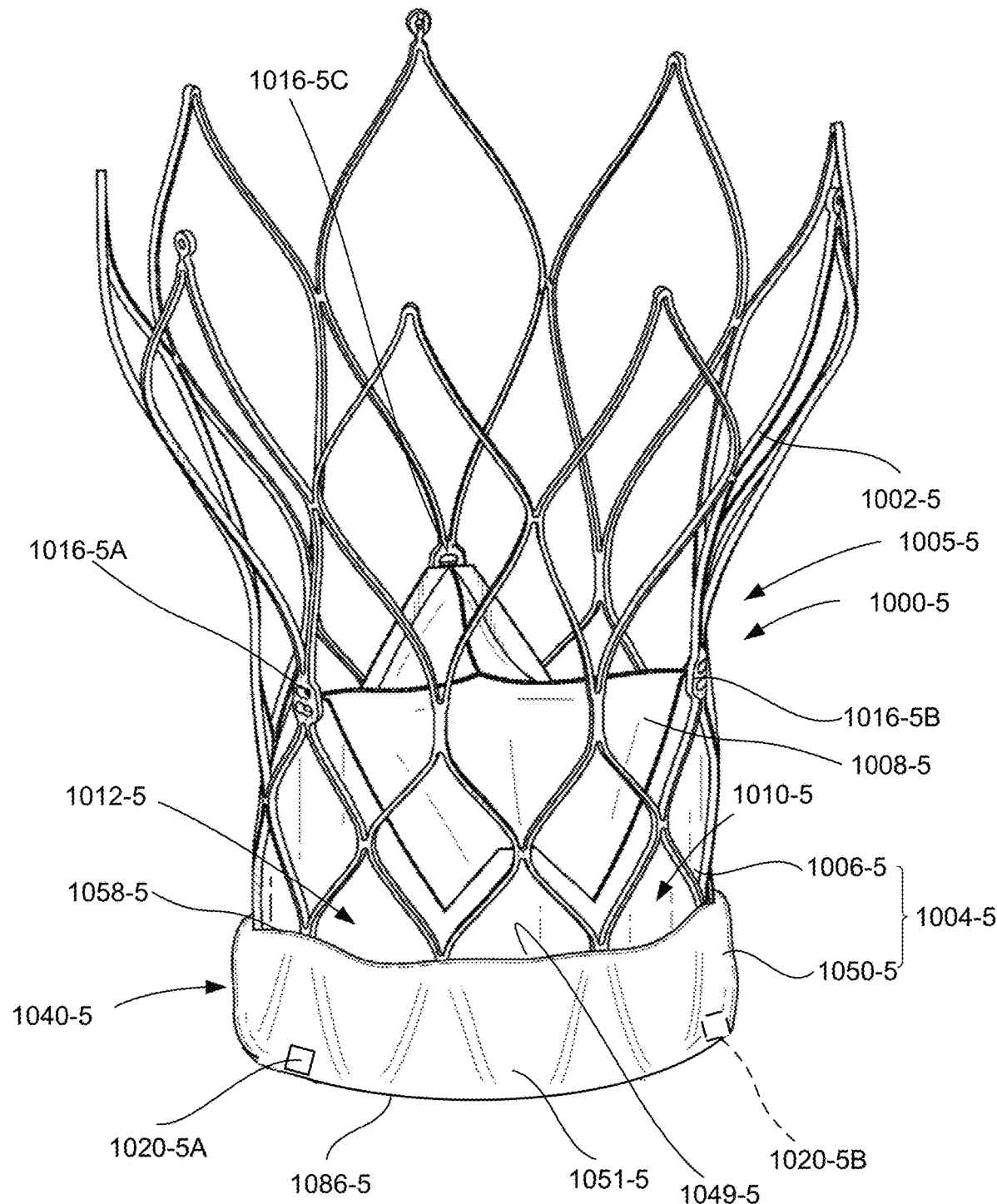
FIG. 11A is a perspective view of a prosthetic heart valve according to an embodiment of the disclosure.
Figure 11B:
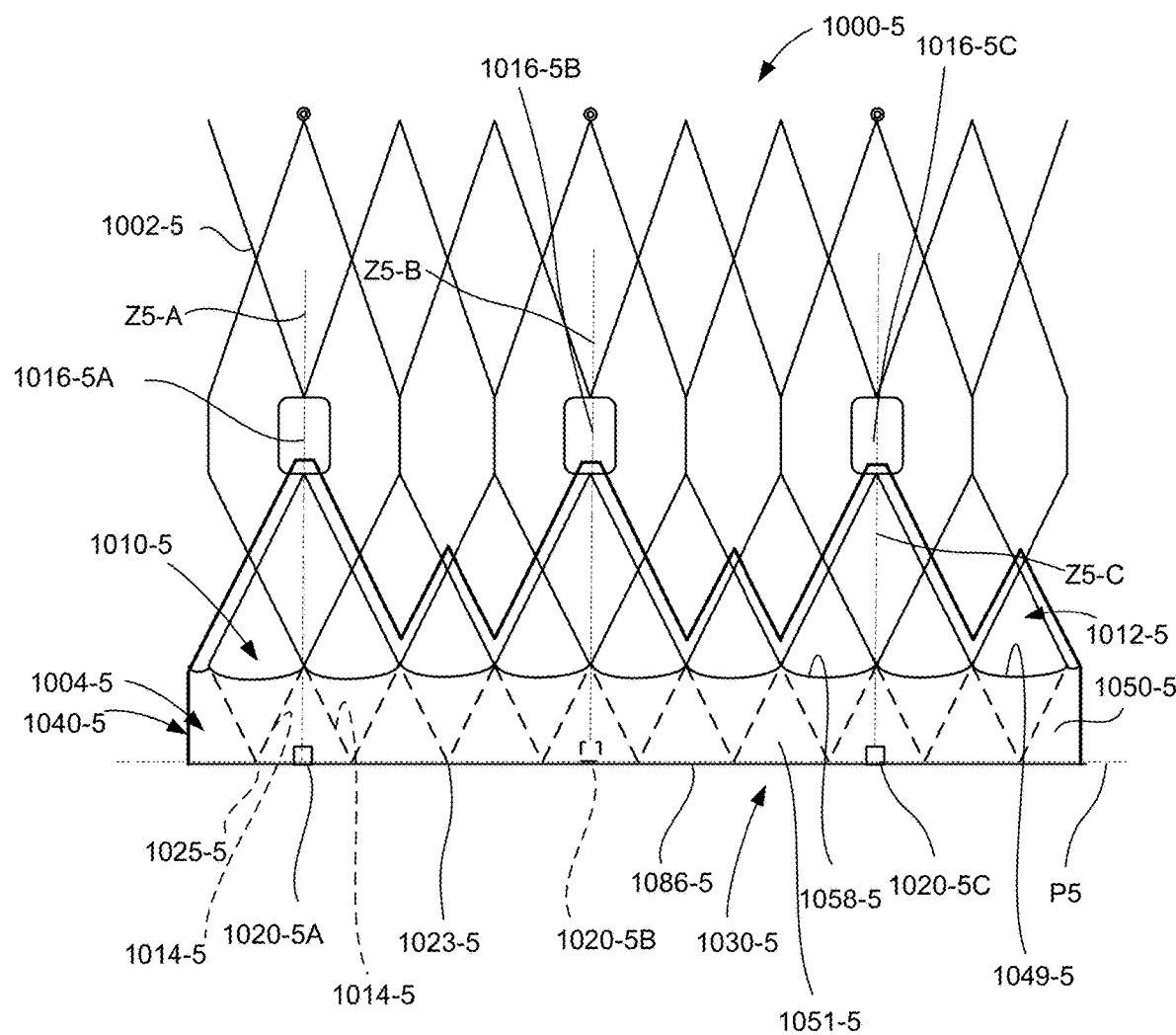
FIG. 11B is a schematic developed view of a stent and cuff as shown in FIG. 11A.

FIGS. 11A-11B show another example stent-supported heart valve 1000-5 with a collapsible stent 1002-5 and valve assembly 1005-5, which is similar to the stent-supported heart valve 1000-4 shown in FIGS. 10A-10B. This heart valve assembly 1000-5 differs from the heart valve 1000-4 in the arrangement of the radiopaque elements on the cuff 1004-5 (formed in this example from the inner cuff 1006-5 and outer cuff 1050-5), as well as in a slight change to the bottom edge of the cuff 1004-5, where the outer cuff 1050-5 wraps around the bottom and tips 1025-5 of the stent 1002-5 in the annulus region 1040-5. In some examples, a portion of the outer cuff 1050-5, such as portions of the edge 1058-5 of the outer cuff, may be attached to stent 1002-5 to form pockets 1010-5 between the inner cuff 1006-5 and outer cuff 1050-5, as previously discussed herein. As best shown in FIG. 11B, bottom edge 1086-5 of cuff 1004-5 extends circumferentially between each lowermost point 1023-5 of inflow end 1030-5 of the stent 1002-5, which, in this example, is at the stent tips 1025-5. The edge 1086-5 of the cuff 1004-5 at the inflow end 1030-5 is further arranged so that it extends circumferentially within the same plane P5 as the stent tips 1025-5. In some examples, where the inner cuff 1006-5 and the outer cuff 1050-5 are formed from two separate pieces of tissue or material, the inner cuff 1006-5 and the outer cuff 1050-5 may be joined together at or adjacent the bottom edge 1086-5.

At least one radiopaque element may be positioned at the bottom edge 1086-5 of the cuff 1004-5 to assist a surgeon in detecting the position of one or more of the inflow end 1030-5, stent tips 1025-5, or edge 1086-5 of the cuff 1004-5 of the prosthetic heart valve 1000-5. In one example, as best shown in FIG. 11B, first, second, and third radiopaque elements 1020-5A, 1020-5B, and 1020-5C are positioned on the outer cuff 1050-5 in the area of the first proximal row of cells 1012-5 in the annulus region 1040-5, and particularly between struts 1014-5 of directly adjacent cells 1012-5 adjacent the edge 1086-5 of the cuff 1004-5. Each of the three radiopaque elements 1020-5A, 1020-5B, 1020-5C is positioned in the same plane P5 as the bottom edge 1086-5 of the cuff 1004-5 and the tips 1025-5 of the stent 1002-5.

At least one radiopaque element may be positioned on the outer surface 1051-5 of outer cuff 1050-5 and/or at least one radiopaque element may be positioned on the interior surface 1049-5 of the outer cuff. For example, first and third radiopaque elements 1020-5A, 1020-5C are shown disposed on the outer surface 1051-5 of the cuff 1050-5 and facing away from a central portion of the prosthetic heart valve 1000-5. Second radiopaque element 1020-5B, shown in broken lines, is disposed on an interior surface of cuff 1050-5, such that the second radiopaque element is positioned below leaflets 1008-5 and faces toward a central portion of the prosthetic heart valve 1000-5. In other examples, all of the radiopaque elements may be disposed on the outer surface 1051-5 of outer cuff 1050-5, or all of the radiopaque elements may be disposed on the interior surface 1049-5 of outer cuff 1050-5. The radiopaque elements can be attached to the cuff 1050-5 using any means.

Additionally or alternatively, the radiopaque elements can be positioned to identify the positions of the commissure attachment features. In this example, radiopaque elements 1020-A, 1020-5B, and 1020-5C may be positioned in vertical alignment with each of the commissure attachment features and, in some examples, may be the only radiopaque elements on the stent-supported heart valve 1000-5. In this example, radiopaque element 1020-5A is aligned with first commissure attachment feature 1016-5A along an axis Z5-A extending through commissure attachment feature 1016-5A, radiopaque element 1020-5B is aligned with second commissure attachment feature 1016-5B along an axis Z5-B extending through commissure attachment feature 1016-5B, and radiopaque element 1020-5C is aligned with third commissure attachment feature 1016-5C along an axis Z5-C extending through third commissure attachment feature 1016-5C. In other examples, the radiopaque elements may be positioned anywhere on the cuff or leaflets, provided the radiopaque elements are vertically aligned or longitudinally aligned with the commissure attachment features. Similarly, one or more of the radiopaque elements 1020-5A, 1020-5B, 1020-5C or additional radiopaque elements may be positioned on the leaflets 1008-5 or stent 1002-5 in alignment with one of the commissure attachment features 1016-5A, 1016-5B, 1016-5C.

Figure 12A:
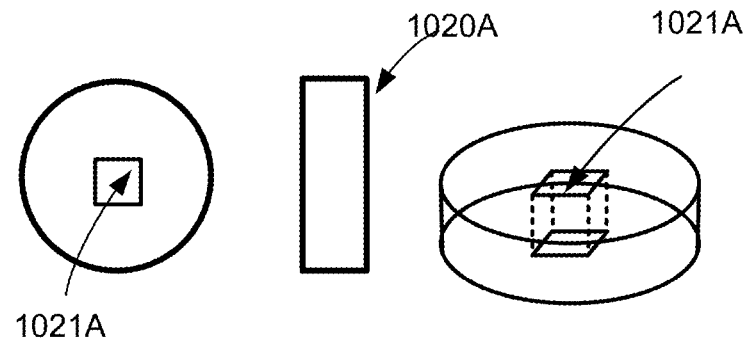
FIGS. 12A-12G are schematic views of example radiopaque elements according to aspects of the disclosure.
Figure 12B:
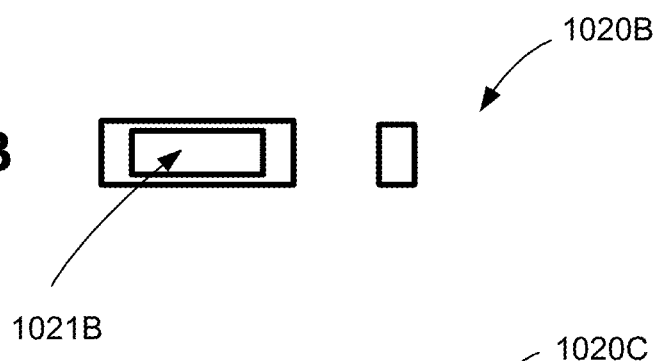
Figure 12C:
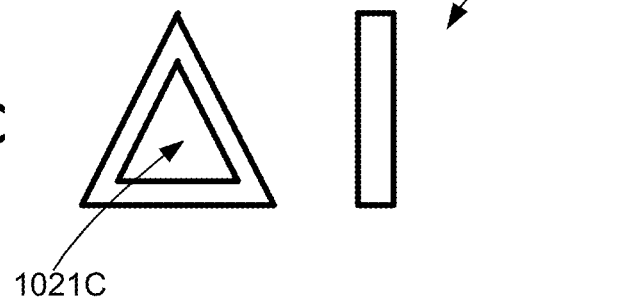
Figure 12D:
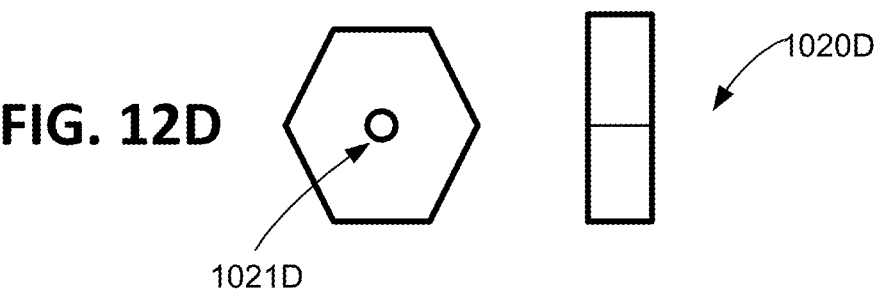

The radiopaque elements can take on any shape, size, or form. FIGS. 12A-12G illustrate a small sampling of possible shapes and sizes the radiopaque elements can embody, but the possibilities are numerous. The radiopaque elements can be pre-formed and attached to desired portions of the prosthetic heart valve. Front, side, and perspective views of a radiopaque element 1020A are shown in FIG. 12A. The radiopaque element 1020A is circular in shape and includes an opening 1021A extending through the thickness of the radiopaque element 1020A. The opening 1021A can have a shape that is the same as or different from the outer peripheral shape of the radiopaque element. In this example, the opening 1021A is in the shape of a square, whereas the outer peripheral shape of the radiopaque element is a circle. As in the previous example, the opening 1021A can provide a means for the radiopaque element to be attached to the prosthetic heart valve, such as by suturing. Radiopaque elements can take on a variety of other shapes, including a rectangular shape such as shown in FIG. 12B (radiopaque element 1020B with a rectangular opening 1021B), a triangular shape such as shown in FIG. 12C (radiopaque element 1020C with a triangular opening 1021C), and a hexagonal shape such as shown in FIG. 12D (radiopaque element 1020D with a circular opening 1021D). In other examples in which the radiopaque element includes an opening, the shape of the opening may differ from the outer peripheral shape of the radiopaque element.

Figure 12E:
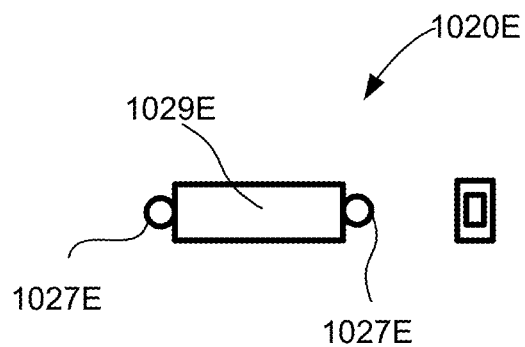
Figure 12F:
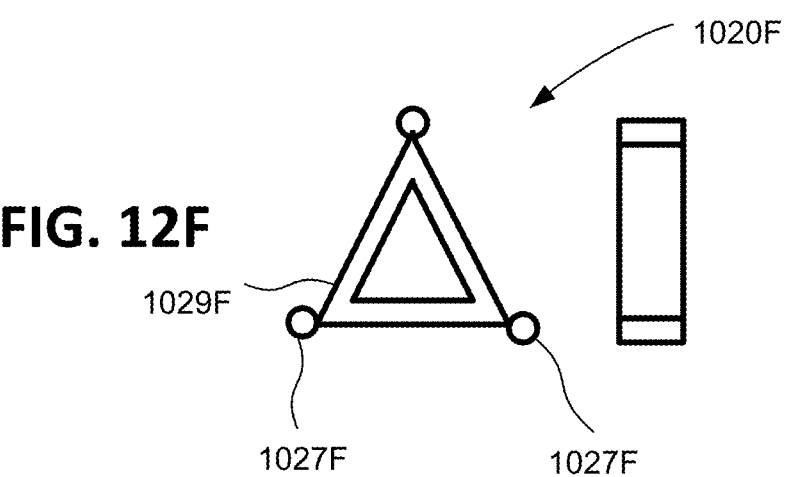
Figure 12G:
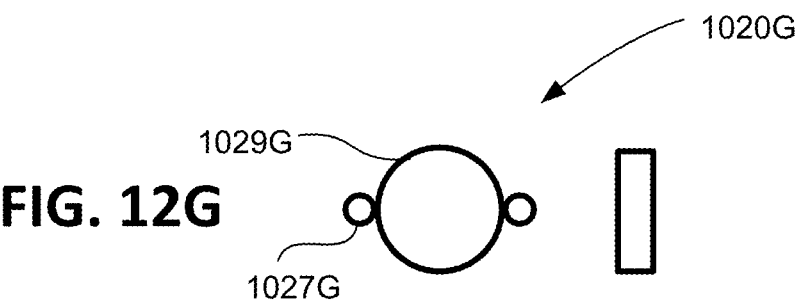

Instead of or in addition to openings extending through a central portion of the radiopaque element, eyelets can be provided adjacent outer edges of the radiopaque element to allow for attachment to the heart valve. For example, the front and side views of radiopaque element 1020E shown in FIG. 12E illustrate eyelets 1027E attached to a rectangular main body 1029E. Eyelets 1027F are also shown attached to the main triangular body 1029F of radiopaque element 1020F in FIG. 12F. Eyelets 1027G are shown attached to the main circular body 1029G of radiopaque element 1020G in FIG. 12G.

Although the radiopaque elements are schematically represented throughout the present disclosure as being square in shape, it is to be appreciated that the radiopaque elements are not limited to a square shape. Further, the radiopaque elements can be formed from one or more radiopaque materials. Moreover, radiopaque elements having different shapes or formed from different materials may be positioned on a single prosthetic valve.

Radiopaque elements may be attached to the cuff, including the inner cuff, the outer cuff, or both the inner and outer cuffs using any known methods or combination of methods. For example, radiopaque elements may be sewn, glued, heat set, pressed, or crimped to fabric or tissue cuffs, or may be attached to the cuffs using any other technique.

Figure 13:
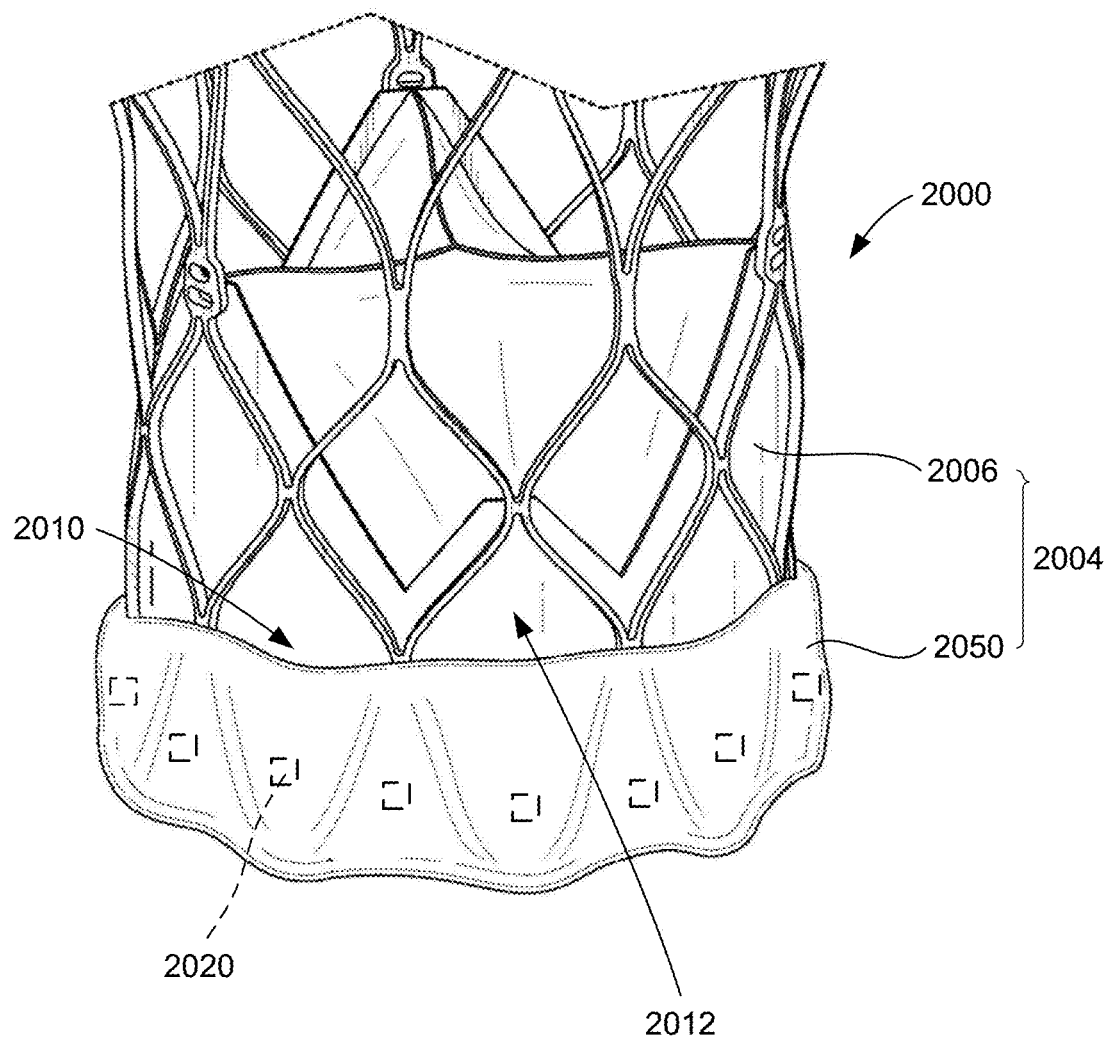
FIG. 13 is an enlarged perspective view of a portion of a prosthetic heart valve according to another embodiment of the disclosure.
Figure 14:
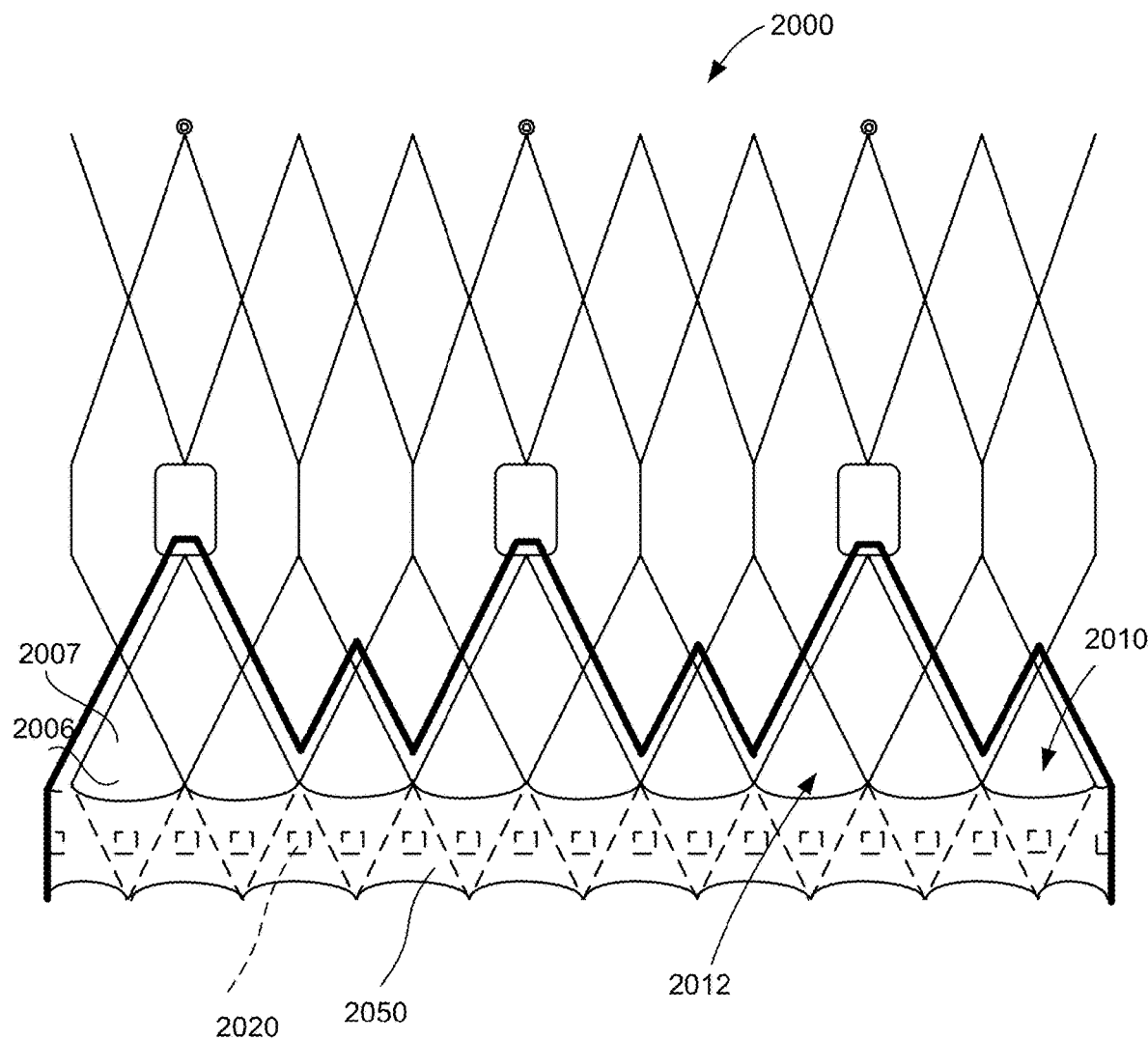
FIG. 14 is a schematic developed view of a stent and cuff having the arrangement of radiopaque elements shown in FIG. 13.
Figure 15:
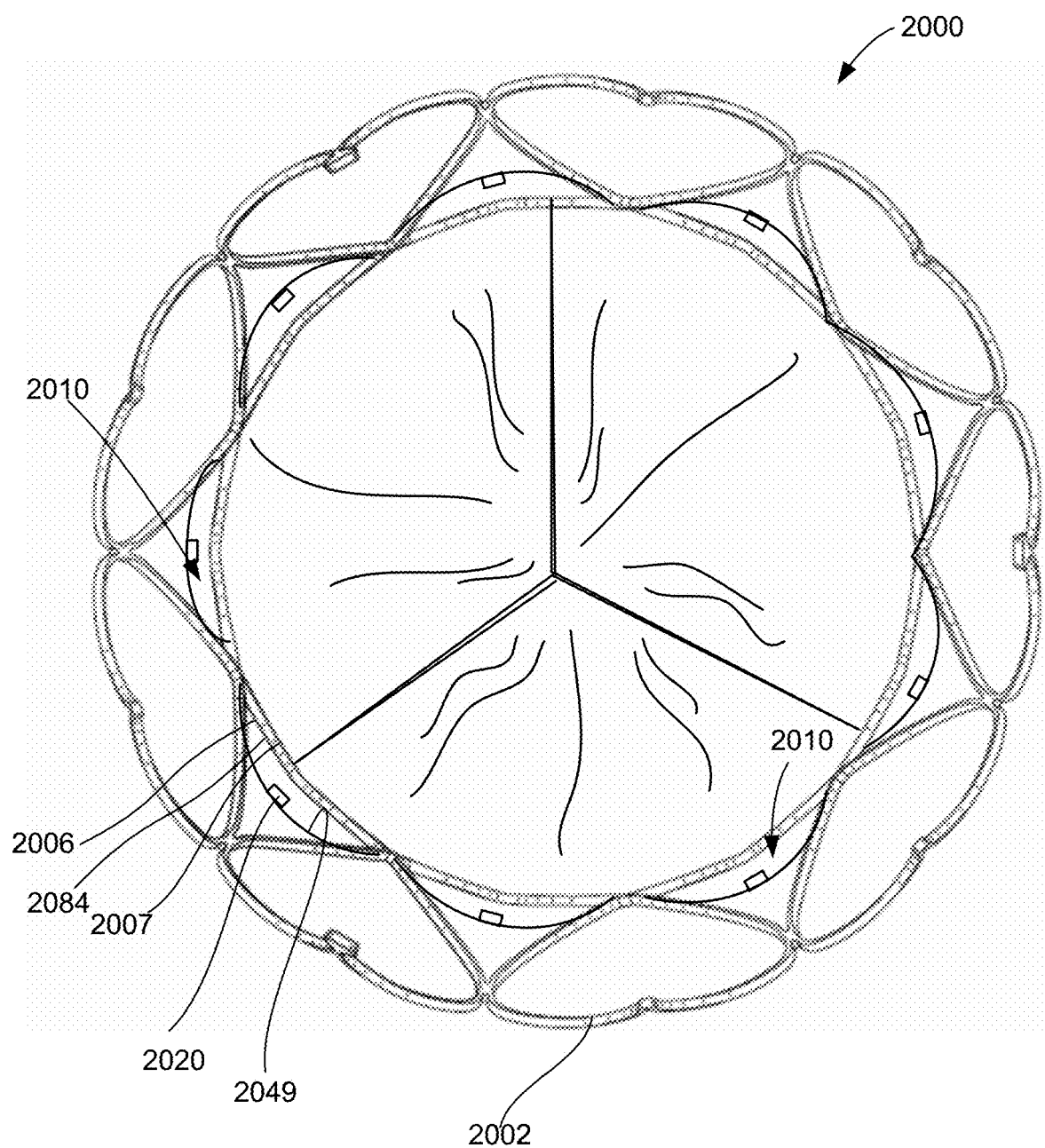
FIG. 15 is a schematic top view of the prosthetic heart valve of FIG. 13.

The radiopaque elements may be attached to any portion of cuff 1004. FIGS. 13-15 illustrate another heart valve 2000 in which radiopaque elements 2020 are disposed on the inner surface of pocket 2010 formed by outer cuff 2050. As in the previous example, radiopaque elements 2020 may be positioned within the cells 2012 in the first proximal row of cells, as well as between directly adjacent cells 2012. With reference to FIG. 15, which is a top view of FIG. 13, radiopaque elements 2020 may be positioned between the inner surface 2049 of outer cuff 2050 and both the outer surface 2007 of the inner cuff 2006 and the abluminal surface 2084 of stent 2002. In this configuration, radiopaque elements 2020 are protected from damage due to their position within the interior portion of pocket 2010.

Figure 16:
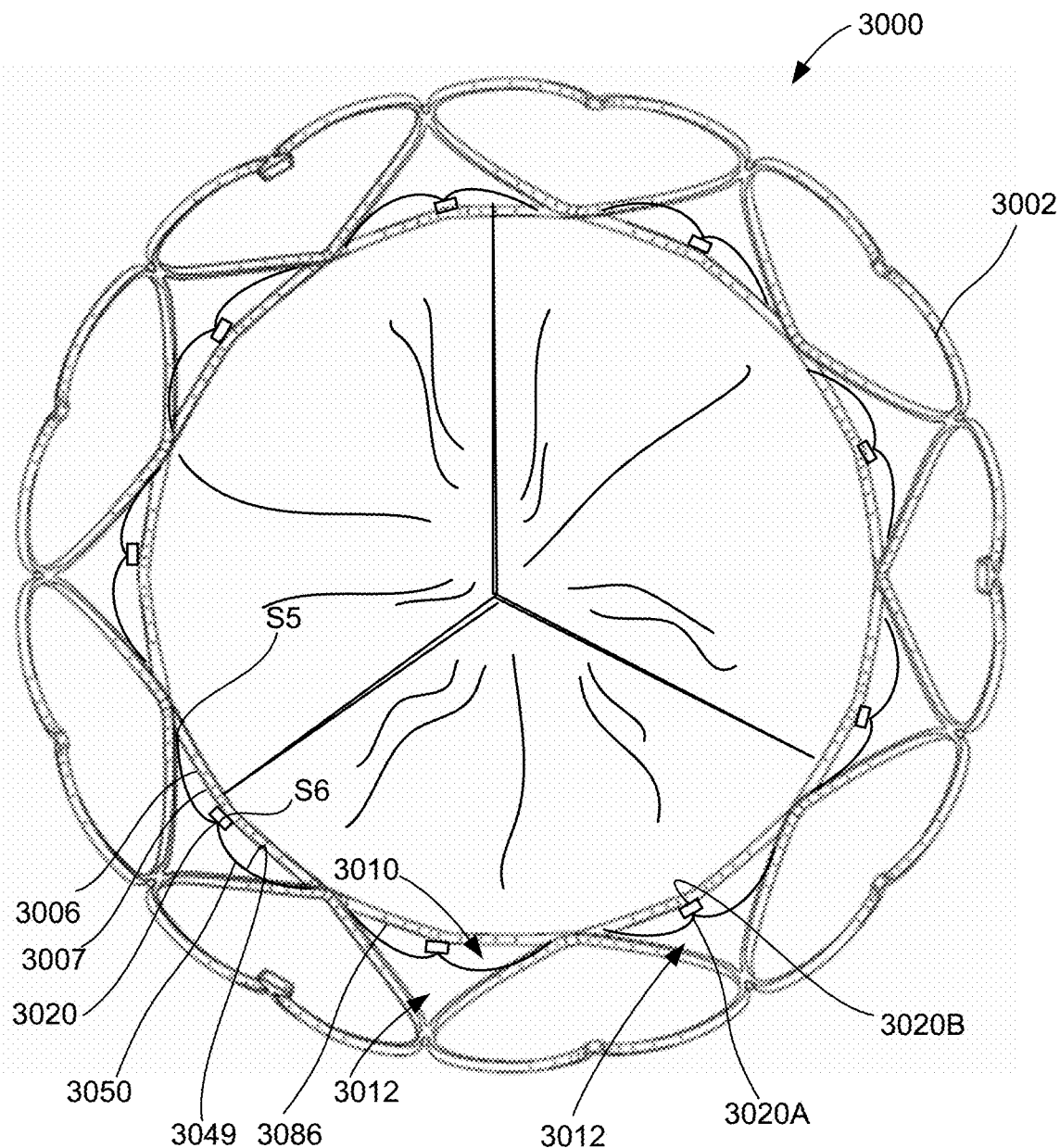
FIG. 16 is a schematic top view of a prosthetic heart valve according to another embodiment of the disclosure.

FIG. 16 shows an alternative top view of a stent-supported heart valve 3000. In this example, radiopaque elements are again positioned within the interior of pocket 3010 formed between the outer cuff 3050 and inner cuff 3006. Each radiopaque element 3020 includes a first surface 3020A that faces toward the inner surface 3049 of outer cuff 3050 and a second surface 3020B that faces toward the outer surface 3007 of inner cuff 3006. This example differs from that of FIGS. 13-15 to the extent that each radiopaque element 3020 is attached to both the outer cuff 3050 and inner cuff 3006, and more particularly, to the interior surface 3049 of outer cuff 3050 and the outer surface 3007 of inner cuff 3006. This in effect creates additional pockets 3010, on opposite lateral sides of each radiopaque element 3020, which are smaller in size and have an attachment point S5 to the stent 3002 and an attachment point S6 to the radiopaque element 3020. This fixes the position of radiopaque elements 3020 within cells 3012 or between adjacent cells 3012. Radiopaque elements 3020 may be attached to the inner cuff 3006 and outer cuff 3050 using any means. For example, each radiopaque element 3020 may be sutured to both inner cuff 3006 and outer cuff 3050 through openings in the radiopaque element, such as central openings or eyelets as discussed in connection with the radiopaque elements shown in FIGS. 12A-12G. Alternatively, or additionally, an adhesive can be provided on the radiopaque element 3020 to secure the radiopaque element to both the inner cuff 3006 and outer cuff 3050.

Figures 16A, 16B:
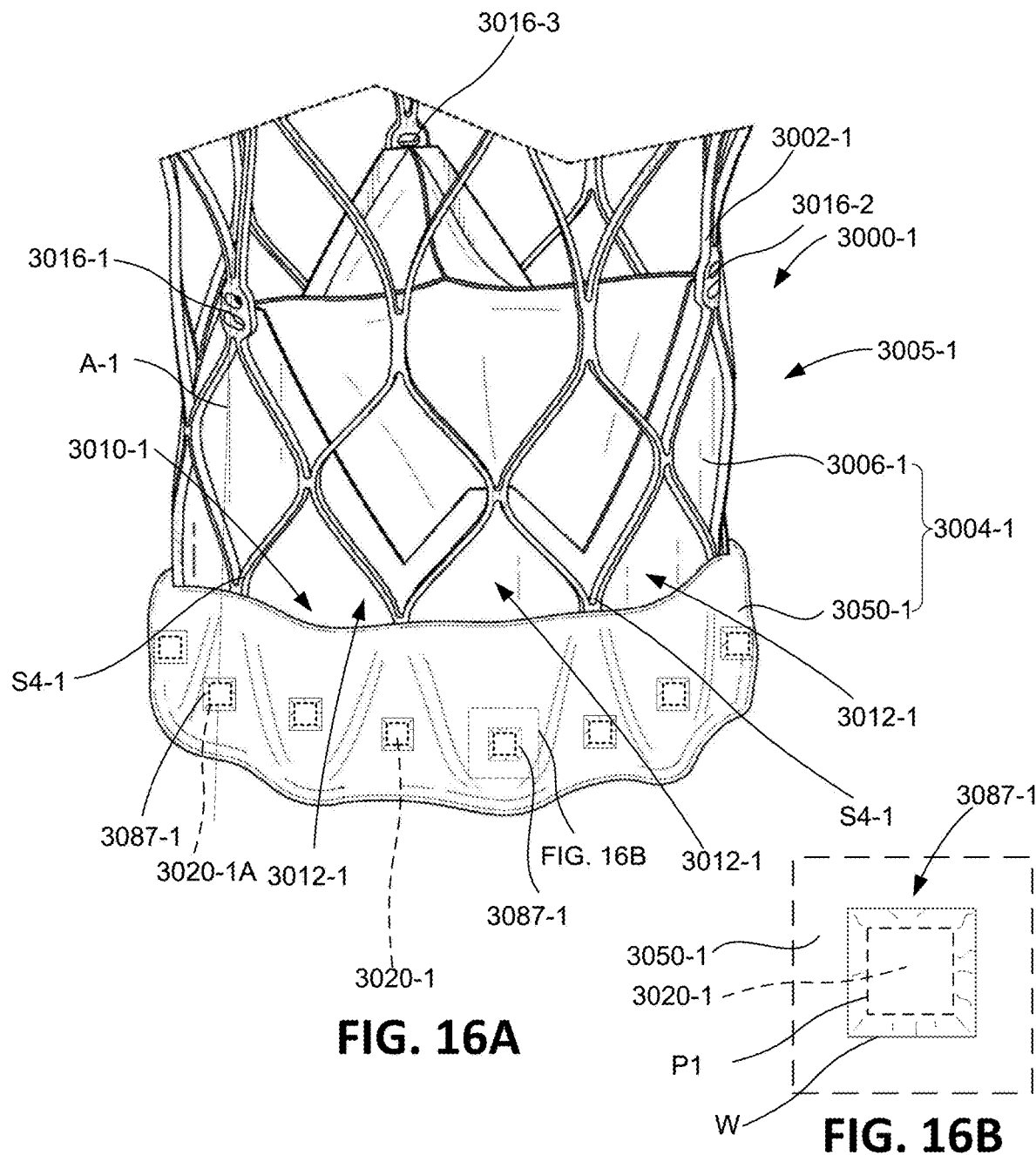
FIG. 16A is an enlarged perspective view of a portion of a prosthetic heart valve according to an embodiment of the disclosure.
FIG. 16B is an enlarged portion of FIG. 16A.

FIG. 16A illustrates another example of at least one radiopaque element positioned between the inner cuff 3006-1 and the outer cuff 3050-1 of the cuff 3004-1 of a stent-supported heart valve 3000-1. As shown, each radiopaque element 3020-1 may be secured to the heart valve assembly 3005-1 within a receiving pocket 3087-1 formed by the joinder of the inner cuff 3006-1 and the outer cuff 3050-1 around at least portions of the radiopaque element 3020-1.

Figure 16C:
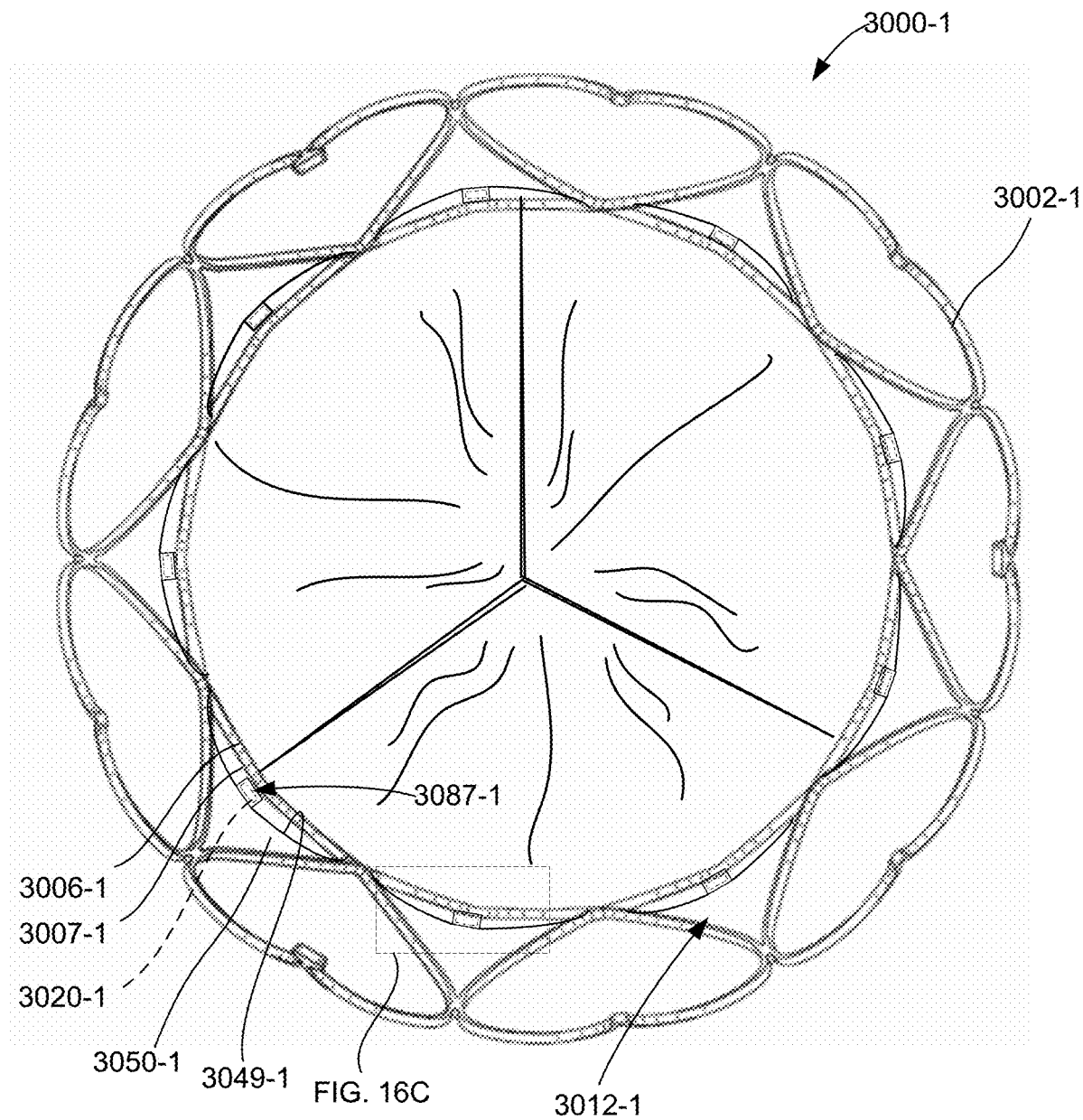
FIG. 16C is a schematic top view of a prosthetic heart valve according to another embodiment of the disclosure.
Figure 16D:
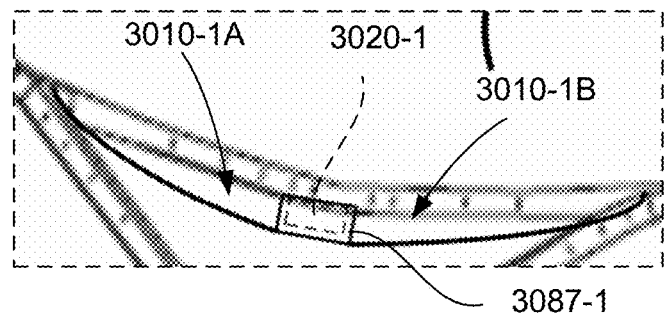
FIG. 16D is an enlarged view of a portion of the prosthetic heart valve shown in FIG. 16C.

As shown in FIG. 16A and discussed in previous examples, the outer cuff 3050-1 can be attached to the stent at points S4-1, located where each cell 3012-1 in the proximal-most row of cells intersects with an adjacent cell 3012-1 in that same row. As shown in FIG. 16D, an enlarged portion of FIG. 16C, this in effect creates a first open pocket 3010-1A positioned on one side of each receiving pocket 3087-1 and a second open receiving pocket 3010-1B positioned on the opposite side of each receiving pocket 3087-1.

In accordance with aspects of the disclosure, the outer cuff 3050-1 and inner cuff 3006-1 can be coupled together to form a receiving pocket 3087-1 for securing a radiopaque element 3020-1 therein using any means, including suturing, ultrasonic welding, melting, gluing, riveting, snapping, or any combination of two or more methods. In one example, the outer cuff 3050-1 and inner cuff 3006-1 can be coupled together through welding, such as ultrasonic welding. Ultrasonic welding uses an ultrasonic signal to cause the material to vibrate. This transfers energy into the material and friction due to the resulting vibration causes the material to heat. When this occurs, two materials will melt together at their interface, thereby forming a weld.

In some embodiments, the outer surface 3007-1 of inner cuff 3006-1 and the interior surface 3049-1 of outer cuff 3050-1 can be ultrasonically welded together around the radiopaque element 3020-1 to form the receiving pocket 3087-1. When the inner cuff 3006-1 and the outer cuff 3050-1 vibrate at their interface due to ultrasonic vibrations from the welding tool, the inner cuff 3006-1 and the outer cuff 3050-1 will melt and become welded together at their interface. In some examples, the inner cuff 3006-1 and outer cuff 3050-1 may be formed of the same materials, including any suitable biological material or polymer such as, for example, polytetrafluoroethylene (PTFE), ultra-high molecular weight polyethylene (UHMWPE), polyurethane, polyvinyl alcohol, silicone, or combinations thereof. When formed from the same or similar materials, the inner cuff 3006-1 and outer cuff 3050-1 will have similar melting points, which can facilitate the welding process. In still other examples, an intermediate material may be provided between the inner cuff 3006-1 and the outer cuff 3050-1 to further facilitate ultrasonic welding. In one example where both the inner cuff 3006-1 and outer cuff 3050-1 are formed from UHMWPE, a polyester material can be provided between the inner cuff 3006-1 and outer cuff 3050-1 that will be ultrasonically welded with the inner cuff 3006-1 and outer cuff 3050-1.

As shown in FIG. 16B, an enlarged portion of FIG. 16A, a weld line W is shown on the outer cuff 3050-1 extending around an outer periphery P1 of the radiopaque element 3020-1 to form the pocket 3087-1. The weld line W shows where the inner cuff 3006-1 and the outer cuff 3050-1 are welded together. In this example, the radiopaque element 3020-1 is in the shape of a square and the weld line W has a complementary square shape. But in other examples, the weld line W can take any shape as it extends around all or a portion of the edges of the radiopaque element 3020-1. For example, the weld line W may be in the shape of a circle or a semi-circle. The weld line W can therefore match the shape of the radiopaque element 3020-1 or differ from the shape of the radiopaque element 3020-1.

Figure 16E:
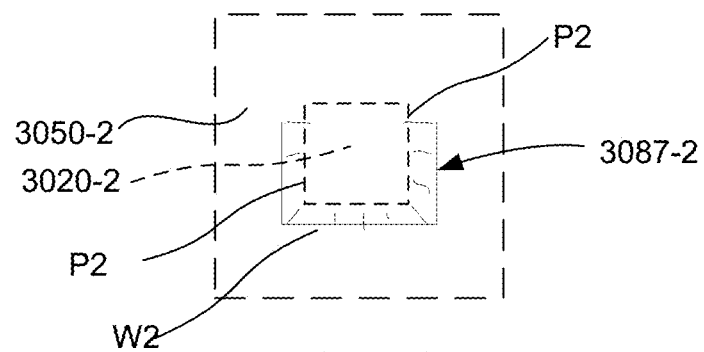
FIG. 16E is an alternative example of a receiving pocket.

In some examples, the weld line W may extend around only a portion of the periphery P1 of the radiopaque element 3020-1, such that the inner cuff 3006-1 and the outer cuff 3050-1 are welded together around only a portion or portions of the radiopaque element 3020-1. For example, a series of spot welds can be employed that are sufficient to secure the radiopaque element 3020-1 within the receiving pocket 3087-1, but that do not extend in one continuous weld line around the entire periphery P1 of the radiopaque element 3020-1. In still other examples, the welded portions may extend around less than the entire periphery P1 of the radiopaque element 3020-1 so as to form an open pocket. For example, as shown in FIG. 16E, an alternative weld line W2 extends around only a portion of the periphery P2 of the radiopaque element 3020-2, and particularly only around three edges of the radiopaque element 3020-2. This creates an open receiving pocket 3087-2 between the inner cuff (not shown) and the outer cuff 3050-2. Sutures or an adhesive may be used to join the outer cuff 3050-2 and inner cuff together to close or seal off the open portion of the pocket 3087-2. Alternatively, the receiving pocket 3087-2 can remain open and an adhesive or suture may be applied directly to the radiopaque element 3020-2, including through an opening in the radiopaque element or all around the periphery of the radiopaque element, to ensure that the radiopaque element 3020-2 is secured within the open receiving pocket 3087-2. Further, depending on the method of formation, the radiopaque element 3020-2 can be positioned within the pocket 3087-2 after formation of the open receiving pocket 3087-2. Once the radiopaque element 3020-2 is inserted within the open receiving pocket 3087-2, further ultrasonic welding can be implemented to close the pocket 3087-2. Thus, the radiopaque element 3020-1, 3020-2 can be secured within the pocket due to the formation of a weld line that extends around the entirety or less than the entirety of the periphery P1 of the radiopaque element 3020-1, 3020-2, or in other examples, by additional attachment techniques, such as sutures or adhesives.

In one example of receiving pocket formation, the inner cuff 3006-1 can be attached to the stent 3002-1 and the outer cuff 3050-1 can be attached to the stent 3002-1 at points S4-1 so that the open pockets 3010-1 are formed prior to the attachment of the radiopaque elements to the valve assembly 3005-1. The radiopaque element 3020-1 can first be positioned within each pocket 3010-1 on a desired portion of the inner cuff 3006-1. An adhesive can optionally be used to hold the radiopaque element 3020-1 on the inner cuff 3006-1 so as to prevent the radiopaque element from moving during welding. The outer cuff 3050-1 can then be positioned so that the interior surface 3049-1 of the outer cuff 3050-1 covers the exposed surface of the radiopaque element 3020-1. In such arrangement, the radiopaque element 3020-1 is positioned between the inner cuff 3006-1 and the outer cuff 3050-1. A welding tool can then be used to create a weld line W that extends around the outer periphery P1 of the radiopaque element 3020-1 and welds the inner cuff 3006-1 and outer cuff 3050-1 together. This creates and forms the receiving pocket 3087-1 between the inner cuff 3006-1 and outer cuff 3050-1 for containing the radiopaque element 3020-1. This also forms smaller pockets 3010-1A and 3010-1B. In other examples, the outer cuff 3050-1 is not attached to the stent 3002-1 prior to formation of the receiving pocket 3087-1. Instead, the outer cuff 3050-1 may be attached to the stent at, for example, points S4-1 after formation of the receiving pockets 3087-1.

In some examples, the ultrasonic weld may extend directly adjacent the edges of the radiopaque element so that the radiopaque element does not move within the pocket 3087-1. In other examples, the weld may be spaced further apart from at least one edge or the continuous edge of the radiopaque element such that the radiopaque element 3020-1 has some clearance to move within the pocket 3087-1.

The welding tool may be any tool configured to transmit heat or signals that generate heat. For example, the welding tool may transmit an ultrasonic signal that can vibrate the fabric and cause friction between the inner cuff 3006-1 and the outer cuff 3050-1. The friction created between the inner cuff 3006-1 and the outer cuff 3050-1 concurrently melts the inner cuff 3006-1 and outer cuff 3060-1, bonding them together. When cooled, the inner cuff 3006-1 and outer cuff 3050-1 have melted together, forming the weld and weld line W. Ultrasonic welders are available from many companies, including Branson Ultrasonic Corp. and Dukane Corp.

In one example, the horn of the ultrasonic welder may have an end in the shape of a square, which is configured to make weld line W at once around the entire circumference of the radiopaque element 3020-1. This allows the weld line W to be formed in a single step. Alternatively, a different shaped end may be utilized, such as a circle. In one example, the weld line W is formed by applying an ultrasonic signal of about 15 kHz to about 45 Hz and a signal strength output of about 150 watts to about 3300 watts for between about 1 second and about 30 seconds.

In some examples, at least one of the radiopaque elements secured within a receiving pocket may be aligned with at least one commissure attachment feature. As shown in FIG. 16A, at least radiopaque element 3020-1A can be aligned with commissure attachment feature 3016-1. In this example, radiopaque element 3020-1A, which is positioned within receiving pocket 3087-1, and commissure attachment feature 3016-1 are centrally aligned along axis A-1. In other examples, radiopaque element 3020-1A and commissure attachment feature 3016-1 are not centrally aligned, but are generally aligned with one another along axis A-1. In still other examples, each commissure attachment feature of the prosthetic heart valve, such as commissure attachment features 3016-1, 3016-2, and 3016-3, can be aligned with a corresponding radiopaque element positioned within a receiving pocket. In yet other examples, the prosthetic heart valve includes radiopaque elements provided only within receiving pockets that are aligned with commissure attachment features. The example receiving pockets disclosed herein can be formed according to numerous alternative techniques. In one example, instead of welding, the inner cuff and outer cuff may be joined together by an adhesive around some or all of the periphery P1 of the radiopaque element or by suturing the inner cuff and outer cuff together around the periphery P1 of the radiopaque element. In another example, a weld may be used to first form an open receiving pocket into which a radiopaque element can be inserted. The opening of the receiving pocket can then be sealed by additional ultrasonic welding or by using sutures or an adhesive to close the opening and secure the radiopaque element within the receiving pocket.

Figure 16F:
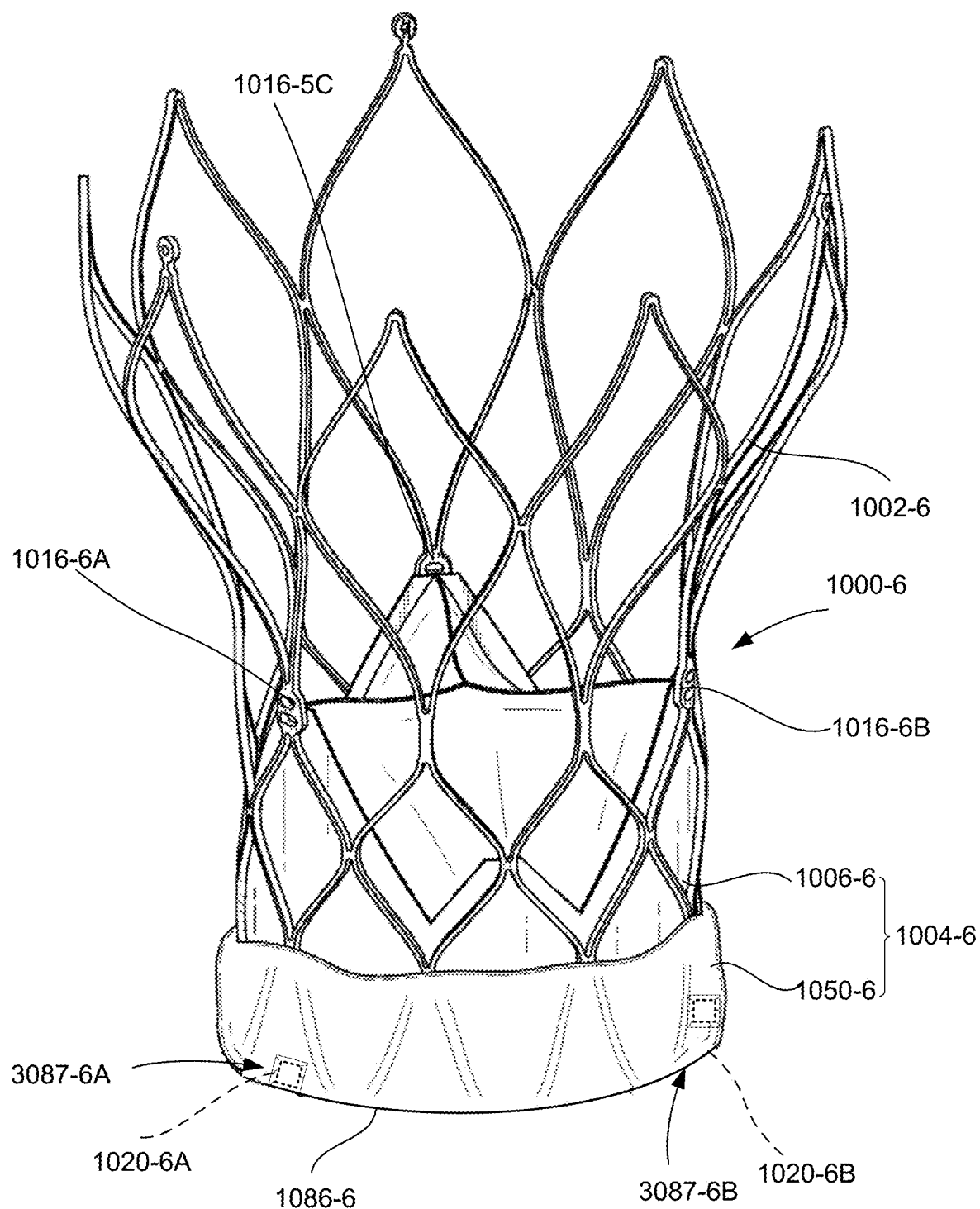
FIG. 16F is a perspective view of a prosthetic heart valve according to an embodiment of the disclosure.
Figure 16G:
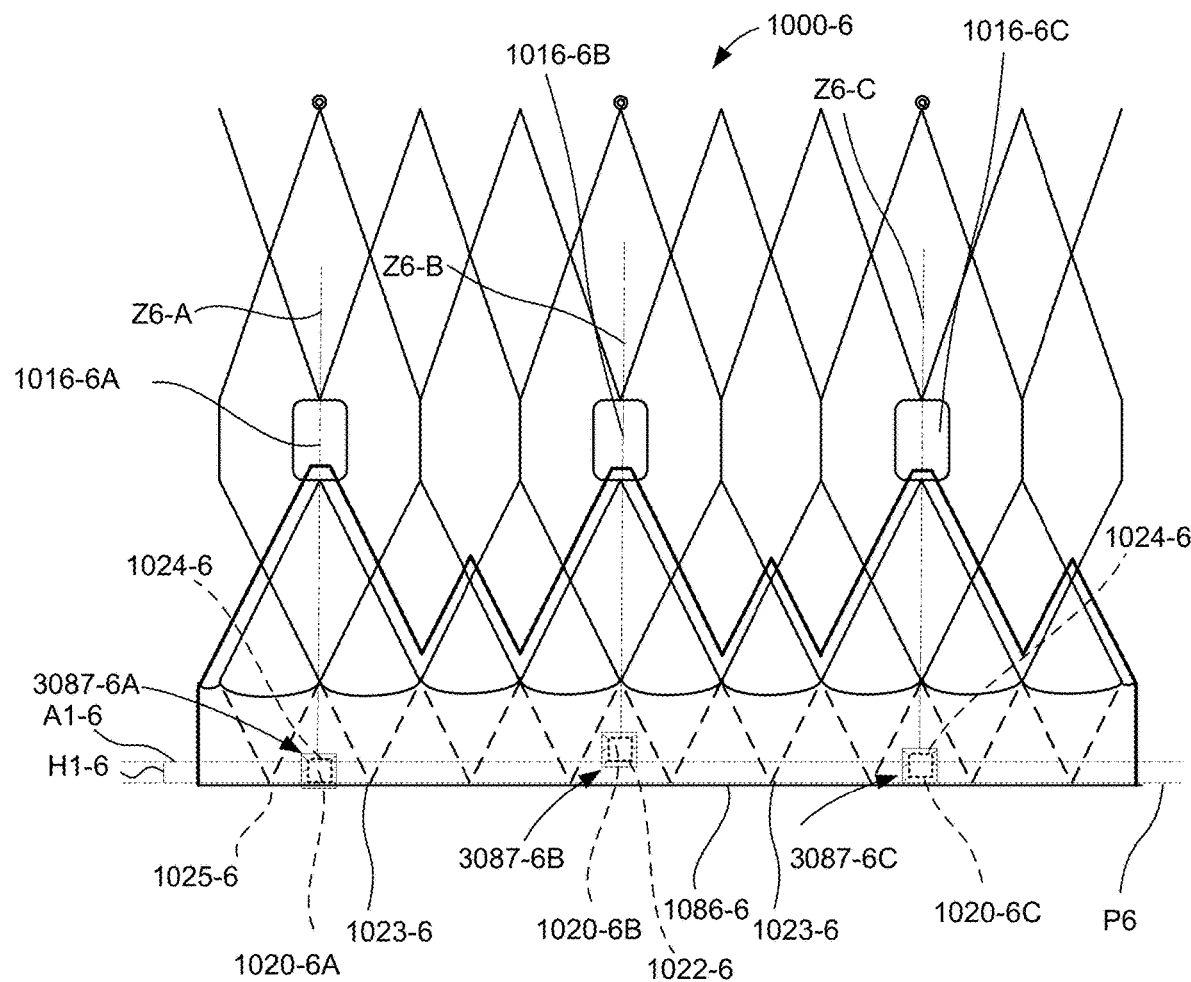
FIG. 16G is a schematic developed view of a stent and cuff as shown in FIG. 16F.

In an alternative configuration, at least one receiving pocket with a radiopaque element therein may be aligned along a bottom edge of the cuff. As shown in FIGS. 16F-16G, a prosthetic heart valve 1000-6 is otherwise identical to the prosthetic heart valve 1000-5 in FIGS. 11A-11B and includes similar reference numerals. The only difference is the location of the radiopaque elements both within receiving pockets, as discussed with regard to FIGS. 16A-16E, as well as along an edge surface of the cuff 1004-6. Cuff 1004-6 includes an edge 1086-6 that lies within a plane P6 in which the tips 1025-6 of the stent 1002-6 also lie. Receiving pockets 3087-6A, 3087-6B, 3087-6C, which contain respective radiopaque elements 1020-6A, 1020-6B, and 1020-6C, can be formed by the joinder of the outer cuff 1050-6 to the inner cuff 1006-6. The receiving pockets can be formed using any means, including those disclosed herein, such as suturing, welding, adhesion, or any combination of these and other methods.

Additionally or alternatively, one or more of the commissure attachment features may be aligned with a receiving pocket and radiopaque element along a longitudinal axis extending through any portion of the commissure attachment feature. In this example, all of the commissure attachment features are vertically aligned with a corresponding receiving pocket. As best shown in FIG. 16G, first commissure attachment feature 1016-6A is aligned with receiving pocket 3087-6A and radiopaque element 1020-6A along an axis Z6-A that extends through commissure attachment feature 1016-6A; second commissure attachment feature 1016-6B is aligned with receiving pocket 3087-6B and radiopaque element 1020-6B along an axis Z6-B that extends through commissure attachment feature 1016-6B; and third commissure attachment feature 1016-6C is aligned with receiving pocket 3087-6C and radiopaque element 1020-6C along an axis Z6-C extending through third commissure attachment feature 1016-6C.

Additionally or alternatively, the top edge or bottom edge of one or more radiopaque elements may be positioned a preset distance away from the inflow edge of stent 1002-6. For example, reference line A1-6 extends along a top edge 1024-6 of respective radiopaque elements 1020-6A and 1020-6C, as well as along a bottom edge 1022-6 of radiopaque element 1020-6B. Reference line A1-6 may be positioned a distance H1-6 away from plane P6 defined by the lowermost points 1023-6 of inflow end of the stent 1002-6. The distance H1-6 can vary, but can be set, for example, at 3 mm from the very edge of the implant represented by plane P6 to aid the user in positioning the implant at a 3 mm target depth. In this example, to achieve the appropriate distance away from the bottom edge 1086-6 of cuff 1004-6, a radiopaque element may be selected with a height of the desired distance away from the inflow edge 1086-6, such that the radiopaque element can be positioned with its bottom edge along the bottom edge 1086-6 of the cuff, and the top edge of the radiopaque element can be the reference point for positioning the implant. In other examples, only two radiopaque elements may have at least one edge aligned with one another, or none of the upper or lower edges of the radiopaque elements 1020-6A, 1020-6B, 1020-6C may be aligned with one another.

Figure 17:
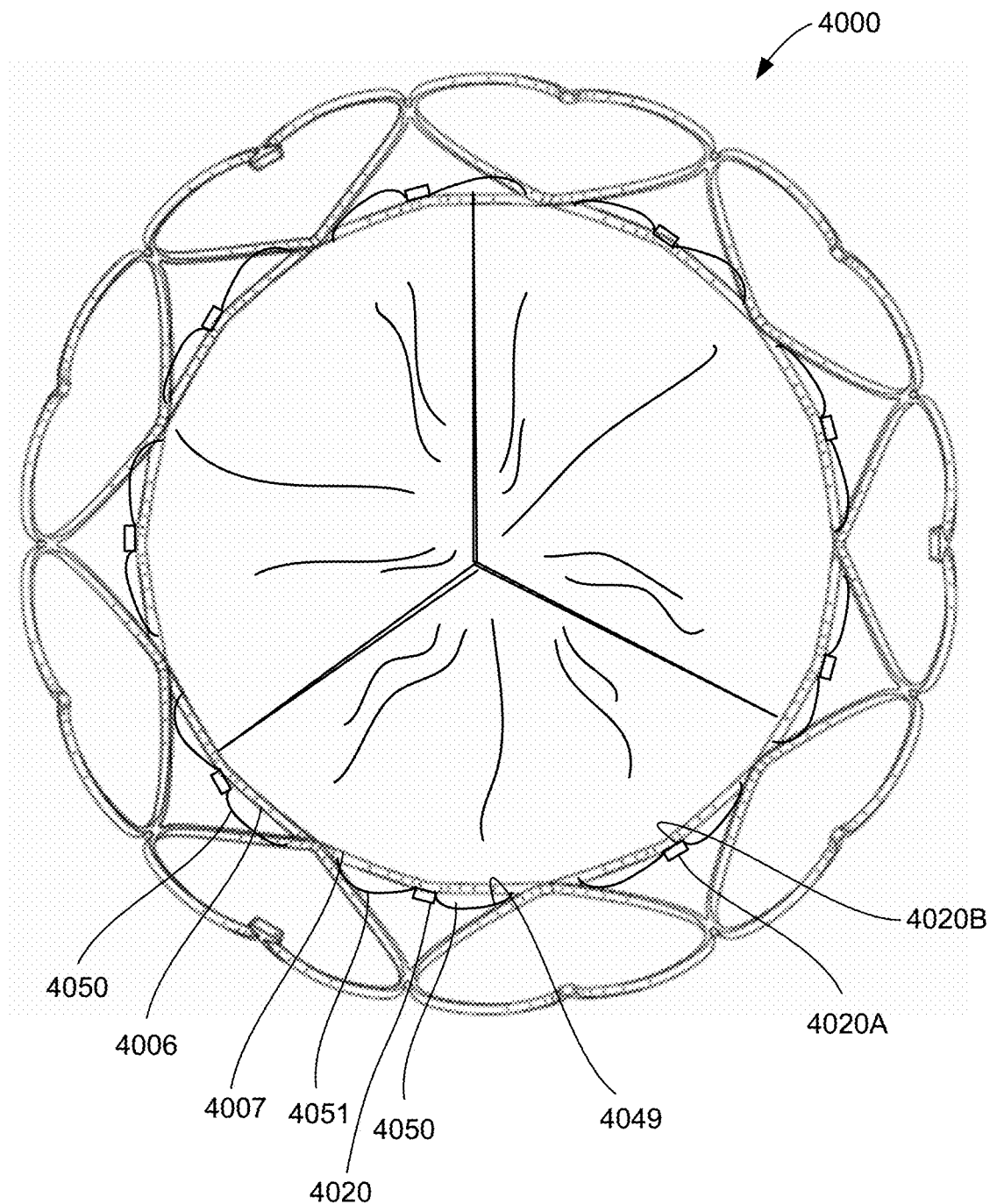
FIG. 17 is a schematic top view of a prosthetic heart valve according to another embodiment of the disclosure.

FIG. 17 shows another example stent-supported heart valve 4000 with radiopaque elements 4020 attached to both the inner cuff 4006 and outer cuff 4050. Radiopaque elements 4020, however, may have an exposed first surface 4020A and a second surface 4020B facing toward the outer surface 4051 of outer cuff 4050. Radiopaque elements 4020 are attached to the outer surface 4051 of outer cuff 4050, such that the interior surface 4049 of outer cuff 4050 is positioned directly adjacent and in contact with the outer surface 4007 of inner cuff 4006. In this configuration, radiopaque elements 4020 will be exposed on the exterior surface of heart valve 4000, but will be attached to both the inner cuff 4006 and outer cuff 4050. In some embodiments of this example and as previously disclosed, at least one radiopaque element may be aligned with a commissure attachment feature (not shown) along a longitudinal axis extending through the commissure attachment feature.

Figure 18:
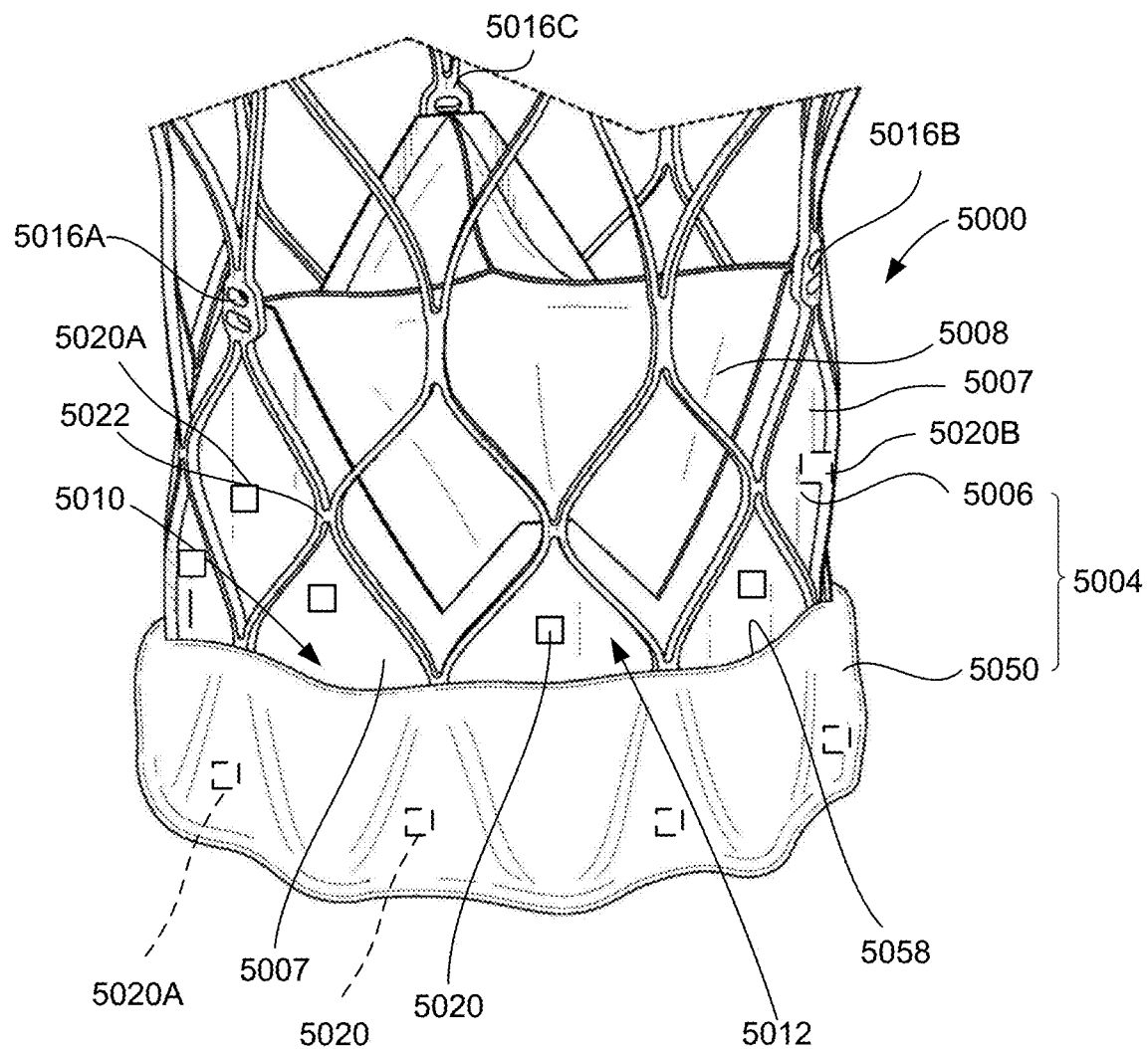
FIG. 18 is an enlarged perspective view of a portion of a prosthetic heart valve according to another embodiment of the disclosure.
Figure 19:
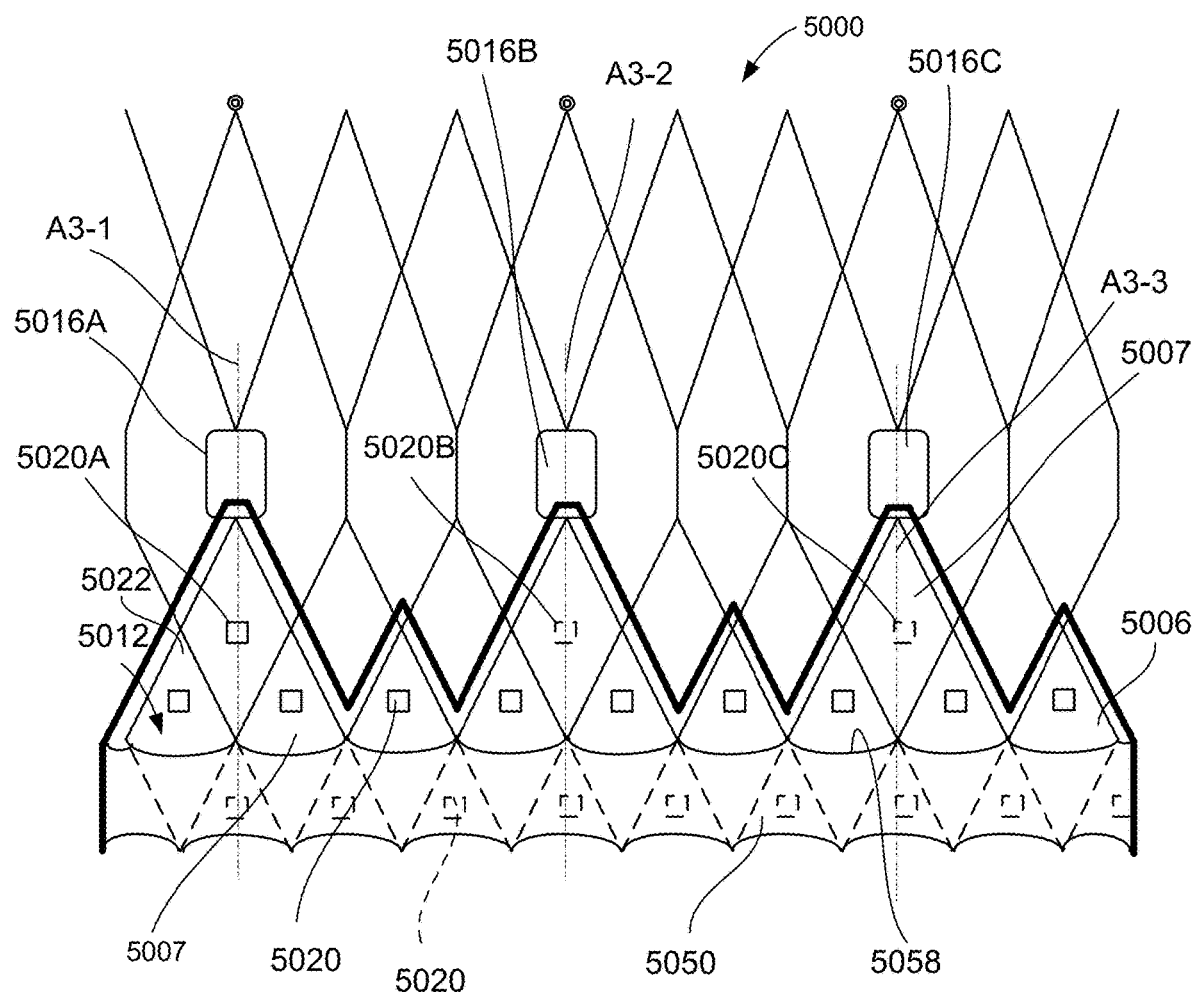
FIG. 19 is a schematic developed view of a stent and cuff having the arrangement of radiopaque elements shown in FIG. 18.
Figure 20:
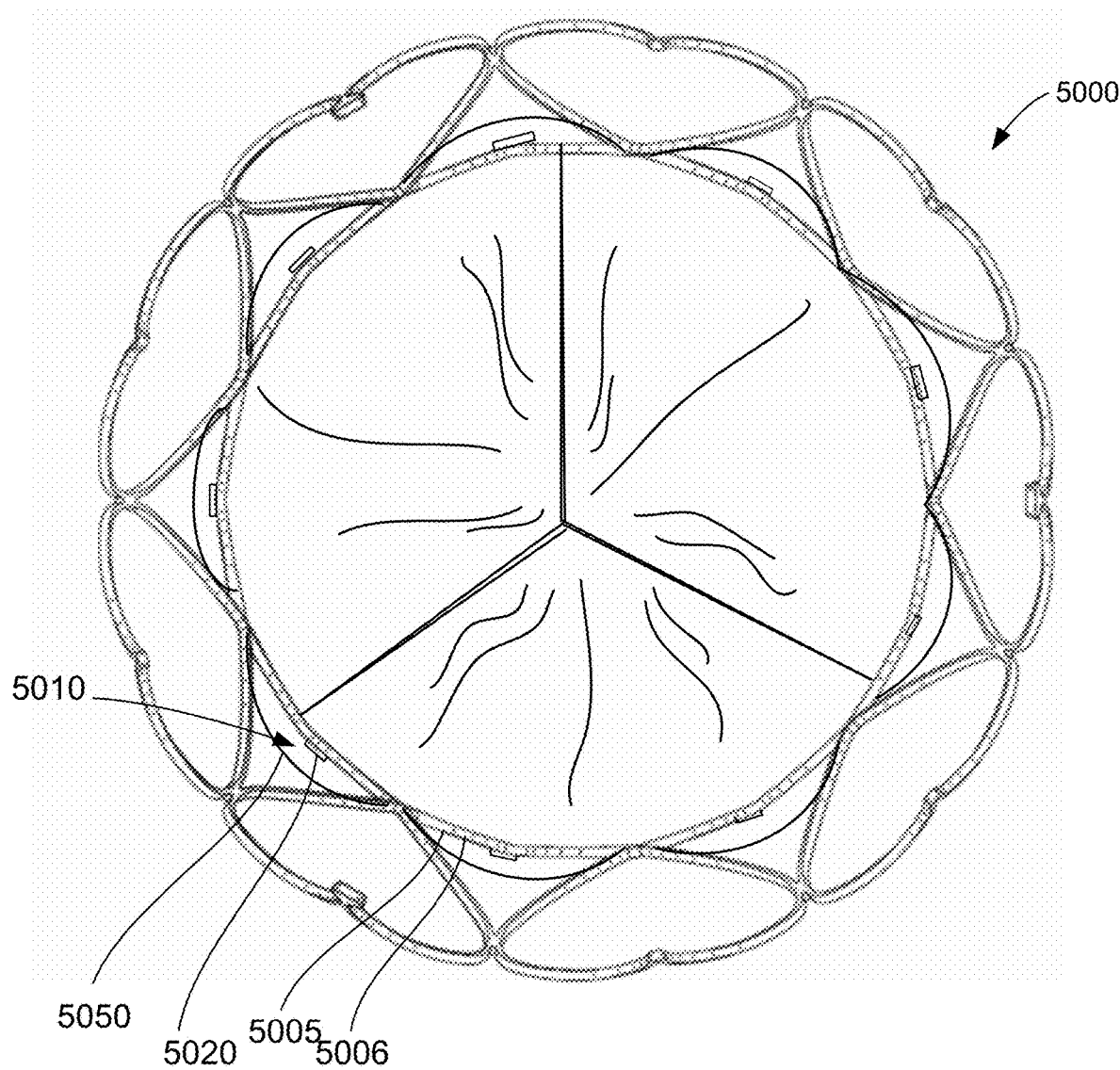
FIG. 20 is a schematic top view of the prosthetic heart valve according to FIG. 18.
Figure 21:
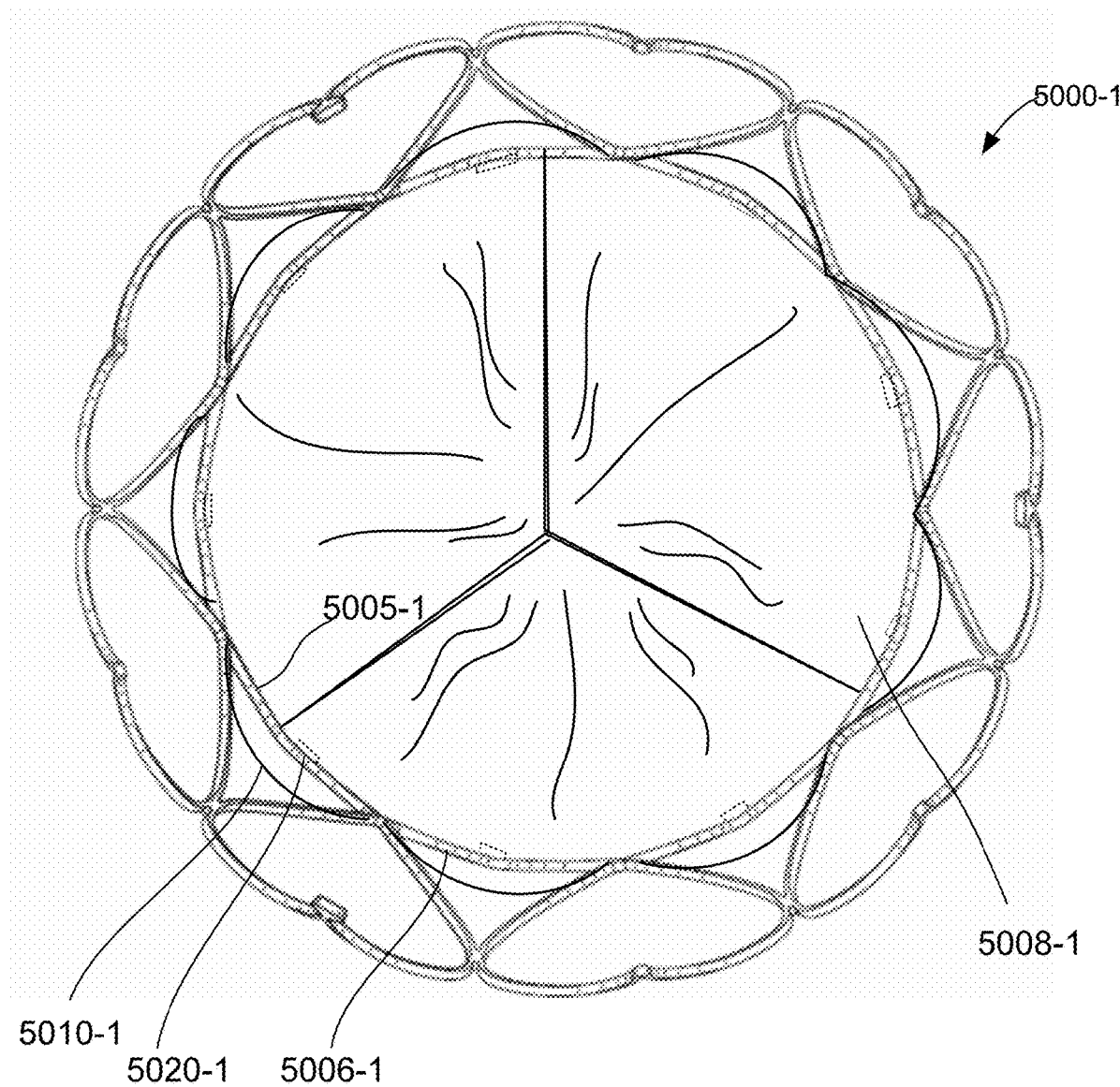
FIG. 21 is a schematic top view of a prosthetic heart valve according to another embodiment of the disclosure.

Radiopaque elements may also be attached to the inner cuff. Another example stent-supported heart valve 5000 is shown in FIGS. 18-20, in which radiopaque elements 5020 are attached to the outer surface 5007 of inner cuff 5006. Some of the radiopaque elements 5020 are shown positioned toward the distal apex 5022 of cells 5012, such that they are exposed beyond the distal edge 5058 of outer cuff 5050. Other radiopaque elements 5020 are shown positioned within pockets 5010, but are also attached to the outer surface 5007 of inner cuff 5006, and are shown in broken lines. Radiopaque elements 5020B and 5020C are shown attached to an interior surface 5005 of inner cuff 5006, and are represented in broken lines to reflect that they are positioned within a central interior portion of heart valve 5000 and underlie leaflets 5008. Similarly, as shown in the example stent 5000-1 of FIG. 21, radiopaque elements 5020-1 are shown attached to the interior surface 5005-1 of inner cuff 5006-1 and also shown in broken lines.

Although not required, in these examples, at least one of the radiopaque elements may be positioned in alignment along a longitudinal axis that extends through a commissure attachment feature. For example, with reference back to FIG. 19, radiopaque element 5020A is positioned on an outer surface of the inner cuff 5006 and aligned along an axis A3-1 that extends through the commissure attachment feature 5016A of the prosthetic heart valve 5000. Additionally, at least one more radiopaque element may be positioned in alignment with a commissure attachment feature. For example, radiopaque element 5020B is aligned along longitudinal axis A3-2 with commissure attachment feature 5016B and radiopaque element 5020C is aligned along longitudinal axis A3-3 with commissure attachment feature 5016C. In this example, radiopaque elements 5020B and 5020C are both positioned on an interior surface of inner cuff 5006 and shown in broken lines.

Figure 22:
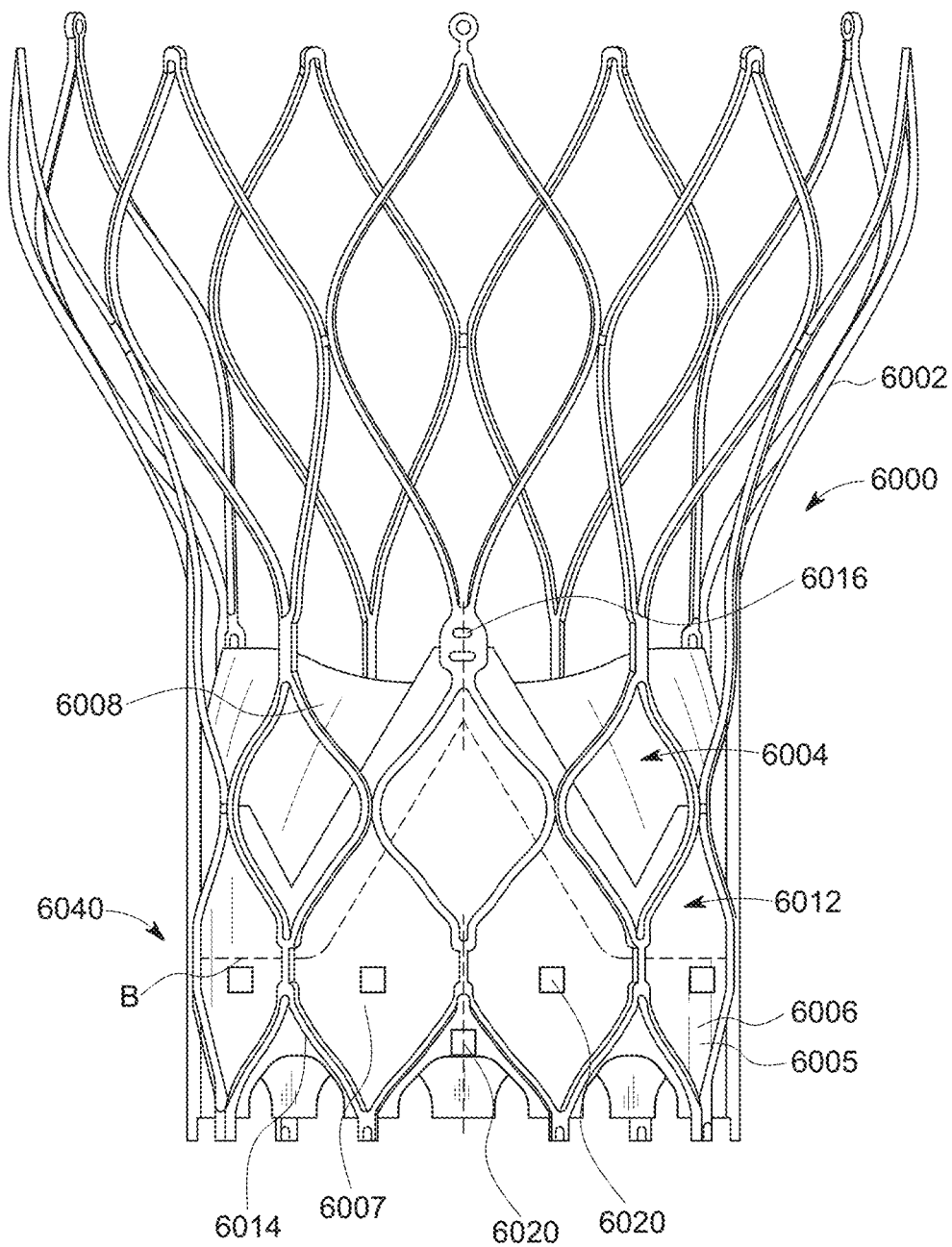
FIG. 22 is a front view of a prosthetic heart valve according to another embodiment of the disclosure.

FIG. 22 shows another example stent-supported heart valve 6000, which is similar to heart valve 100 shown in FIG. 1 to the extent that the valve assembly 6004 includes a cuff 6006 and leaflets 6008. Cuff 6006 is positioned on the inner or luminal side of stent 6002. The cuff 6006 can extend behind an outer cuff that is not included in this example, although an outer cuff could also be added in other examples. To assist a surgeon in detecting portions of heart valve 6000, radiopaque elements 6020 may be positioned on the outer surface 6007 of cuff 6006 within the first proximal row of cells 6012 in the annulus region 6040. Since the cuff 6006 extends between the struts 6014 of individual cells 6012, radiopaque elements 6020 will also appear to be positioned within cells of the stent, such that portions of the radiopaque element will be positioned between struts of a cell. Alternatively, radiopaque elements 6020 may be positioned on the interior surface of cuff 6006. In this example, at least one radiopaque element 6020 is optionally aligned with a commissure attachment feature 6016 and positioned between two adjacent cells 6012. In other examples, only three radiopaque elements 6020 are provided on the cuff 6006, each of which is aligned with a respective commissure attachment feature 6016.

Figure 22A:
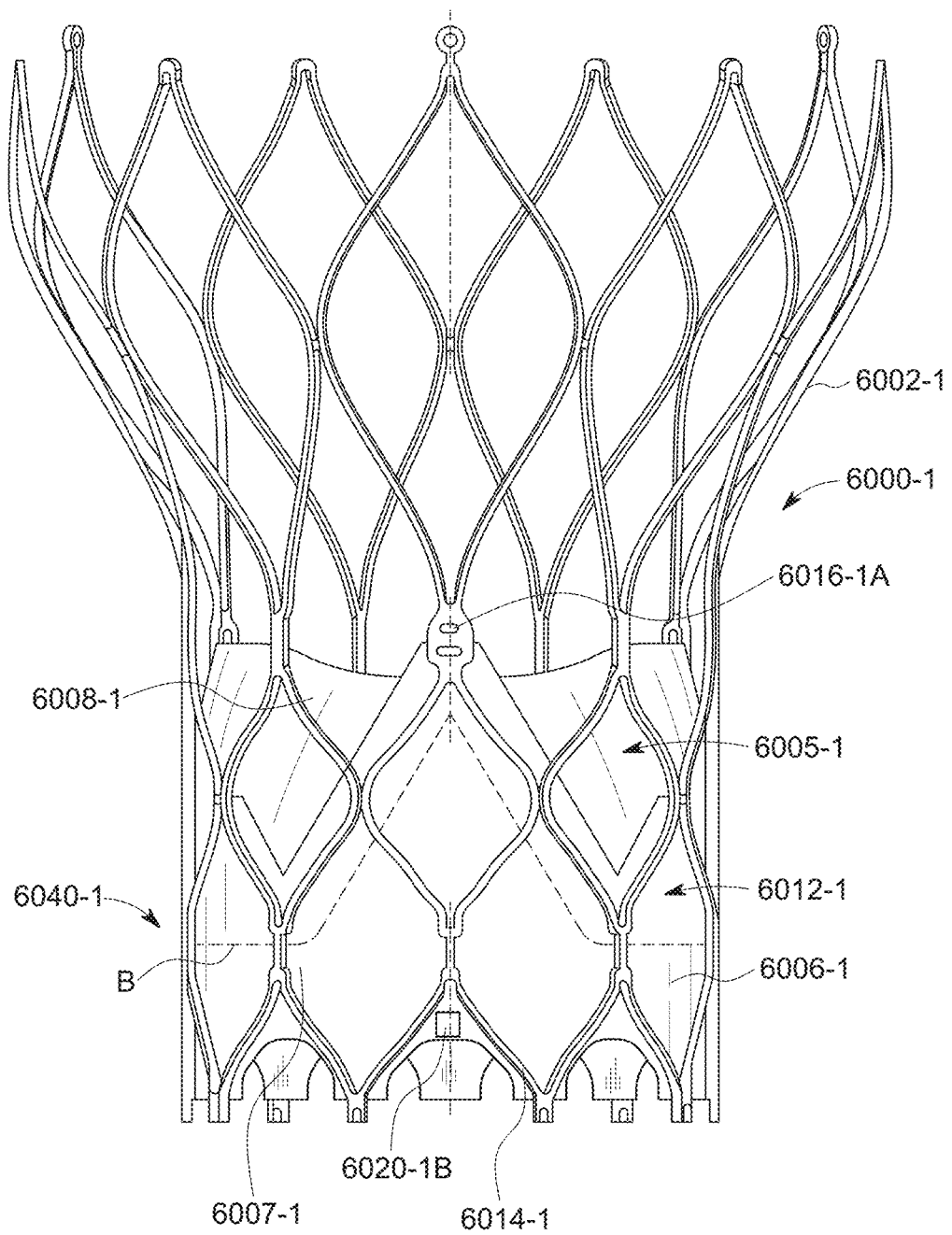
FIG. 22A is a front view of a prosthetic heart valve according to another embodiment of the disclosure.
Figure 22B:
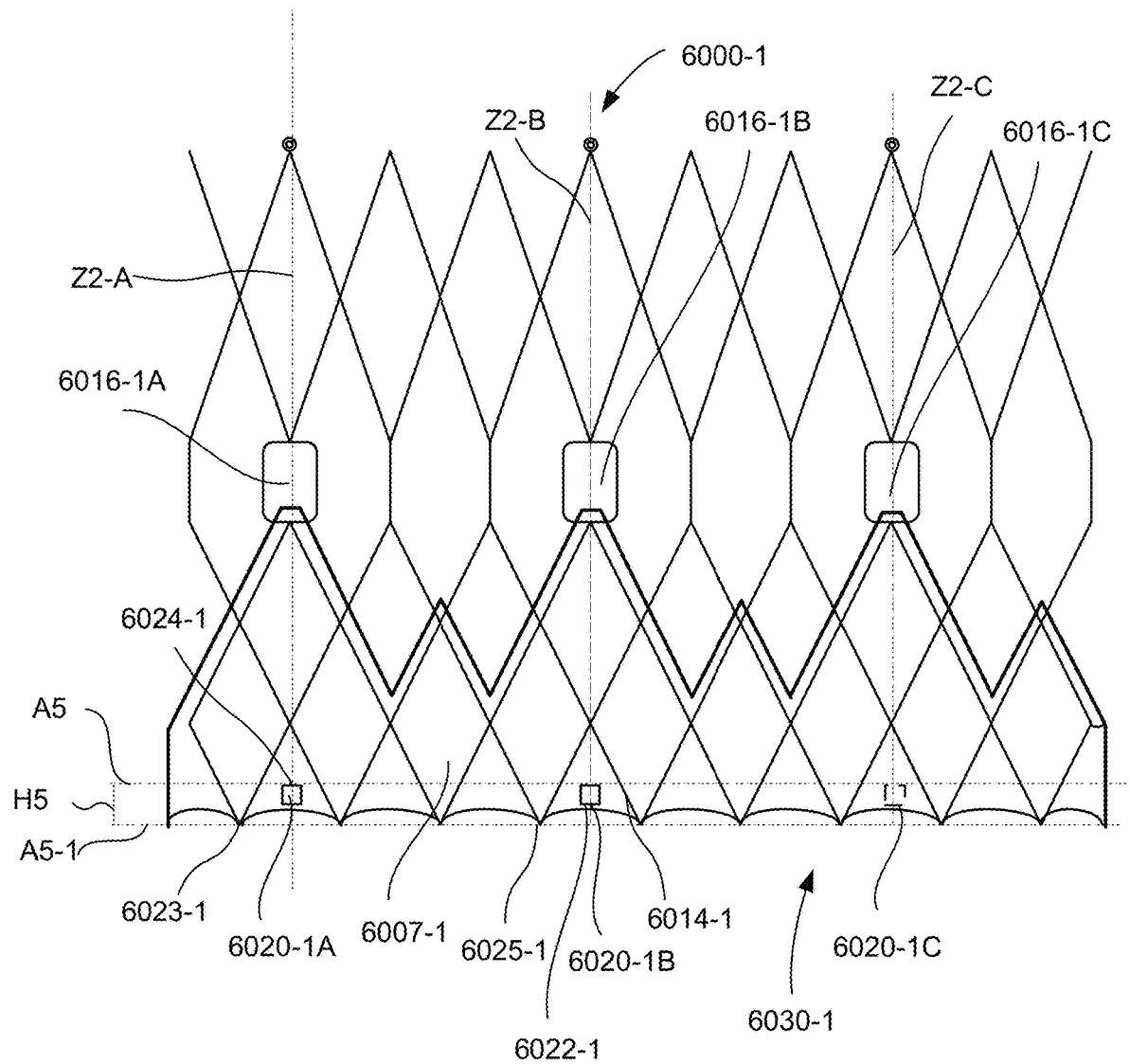
FIG. 22B is a schematic developed view of a stent and cuff having the arrangement of radiopaque elements shown in FIG. 22A.

FIGS. 22A-22B show another example stent-supported heart valve 6000-1 with a collapsible stent 6002-1 and valve assembly 6005-1, which is similar to the stent-supported heart valve 6000 shown in FIG. 22. This heart valve 6000-1 only differs from the example of FIG. 22 in the arrangement of the radiopaque elements. To assist a surgeon in detecting the position of the commissure attachment features, radiopaque elements 6020-1A, 6020-1B, and 6020-1C may be positioned in vertical alignment with respective ones of the commissure attachment features and, in some examples, may be the only radiopaque elements on the cuff of the stent supported heart valve 6000-1. As shown in this example, radiopaque element 6020-1A is aligned along an axis Z2-A with first commissure attachment feature 6016-1A, radiopaque element 6020-1B may be aligned along axis Z2-B with second commissure attachment feature 6016-1B, and radiopaque element 6020-1C may be aligned along axis Z2-C with third commissure attachment feature 6016-1C. A cuff 6006-1 extends on the luminal or inner side of stent 6002-1 between the struts 6014-1 of individual cells 6012-1, as well as between adjacent cells 6012-1 in the annulus region 6040-1.

At least one radiopaque element may be positioned on the outer surface 6007-1 of cuff 6006-1 and/or at least one radiopaque element may be positioned on the interior surface (not shown) of cuff 6006-1. For example, FIG. 22B illustrates an example where radiopaque elements are positioned on both the interior and exterior surfaces of the cuff. As shown, radiopaque elements 6020-1A and 6020-1B are positioned on the outer surface 6007-1 of cuff 6006-1 in the annulus region 6040-1, and particularly between struts 6014-1 of directly adjacent cells 6012-1. Radiopaque element 6020-1C is positioned on an interior surface of cuff 6006-1, as represented by dashed lines. In other examples, all of the radiopaque elements longitudinally aligned with the commissure attachment features may be positioned on the interior surface of the cuff or alternatively, all of the radiopaque elements aligned with the commissure attachment features may be positioned on the exterior surface of the cuff.

In still other examples, the radiopaque elements may be positioned anywhere on the cuff or leaflets, provided the radiopaque elements are longitudinally aligned with the commissure attachment features. Additionally, one or more of the radiopaque elements 6020-1A, 6020-1B, 6020-1C or additional radiopaque elements may be positioned on the leaflets 6008-1 or stent 6002-1 in longitudinal alignment with respective ones of the commissure attachment features 6016-1A, 6016-1B, 6016-1C.

In some examples, the radiopaque elements may be further aligned with one another to indicate a depth for implanting the prosthetic heart valve. Radiopaque elements 6020-1A, 6020-1B, 6020-1C may have their upper edges 6024-1 circumferentially aligned with one another along a circumferential reference line A5 that extends around the inflow end 6030-1 of the stent 6002-1. Reference line A5 may be positioned a distance H5 away from a second reference line A5-1 that extends circumferentially between each lowermost point 6023-1 at the stent tip 6025-1 of inflow end 6030-1 of the stent 6002-1. The distance H5 can vary, but can be set, for example, at 3 mm for the target depth. This can allow a surgeon to use the top edges 6024-1 of radiopaque elements 6020-1A, 6020-1B, 6020-1C to determine the appropriate depth for implanting prosthetic heart valve 6000-1.

In other examples, the radiopaque elements 6020-1A, 6020-1B, 6020-1C may be arranged so that their respective bottom edges 6022-1 are circumferentially aligned along reference line A5. This can allow a surgeon to use the bottom edges 6022-1 of the radiopaque elements to determine the appropriate depth for implanting heart valve 6000-1.

Figure 22C:
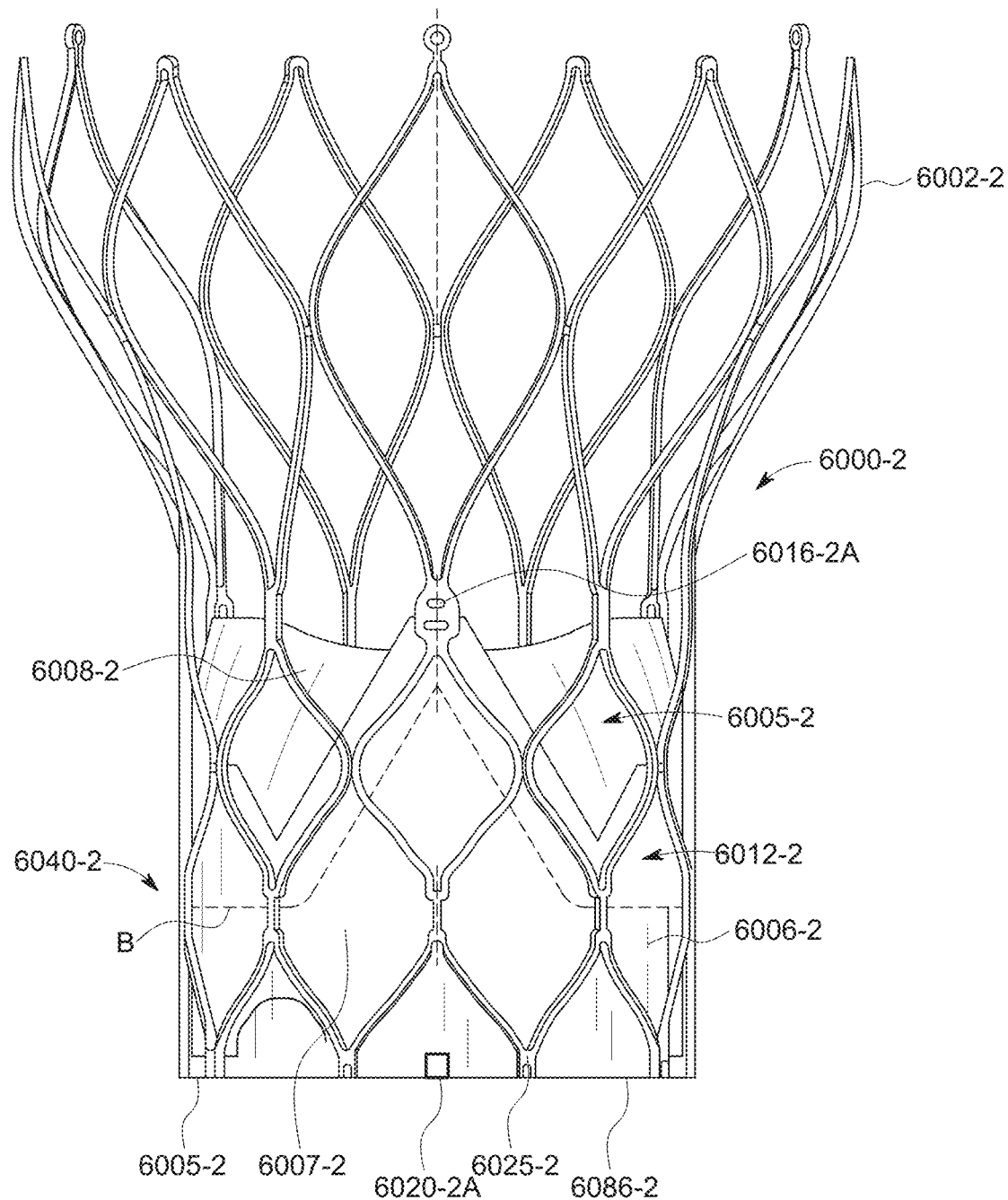
FIG. 22C is a front view of a prosthetic heart valve according to another embodiment of the disclosure.
Figure 22D:
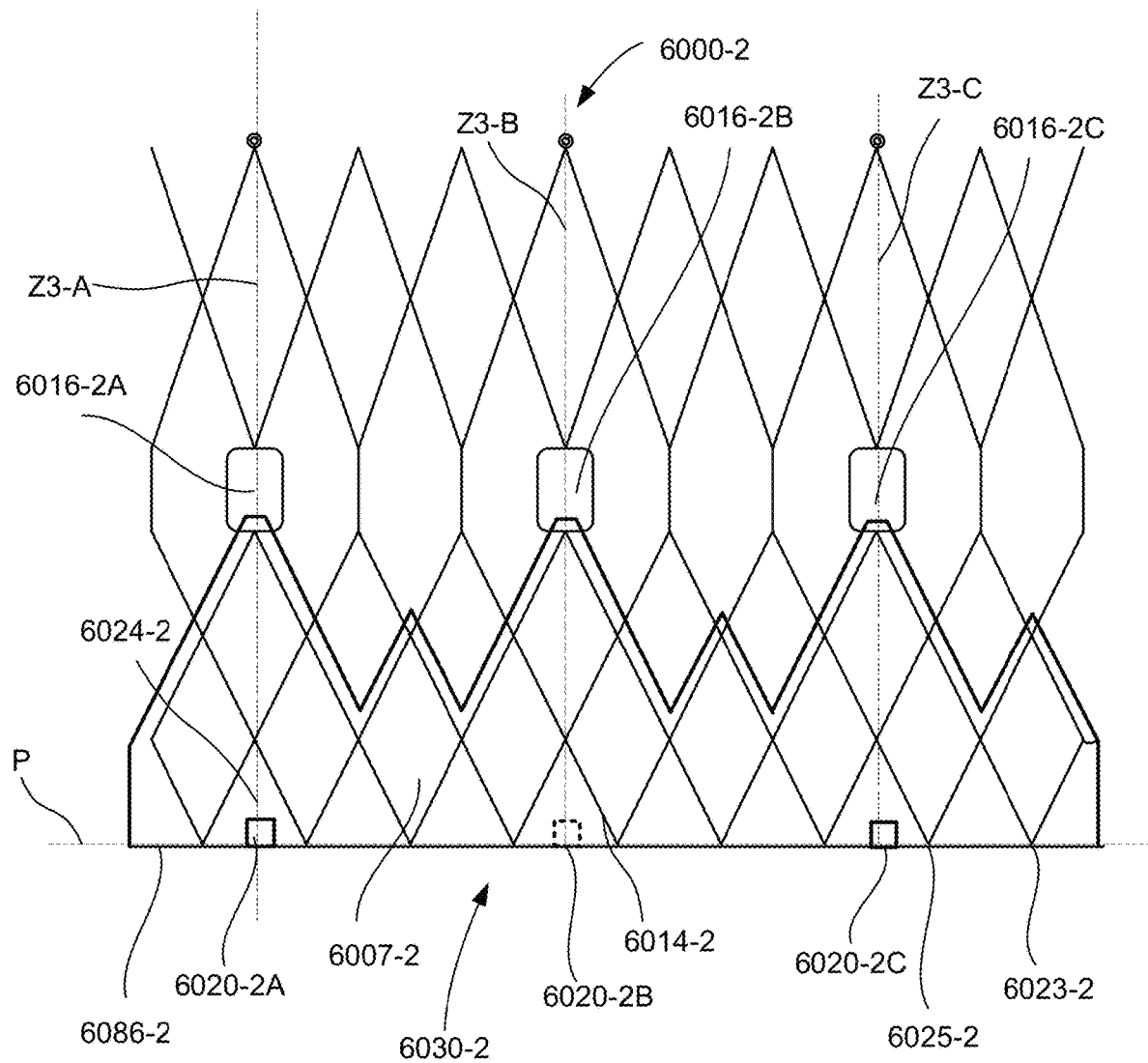
FIG. 22D is a schematic developed view of a stent and cuff having the arrangement of radiopaque elements shown in FIG. 22C.

FIGS. 22C-22D show another example stent-supported heart valve 6000-2 with a collapsible stent 6002-2 and valve assembly 6005-2, which is similar to the stent-supported heart valve 6000 shown in FIG. 22. This heart valve 6000-2 differs based only on the arrangement of the radiopaque elements on the cuff 6006-2, as well as a slight modification to the bottom edge of the cuff. As shown, cuff 6006-2 extends between the struts 6014-2 of individual cells 6012-2, as well as between adjacent cells 6012-2 in the annulus region 6040-2. A bottom edge 6086-2 of cuff 6006-2 extends circumferentially between each lowermost point 6023-2 of inflow end 6030-2 of the stent 6002-2, which in this example is at the stent tips 6025-2. The edge 6086-2 of the cuff 6006-2 at the inflow end 6030-2 is further arranged to extend circumferentially within the same plane P as the stent tips 6025-2.

At least one radiopaque element may be positioned at the bottom edge 6086-2 of the cuff 6006-2 to assist a surgeon in detecting the position of one or more of the inflow end 6030-2, stent tips 6025-2, or edge 6086-2 of the cuff 6006-2 of the prosthetic heart valve 6000-2. In one example, as best shown in FIG. 22D, first, second, and third radiopaque elements 6020-2A, 6020-2B, and 6020-2C are shown positioned on the cuff 6006-2 in the spaces between the cells 6012-2 in the first proximal row of cells in the annulus region 6040-2, as well as between struts 6014-2 of directly adjacent cells 6012-2, and more particularly adjacent the edge 6086-2 of the cuff 6006-2. Each of the three radiopaque elements 6020-2A, 6020-2B, 6020-2C lies in the same plane P as the bottom edge 6086-2 of the cuff 6006-2 and the tips 6025-2 of the stent 6002-2.

At least one radiopaque element may be positioned on the outer surface 6007-2 of cuff 6006-2 and/or at least one radiopaque element may be positioned on the interior surface (not shown) of the cuff 6006-2. For example, first and third radiopaque elements 6020-2A, 6020-2C are shown disposed on an outer surface 6007-2 of the cuff 6006-2. Second radiopaque element 6020-2B, shown in broken lines, is disposed on an interior surface of cuff 6006-2, such that the second radiopaque element is positioned below leaflets 6008-2. In other examples, all of the radiopaque elements may be disposed on the outer surface 6007-2 of cuff 6006-2 or all of the radiopaque elements may be disposed on the interior surface of cuff 6006-2. The radiopaque elements can be attached to the cuff 6006-2 using any means.

Additionally or alternatively, the radiopaque elements can be positioned to identify the positions of the commissure attachment features. In this example, first, second, and third radiopaque elements 6020-2A, 6020-2B, and 6020-2C may be positioned in vertical alignment with each of the commissure attachment features and, in some examples, may be the only radiopaque elements on the stent-supported heart valve 6000-2. In this example, radiopaque element 6020-2A is aligned with first commissure attachment feature 6016-2A along an axis Z3-A extending through commissure attachment feature 6016-2A, radiopaque element 6020-2B is aligned with second commissure attachment feature 6016-2B along an axis Z3-B extending through commissure attachment feature 6016-2B, and radiopaque element 6020-2C is aligned with third commissure attachment feature 6016-2C along an axis Z3-C extending through third commissure attachment 6016-2C. In other examples, the radiopaque elements may be positioned anywhere on the cuff or leaflets, provided the radiopaque elements are longitudinally aligned with the commissure attachment features. Similarly, one or more of the radiopaque elements 6020-2A, 6020-2B, 6020-2C, or additional radiopaque elements may be positioned on the leaflets 6008-2 or stent 6002-2 in longitudinal alignment with respective ones of the commissure attachment features 6016-2A, 6016-2B, 6016-2C.

Radiopaque Elements on Stent

Radiopaque elements can additionally or alternatively be provided on the stent itself. In some examples, the radiopaque elements may be formed as part of the stent structure, or a radiopaque element may be separately manufactured and attached directly to the stent structure.

Figure 23A:
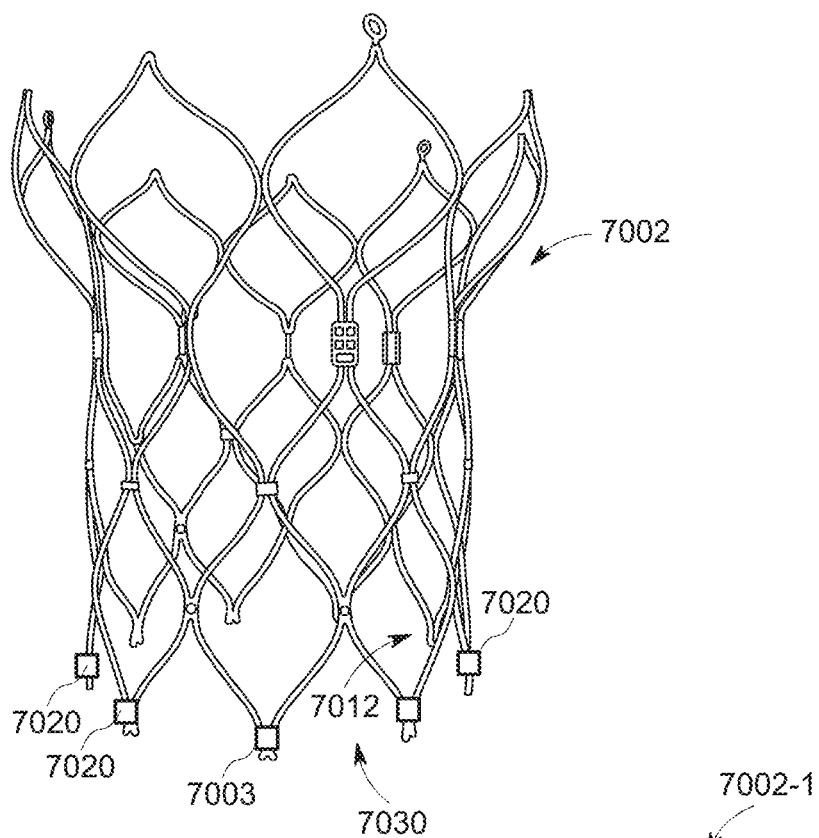
FIGS. 23A-23D are perspective views of prosthetic heart valves with radiopaque elements attached to different portions of the stent.
Figure 23B:
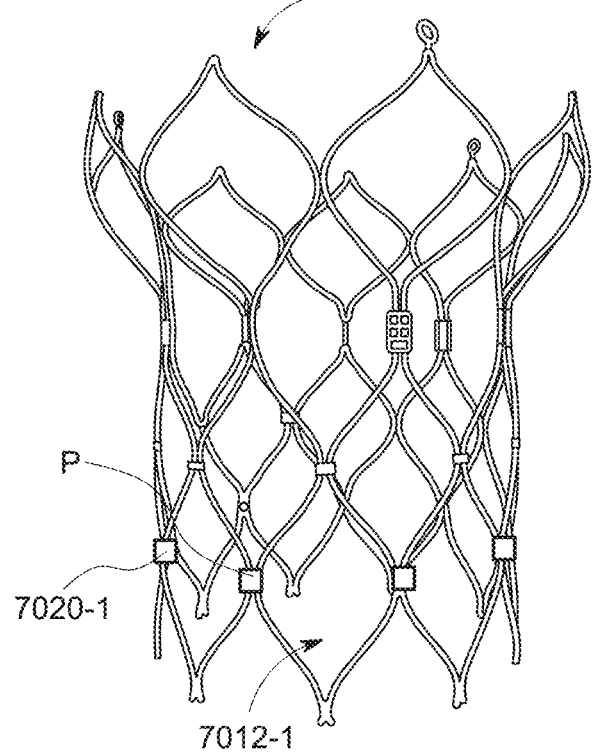
Figure 23C:
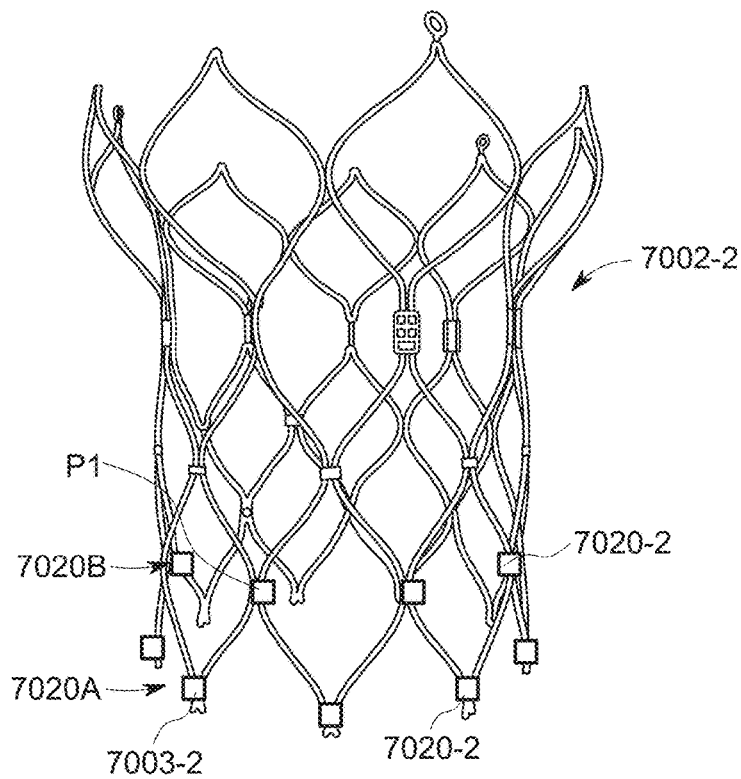
Figure 23D:
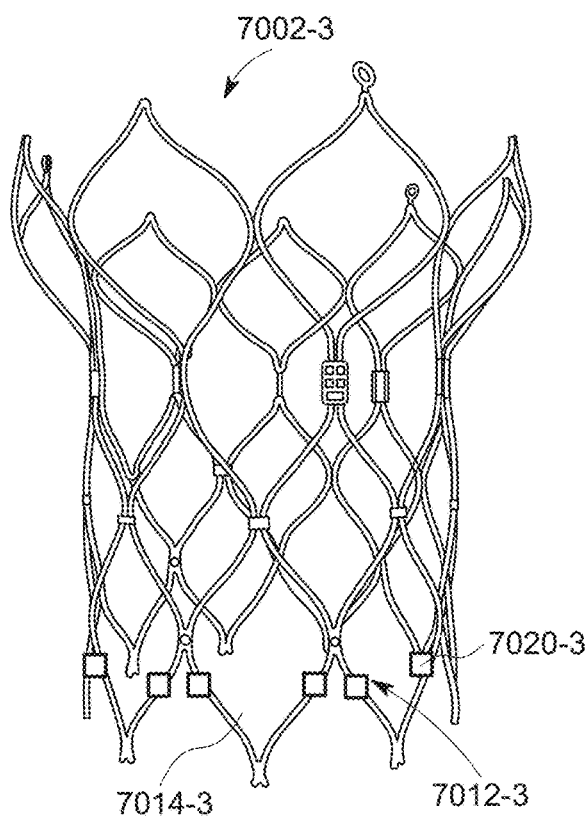

Radiopaque elements can be strategically positioned or disposed directly onto the stent in any desired configuration. FIGS. 23A-23D provide examples of the strategic placement of radiopaque elements on a stent. FIG. 23A illustrates an example stent 7002 with radiopaque elements 7020 disposed at the tip regions 7003 of the cells 7012 at the inflow end 7030 of the stent. Positioning radiopaque elements 7020 at the tip regions 7003 makes the inflow end of stent 7002 visible within the body when viewed under a fluoroscope, in x-rays or other medical imaging by a surgeon. FIG. 23B is another example stent 7002-1, but with radiopaque elements 7020-1 positioned at the point P where two directly adjacent stent cells 7012-1 meet. The radiopaque elements 7020-1 can indicate to the surgeon the particular location where the cells 7012-1 connect to one another. FIG. 23C shows the use of radiopaque elements in more than one location on stent 7002-2. As shown, a first row 7020A of radiopaque elements 7020-2 is positioned at or adjacent tip region 7003-2 and a second row 7020B of radiopaque elements 7020-2 is positioned at points P1 where directly adjacent cells meet. Using two rows of radiopaque elements may help the surgeon identify a certain range of depths to which the heart valve may be implanted or may simply give more visibility to the stent features when implanted within a patient. Finally, FIG. 23D shows another example stent 7002-3 with a single row of radiopaque elements 7020-3. In this example, each of the lower struts 7014-3 of each cell 7012-3 in the lowermost row of cells has a radiopaque element positioned thereon, with the radiopaque elements aligned circumferentially with one another. Collectively, the radiopaque elements 7020-3 can form a line or edge visible under fluoroscopy, in x-rays, or in other medical imaging that a surgeon can use to delineate how deep the stent 7002-3 may be implanted within the body.

Radiopaque elements can be provided directly onto the stent using a variety of methods including integrally forming radiopaque elements with the stent, as well as incorporating pre-formed radiopaque elements into the stent structure. For example, radiopaque elements may be coated onto the stent; openings in the stent structure can be filled with radiopaque material or with pre-formed radiopaque material; or pre-formed radiopaque material, such as radiopaque bands and markers, can be attached to the stent. Moreover, portions of the stent can be modified to better accommodate the attachment of radiopaque elements to the stent. Radiopaque sutures applied directly to the stent or to fabric or tissue components of the valve can also be used. Further, combinations of these and other methods and structures may be utilized. Some examples are discussed in more detail with reference to FIGS. 23E to 42.

Figure 23E:
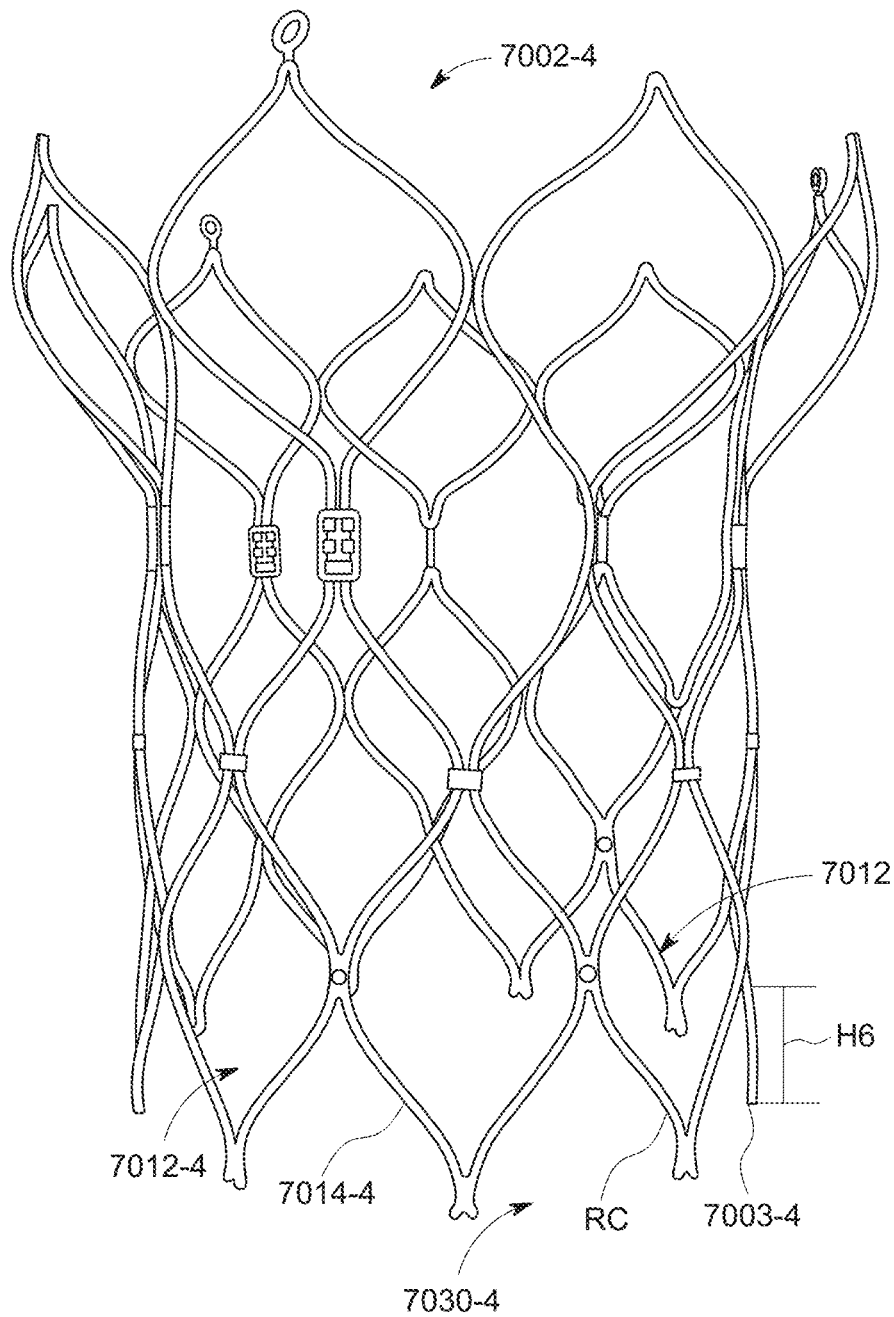
FIG. 23E is a perspective view of a prosthetic heart valve according to an embodiment of the disclosure.

One or more portions of the stent structure may be plated with a radiopaque material. Any portion of the stent may be plated, including the commissure attachment features, the abluminal and/or luminal surfaces, and/or any combination thereof. To plate the desired portions of the stent, the stent can be masked so that the plating occurs only on unmasked portions of the stent. The process of plating can be accomplished using any method, such as sputtering, electroplating, and the like. FIG. 23E illustrates an example stent 7002-4 in which the struts 7014-4 of the lower half of the proximal row of cells 7012-4 adjacent inflow end 7030-4 are plated with a radiopaque material. During plating, at least the upper half of the proximal row of cells 7012-4 may be masked so as to leave exposed the lower half of the struts of the cells 7012-4. A radiopaque coating RC may then be plated onto the exposed struts 7014-4 using a known method, such as electroplating. Radiopaque coating RC may be a gold/platinum plating, but any radiopaque material or combination of materials can be used. The radiopaque material may be applied to the stent until a coating thickness of 0.0015 inches is achieved, but in other examples, the coating thickness may be greater than or less than 0.0015 inches.

As in the previous examples, a pre-determined pattern of plating may be used to aid the surgeon during implantation of the stent 7002-4, which will ultimately support a heart valve. In this example, the plating of the radiopaque materials extends from the lowest or proximal-most stent tip 7003-4 at the inflow end 7030-4 to a height H6 along the struts 7014-4. Height H6 can be the depth to which the stent and heart valve should be implanted within the native valve annulus. For example, height H6 can be 0.003 inches from the inflow end, but can be greater than or less than 0.003 inches in other examples.

Figure 24:
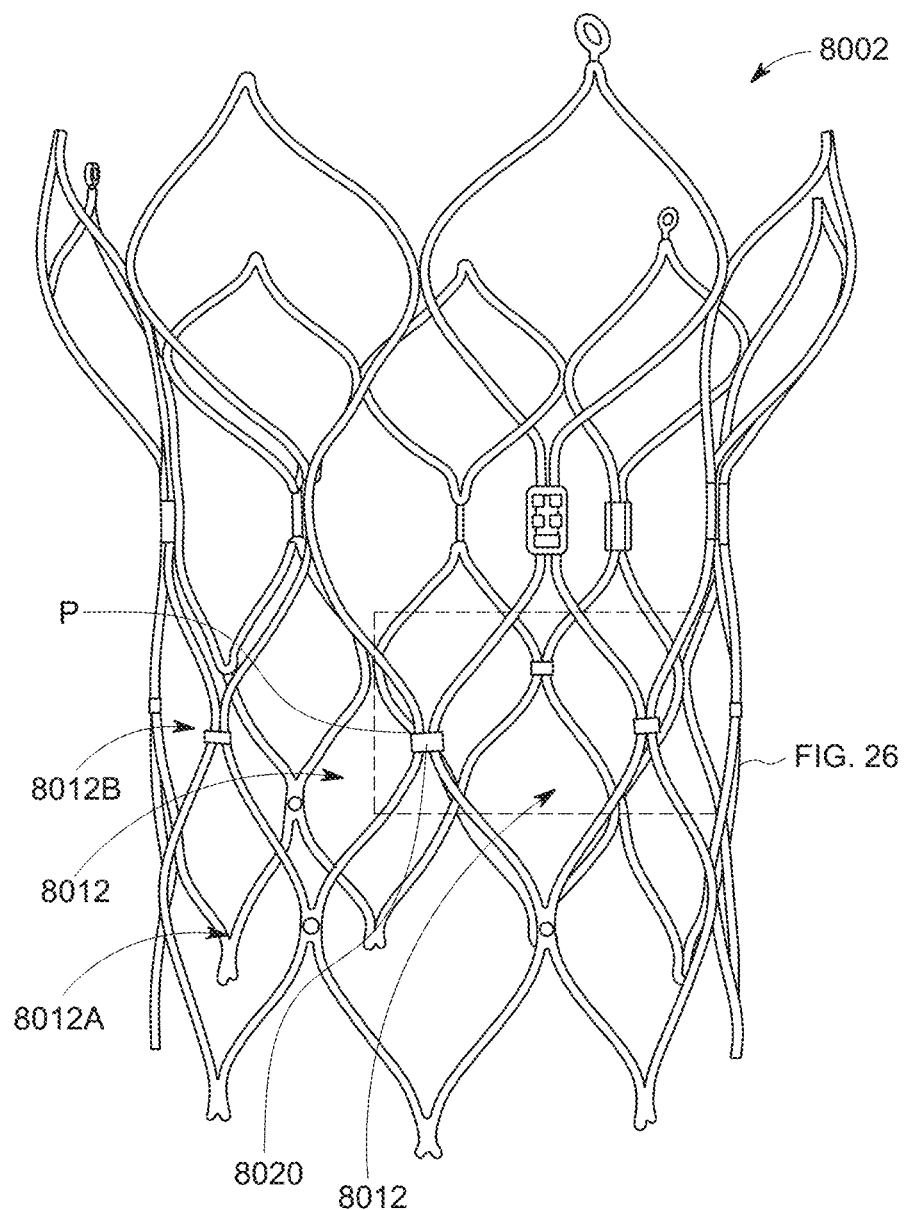
FIG. 24 is a perspective view of a prosthetic heart valve with a radiopaque marker band according to an embodiment of the disclosure.
Figure 25:
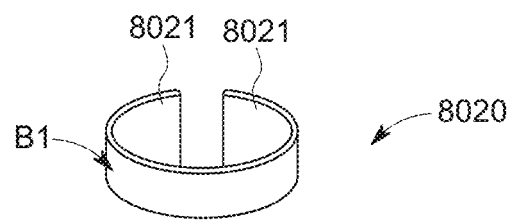
FIG. 25 is an example of a radiopaque marker band.
Figure 26:
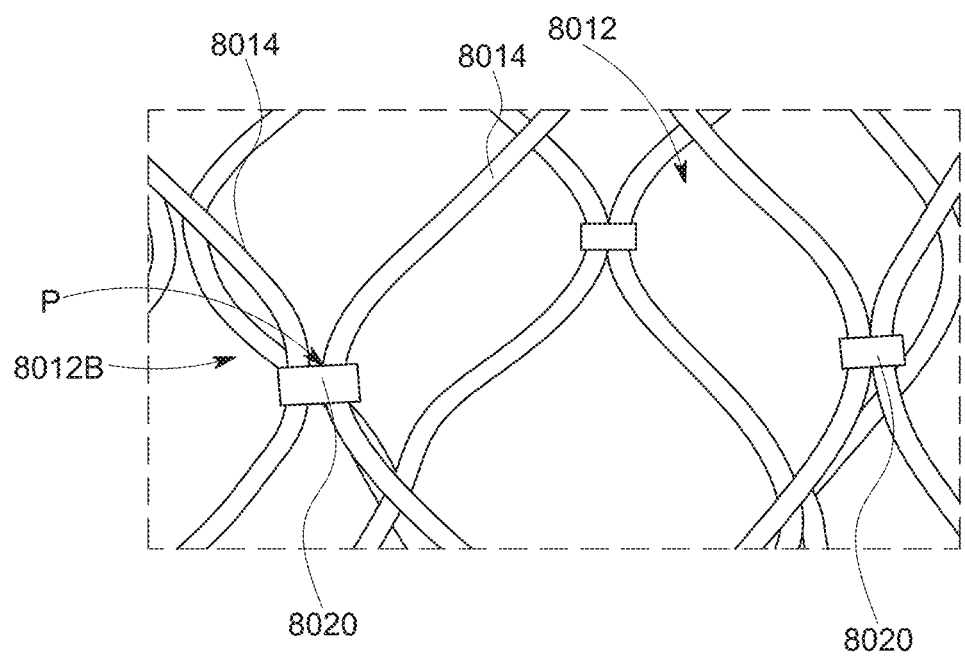
FIG. 26 is an enlarged view of FIG. 24.
Figure 27:
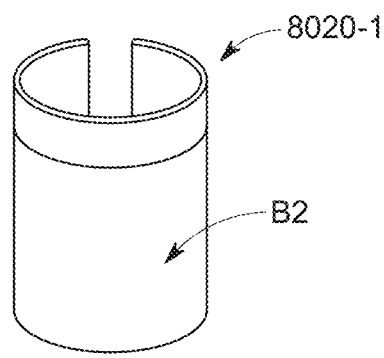
FIG. 27 is a view of an alternative radiopaque marker band.

Radiopaque marker bands may be provided and attached to any portion of the stent, such as between cells, along a single strut, at a commissure attachment feature, and/or at the inflow end or outflow end of the stent. FIG. 24 illustrates an example stent 8002 that includes a first row of cells 8012A and a second row of cells 8012B. Radiopaque marker bands 8020 are shown attached at points P where two directly adjacent cells 8012 in second row 8012B meet and are positioned circumferentially around the annulus section of stent 8002. Radiopaque marker band 8020, shown in FIG. 25, may be a ring having a body B1 with ends 8021 spaced apart from one another. Radiopaque marker bands 8020 may be formed from any radiopaque materials, including gold and/or platinum and/or metal alloys. Ends 8021 of radiopaque marker bands 8020 may be wrapped around the attachment points P, as better seen in the enlarged view of FIG. 26. To secure radiopaque marker bands 8020 to stent 8002, the bands may be crimped to the stent. Radiopaque marker bands 8020 may take any shape, size, or form, including those disclosed herein. One alternative example of a radiopaque marker band 8020 is shown in FIG. 27, in which the body B2 of the radiopaque marker band 8020-1 is elongated as compared to body B1 of marker band 8020 shown in FIG. 25. The radiopaque marker bands 8020, 8020-1 may be attached to the stent 8002 using known means, such as crimping. Alternatively, the stent 8002 may be designed so that radiopaque marker bands 8020, 8020-1 are integrally formed as part of the stent structure.

Figure 28:
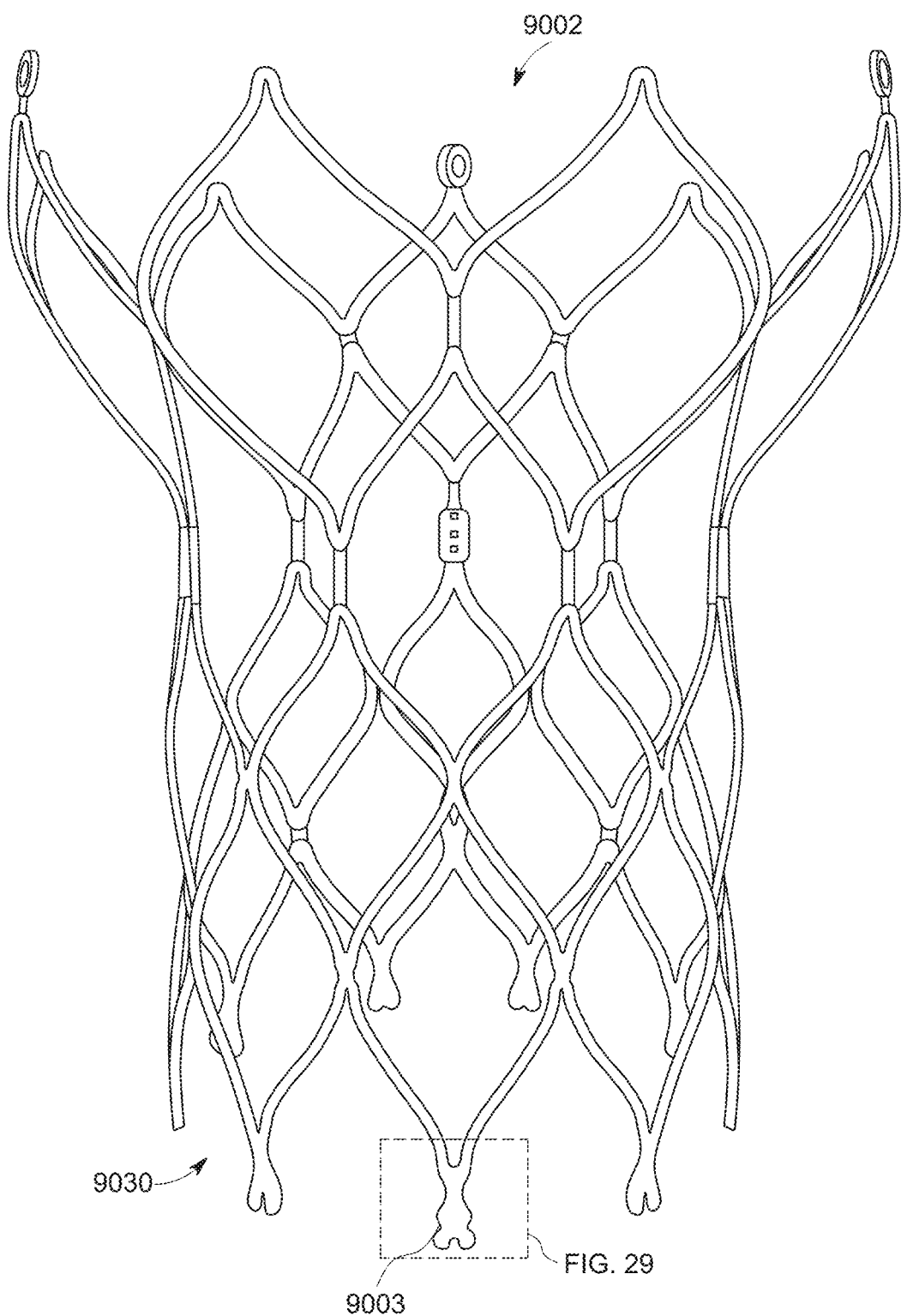
FIG. 28 is a perspective view of a prosthetic heart valve with an enlarged tip region according to an embodiment of the disclosure.
Figure 29:
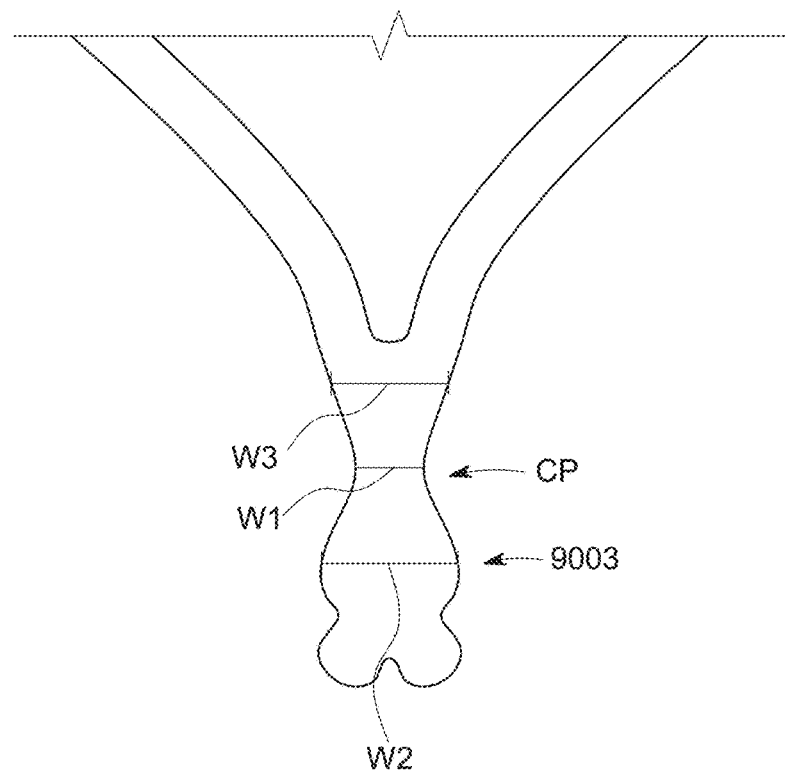
FIG. 29 is an enlarged view of the tip region of the prosthetic heart valve of FIG. 28.
Figure 30:
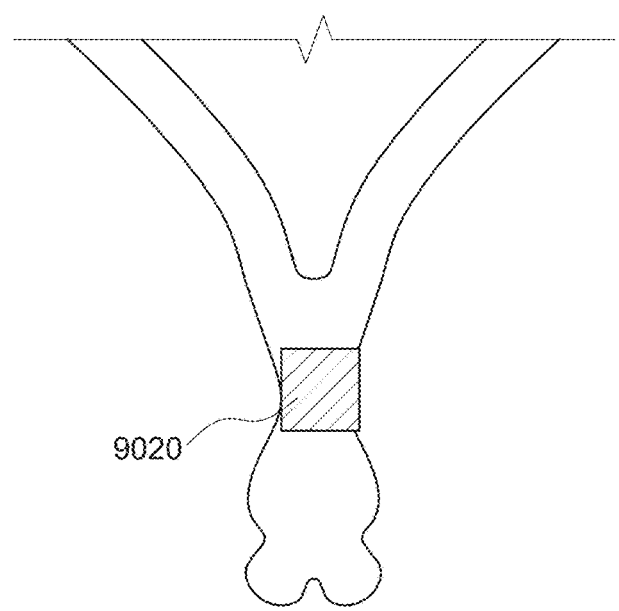
FIG. 30 is a view similar to FIG. 29 with a radiopaque element on the tip region.

To increase visibility of the stent at the inflow end, the tip region of the cells at the inflow end may also be enlarged. The increased size can better accommodate radiopaque elements that are directly attached to the stent and/or formed integrally with the tip. FIG. 28 illustrates an example stent 9002 with an enlarged tip region 9003 at the inflow end 9030 of stent 9002. As shown in the enlarged view of FIG. 29, tip region 9003 may be elongated and contoured with an hourglass shape so that a central portion CP of tip region 9003 has a width W1 that is smaller than the width W2 at a first end of the tip region 9003 and the width W3 at a second end of tip region 9003 closest to the cells of the stent. Width W2 and width W3 may be the same or may differ. The central portion CP may be sized to receive a radiopaque element 9020, such as a marker band shown in FIG. 30, but any type of desired radiopaque element may be utilized.

Figure 31:
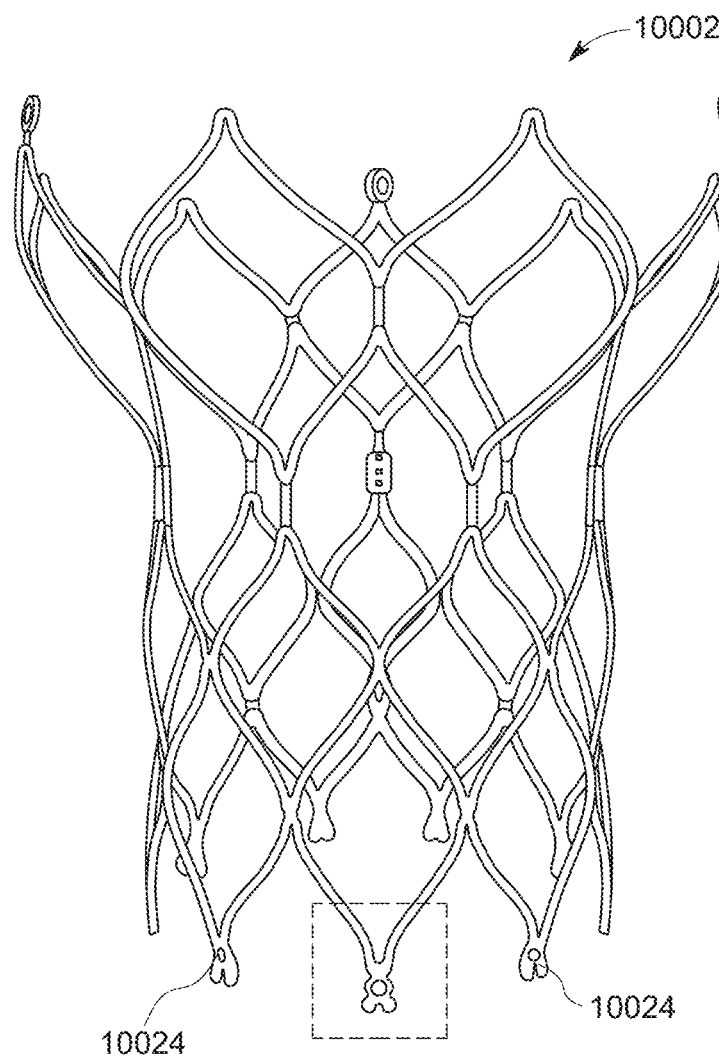
FIG. 31 is a perspective view of a prosthetic heart valve according to an embodiment of the disclosure.
Figure 31A:
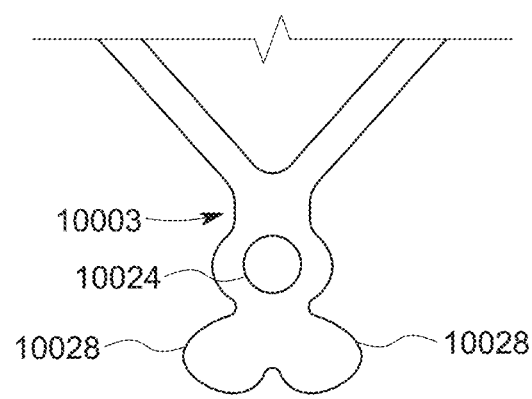
FIG. 31A is an enlarged schematic view of the tip region of the prosthetic heart valve of FIG. 31.
Figure 32:
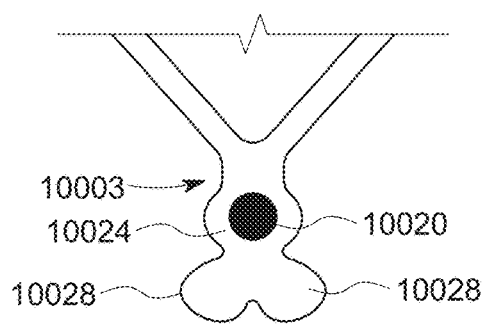
FIG. 32 is a view similar to FIG. 31A with a radiopaque element thereon.

Visibility at the inflow end of a stent can be further improved by additionally or alternatively providing openings or apertures in the tip region of the stent, and partially or fully filling the openings with a radiopaque material, including rivets, swages or welds formed with radiopaque material. FIG. 31 and the enlarged view of FIG. 31A provide an illustrative example of a stent 10002 with stent openings 10024 provided in the tip region 10003. The tip region 10003 may include one or more protrusions or feet, and in this example, tip region 10003 includes two feet 10028, as well as a circular region positioned between the two feet 10028 and the cell structure of the stent. The stent openings 10024 may be provided within the circular regions using any means, including being formed during formation of the stent or drilling the stent opening after stent formation. The stent openings 10024 may be approximately 0.02 inches in diameter, but in other examples, the diameter may be larger or smaller than 0.02 inches. For example, the openings could be 0.044 inches or 0.057 inches in diameter. The stent openings may be filled with a radiopaque material to form a radiopaque element 10020, as shown in the schematic view of FIG. 32. In this example, a rivet formed of a radiopaque material, such as platinum, tantalum and/or gold, may be inserted into stent opening 10024 to form the radiopaque element 10020. Openings 10024 may instead be filled with a reflowed radiopaque material that is cured. Alternatively, gold, platinum, or tantalum balls may be swaged into the openings.

Figure 33:
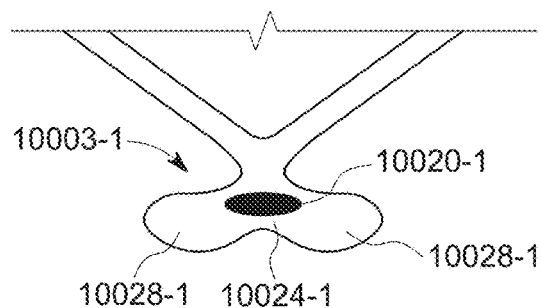
FIG. 33 is an enlarged schematic view of a tip region of a stent having a radiopaque element thereon according to an embodiment of the disclosure.
Figure 34:
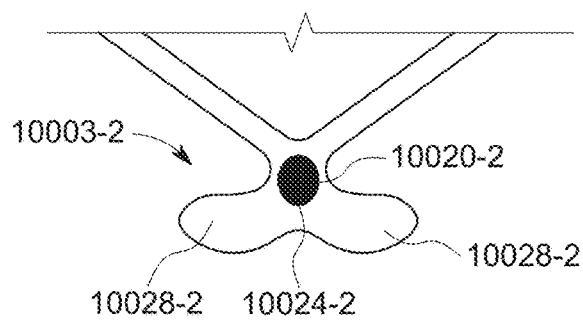
FIG. 34 is a view similar to FIG. 33 having a different radiopaque element thereon.

The stent openings 10024 may be provided in various shapes, sizes, and arrangements. A few illustrative examples are shown in FIGS. 33-34. Turning first to FIG. 33, a schematic view of an example tip region 10003-1 with stent openings and a radiopaque element therein is shown. Tip region 10003-1 includes two feet 10028-1 with an elongated or oval-shaped stent opening 10024-1 provided between the two feet 10028-1. A radiopaque material may be provided within the stent opening 10024-1 in any of the manners described herein to form radiopaque element 10020-1.

FIG. 34 illustrates another schematic view of an example tip region 10003-2, which includes a stent opening 10024-2 and two feet 10028-2. Stent opening 10024-2 has straight edges and may be in the shape of a rectangle, but in other examples may have rounded edges. Stent opening 10024-2 is shown positioned between the two feet 10028-2, but in other examples, stent opening 10024-2 may be positioned between the two feet and the cell structure of the stent. Radiopaque material may be provided within stent opening 10024-2 in any of the manners described herein so as to form a radiopaque element 10020-2.

Figure 35:
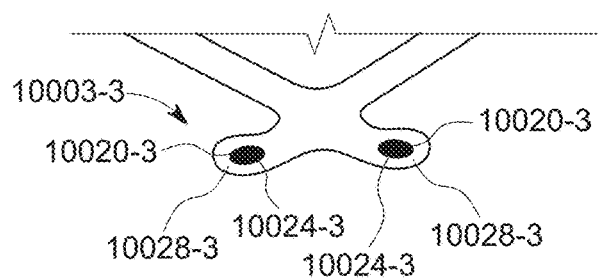
FIG. 35 is a view similar to FIG. 33 having a pair of radiopaque elements thereon.

FIG. 35 is a schematic view of an alternative tip region 10003-3. In this example, tip region 10003-3 includes two feet 10028-3, both of which include a stent opening 10024-3. Radiopaque material may be provided within each of the stent openings 10024-3 to form two radiopaque elements 100020-3 in tip region 10003-3. The radiopaque elements may include any of the radiopaque elements previously described herein.

FIG. 36 illustrates another example stent utilizing radiopaque elements at the inflow end. Example stent 10102 includes tip regions 10103 that vary along the inflow end of the stent. As shown in the enlarged view of FIG. 37, the tip regions 10103 at the proximal end of some of the cells 10112 include only feet 10128, while the tip regions 10103 at the proximal end of other cells include only structures having a stent opening 10124. The stent openings 10124 may be enlarged so as to extend proximally of the feet 10128 at the ends of the directly adjacent stent cells 10112. The stent openings 10124 may be at least 0.057 inches in diameter, but in other examples may be larger or smaller than 0.057 inches in diameter. As in the previous examples and as shown in FIG. 38, stent openings 10124 may receive a radiopaque material, such as radiopaque rivets, swages, or welds, to form radiopaque elements 10120. The size and location of the stent openings may vary widely, as may the radiopaque material forming radiopaque elements 10120.

FIGS. 39 and 40A illustrate another example stent utilizing radiopaque elements at the inflow end. Example stent 10102-1 includes tip regions 10103-1 that vary along the inflow end of the first row of cells 10112-1. As shown in the enlarged view of FIG. 40A, some of the tip regions 10103-1 include only feet 10128-1, while other tip regions 10103-1 include both feet 10128-1 and structures having a stent opening 10124-1. The stent openings 10124-1 may be positioned between feet 10128-1 and the cell structure of the stent. The stent openings 10124-1 may be at least 0.057 inches in diameter, but in other examples may be larger or smaller than 0.057 inches. As in the previous examples and as shown in FIG. 40B, stent openings 10124-1 can receive a radiopaque material, such as radiopaque rivets, swages, or welds to form radiopaque elements 10120-1. The size and location of the stent openings may vary widely, as may the radiopaque material forming radiopaque elements 10120-1.

Figure 41:
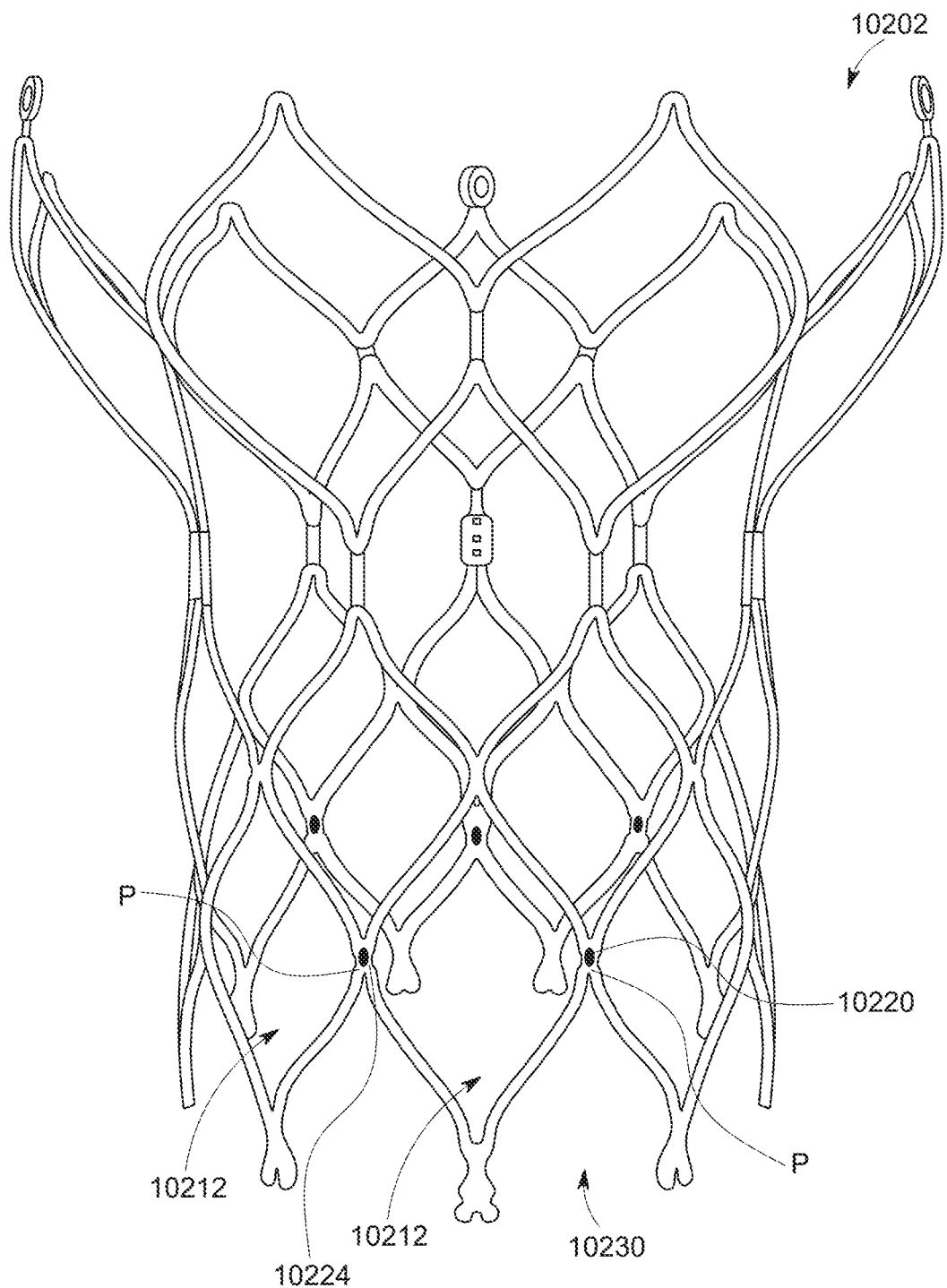
FIG. 41 is a perspective view of a stent with radiopaque materials according to an embodiment of the disclosure.

As noted above, openings configured to receive radiopaque elements may be positioned on any portion of the stent. FIG. 41 illustrates an example stent frame 10202 for supporting a prosthetic heart valve with openings that are positioned on a different portion of the stent. Cells 10212 in the first row of proximal cells adjacent the inflow end 10230 are directly and laterally adjacent one another. At each point P where two laterally adjacent cells 10212 meet, a stent opening 10224 may be provided. Stent openings 10224 may have a diameter, for example, of 0.015 inches, but in other examples, the diameter of the openings may be less than or greater than 0.015 inches. The openings can be sized to receive radiopaque material, such as platinum, tantalum, gold, and the like, so as to form a radiopaque element 10220. The radiopaque material may be provided as a pre-formed marker deposited into the opening or it may be unformed radiopaque material that is deposited into the opening.

Radiopaque Sutures on Stent and/or Cuff

Figure 42:
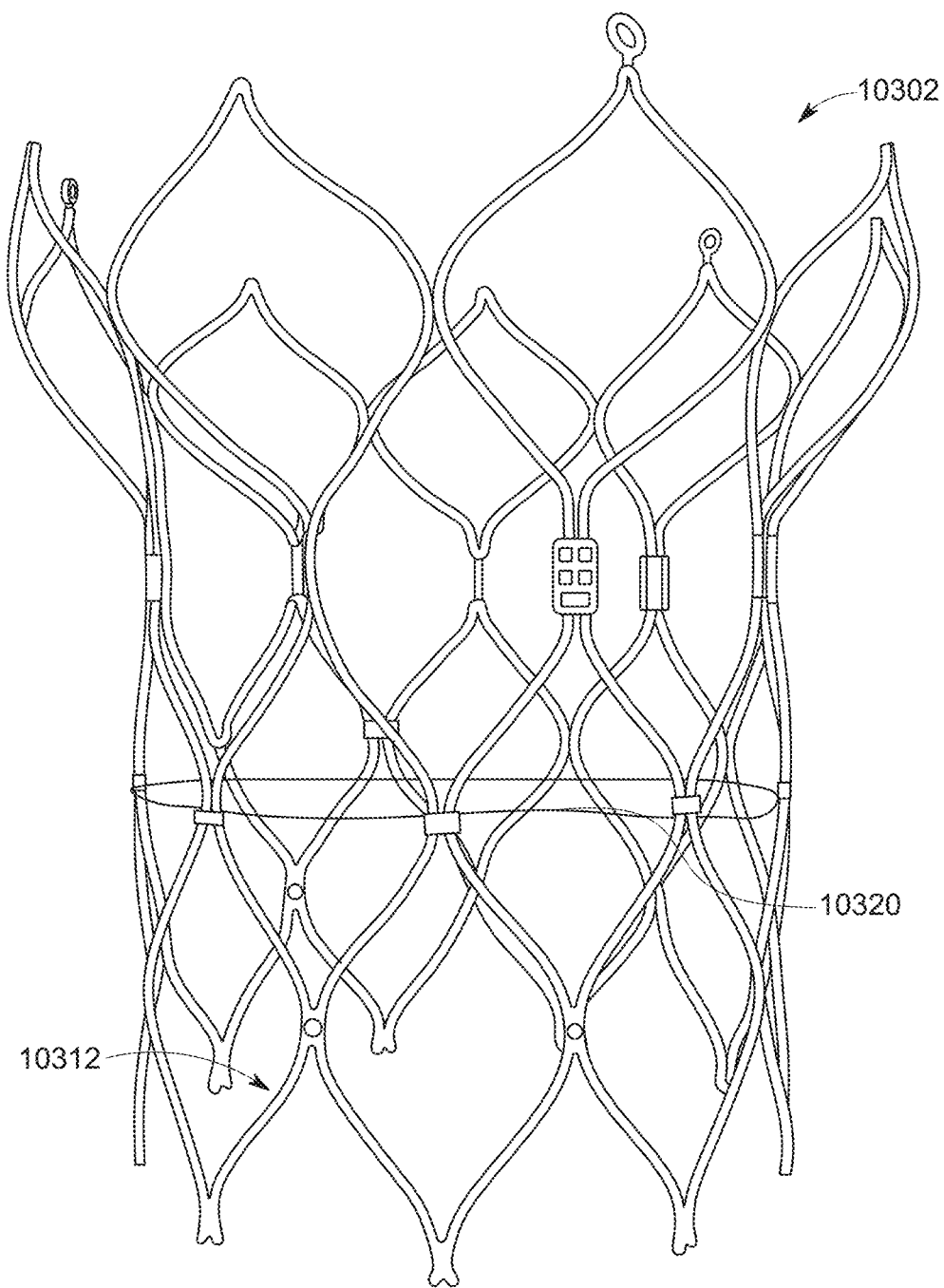
FIG. 42 is a perspective view of a stent with radiopaque sutures according to an embodiment of the disclosure.

The radiopaque element also may be a suture or suture material. The suture material can be provided directly on the stent or on the inner or outer cuff to enhance the ability of a surgeon to determine the position of a prosthetic heart valve within the body. FIG. 42 illustrates an example stent 10302 in which a radiopaque suture 10320 extends circumferentially around the annulus section of stent 10302. The radiopaque suture 10320 may be provided on the stent in numerous ways. For example, the suture may be attached to the stent only at two ends, or the suture may wrap around a strut of each individual cell 10312 or of alternating cells 10312.

The radiopaque suture 10320 may be formed of any radiopaque suture material. For example, the suture material may be comprised of polyethylene or polymer fiber that is loaded with a radiopaque material. Barium sulfate is one example of a radiopaque material that can be loaded onto a suture material, but other radiopaque materials can be loaded on the suture material to achieve a radiopaque suture. Similarly, other types of suture material in combination with any radiopaque material can be utilized.

Figure 43:
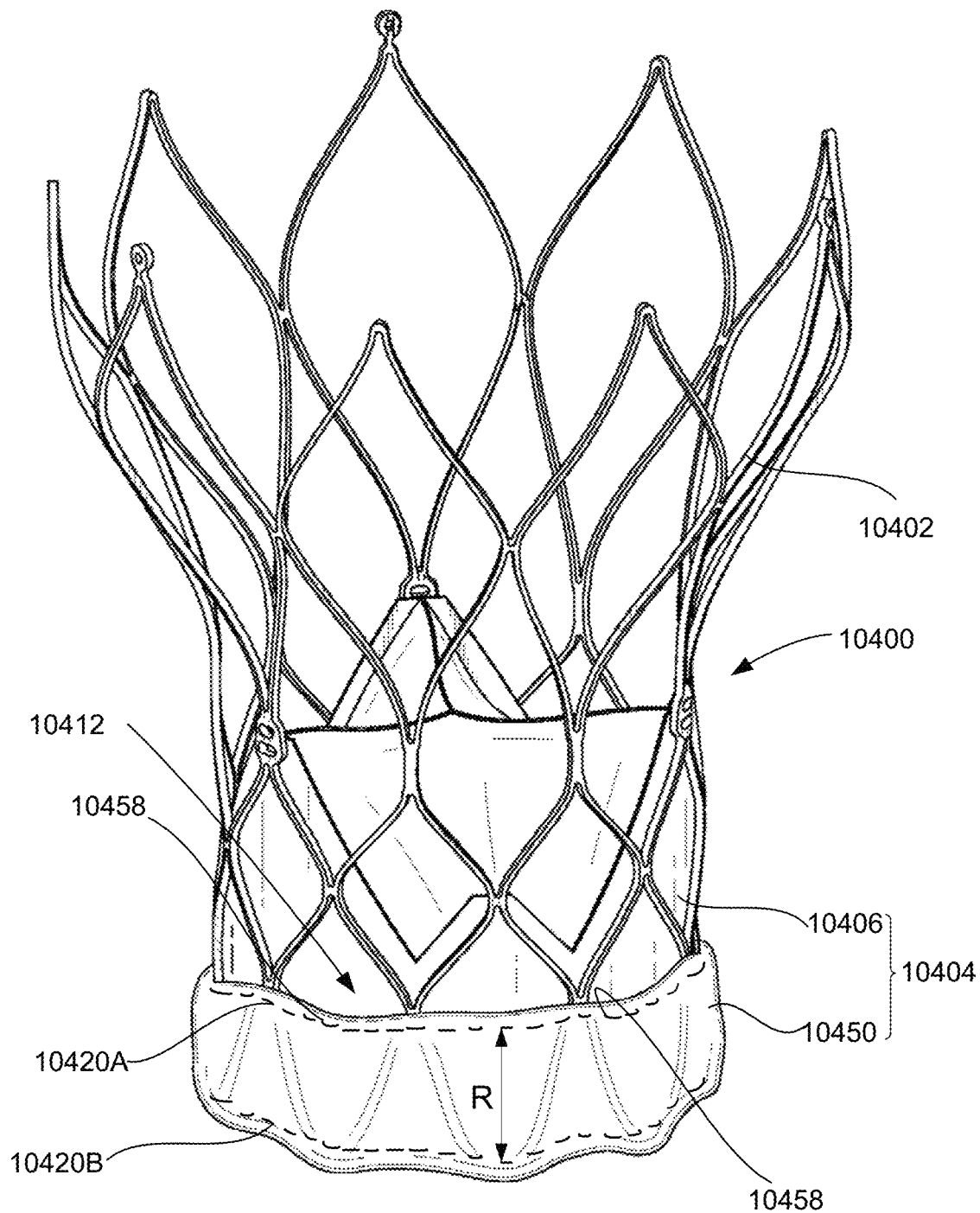
FIG. 43 is a perspective view of a prosthetic heart valve according to another embodiment of the disclosure.

Radiopaque sutures may additionally or alternatively be sutured directly to the inner cuff, outer cuff, or a combination of the inner cuff and outer cuff. FIG. 43 is an example stent-supported prosthetic heart valve 10400. Prosthetic heart valve 10400 is similar to previous prosthetic heart valves described herein and includes a stent 10402, and a cuff 10404, including an inner cuff 10406, an outer cuff 10450, and one or more pockets 10412. Radiopaque elements in the form of radiopaque sutures extend along the outer cuff 10450. A first radiopaque suture 10420A extends adjacent the distal edge 10458 of outer cuff 10450, and a second radiopaque suture 10420B extends adjacent the inflow edge of outer cuff 10450 adjacent the inflow end of the stent. To ensure that the pockets 10412 are capable of moving and billowing into an expanded condition, the first radiopaque suture 10420A may be sutured only to the outer cuff 10450. Similarly, the second radiopaque suture 10420B may be sutured only to the outer cuff 10450 to ensure that the pocket can fully expand, as necessary. In this example, the first and second radiopaque sutures 10420A, 10420B may define a region R indicating the desired depth of implantation of the prosthetic heart valve 10400. In other examples, radiopaque sutures may be provided on the inner cuff 10406, or on a combination of the inner cuff 10406 and outer cuff 10450. In yet another example, radiographic sutures may be used to connect the inner cuff to the commissure attachment features. Such sutures would help the surgeon locate the positions of the commissure attachment features using medical imaging during the deployment of the prosthetic heart valve. The radiopaque sutures may also additionally or alternatively be sutured to one or more leaflets, as described below.

Radiopaque Elements on Leaflets

Figure 44:
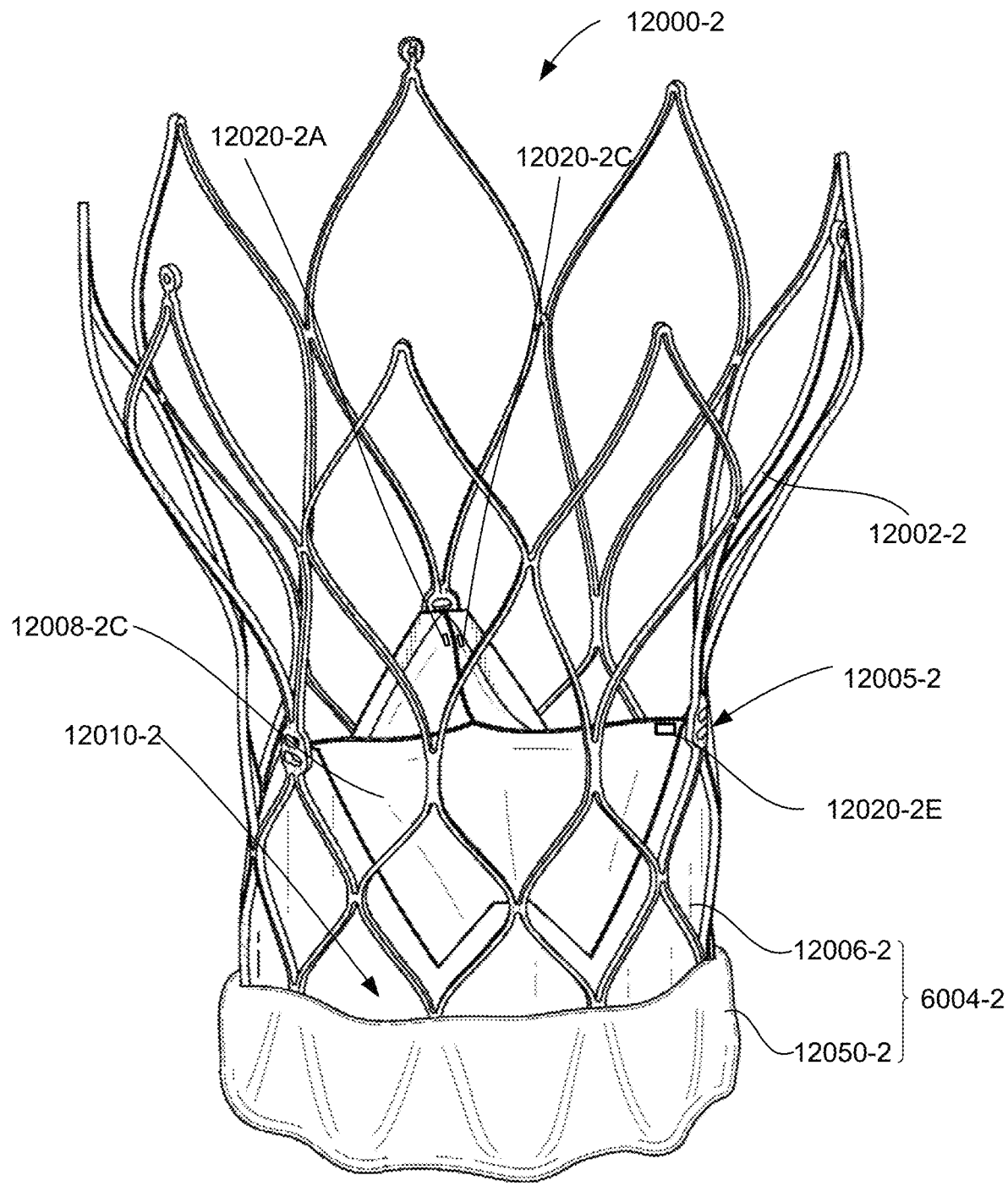
FIG. 44 is a perspective view of a prosthetic heart valve according to another embodiment of the disclosure.
Figure 45:
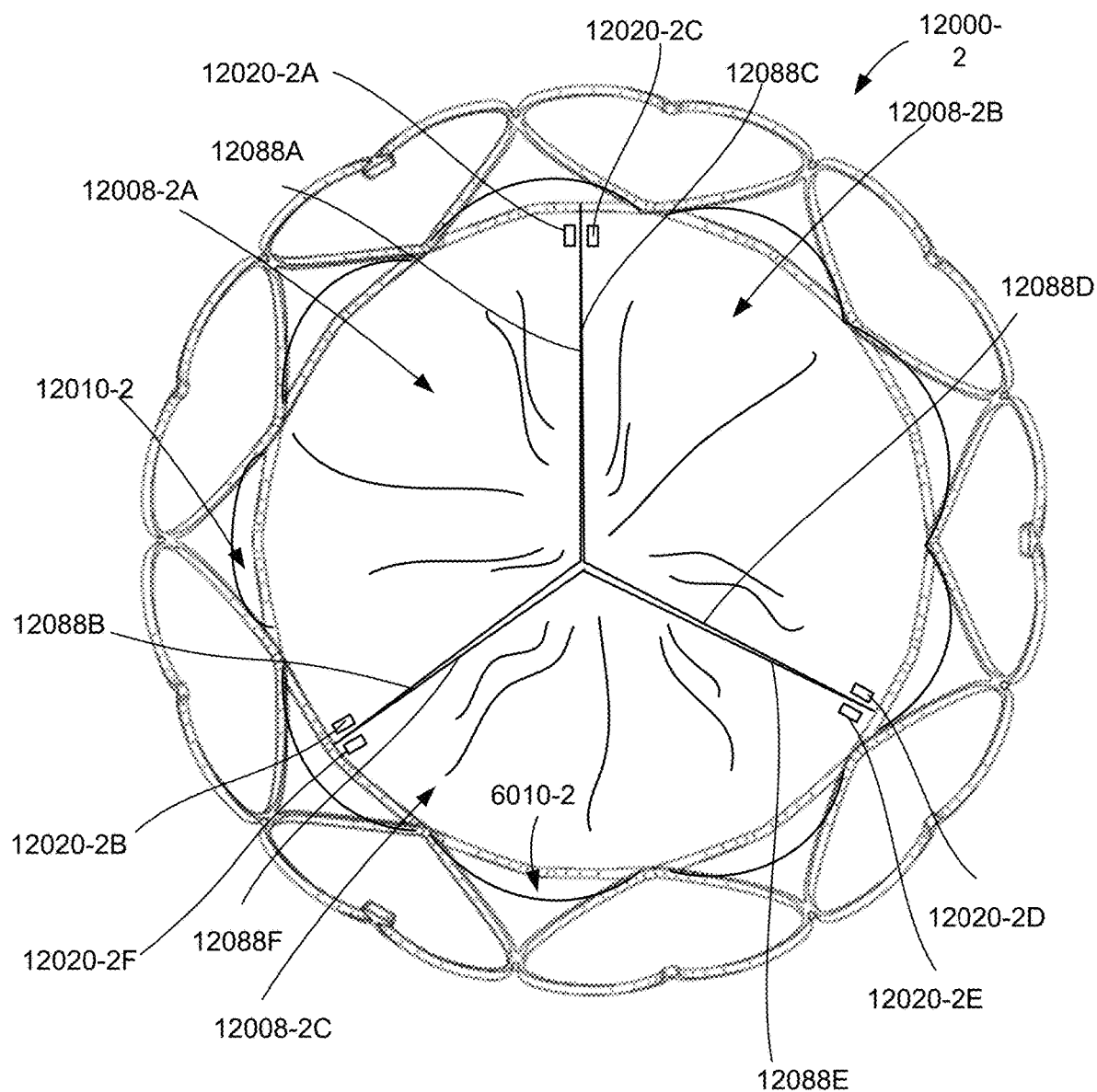
FIG. 45 is a schematic top view of the prosthetic heart valve of FIG. 44.

One or more radiopaque elements can be provided on one or more leaflets alone, or in combination with radiopaque elements that are on either or both of the stent and the cuff. For example, FIGS. 44 and 45 illustrate a stent-supported prosthetic heart valve 12000-2 that is otherwise identical to the stent-supported prosthetic heart valves in FIGS. 13-21, except for the arrangement of radiopaque elements only on each of the leaflets 12008-2A, 12008-2B, 12008-2C. Otherwise, the configuration of the prosthetic heart valve 12000-2 remains the same as the previous examples and the underlying components, including the stent 12002-2, cuff 12004-2 (including inner cuff 12006-2 and outer cuff 12050-2), heart valve assembly 12005-2, and pockets 12010-2, can include the same or similar features.

In one example, the radiopaque elements can be positioned adjacent a free edge of the leaflet. In the example of FIGS. 44-45, the heart valve assembly 12005-2 includes a first leaflet 12008-2A, a second leaflet 12008-2B, and a third leaflet 12008-2C. The radiopaque elements can be provided on each of the three leaflets, and in this example, adjacent the free edge of each leaflet. For example, as shown in FIG. 45, a radiopaque element 12020-2A is attached to first leaflet 12008-2A along a first edge portion 12088A, and a radiopaque element 12020-2B is attached to the opposite second edge portion 12088B of first leaflet 12008-2A. Second leaflet 12008-2B includes a radiopaque element 12020-2C adjacent its first edge portion 12088C, as well as another radiopaque element 12020-2D adjacent its opposite second edge portion 12088D. Third leaflet 12008-2C includes a radiopaque element 12020-2E adjacent its first edge portion 12088E and a radiopaque element 12020-2F adjacent its edge portion 12088F. Radiopaque elements 12020-2A-12020-2F may be positioned adjacent the free edges of the leaflets 12008-2A, 12008-2B, 12008-2C so that they are close to the commissures formed by adjacent leaflets. The portions of the leaflet free edges closest to the commissures move the least when the leaflets open and close. Therefore, positioning the radiopaque elements close to the commissures minimizes the impact the radiopaque elements may have on the operation of the leaflets.

The arrangement of the radiopaque elements adjacent a free edge of the leaflet can allow for one or more radiopaque elements on one leaflet to be positioned directly adjacent one or more radiopaque elements on an adjacent leaflet. Further, in examples where the radiopaque elements are positioned adjacent two outer edge portions of each leaflet in a valve assembly, the radiopaque elements on opposed edge portions of one leaflet will be directly adjacent radiopaque elements of the two directly adjacent leaflets. For example, as shown, a first radiopaque element 12020-2A on first leaflet 12008-2A is directly adjacent radiopaque element 12020-2C of second leaflet 12008-2B. Similarly, a second radiopaque element 12020-2B disposed on first leaflet 12008-2A is directly adjacent the radiopaque element 12020-2F disposed on the third leaflet 12008-2C. Radiopaque element 12020-2E on third leaflet 12008-2C is shown directly adjacent radiopaque element 12020-2D of second leaflet 12008-2B. The configuration of radiopaque elements on the free edges of the leaflets can help a surgeon identify the free edges of the leaflets, as well as where two adjacent leaflets meet. Moreover, the radiopaque elements can help a surgeon to better view the movements of the leaflets, including movements of the leaflets radially inward as they coapt with one another along their free edges. This enables the surgeon to determine whether the leaflets are coapting with one another properly.

In other examples, the radiopaque elements may be provided on any portion of a leaflet and in any configuration. For example, radiopaque elements may be positioned or disposed adjacent one or more edges of the leaflets, including two or more edges, or three or more edges depending on the type of valve and the structure of the leaflet. Radiopaque elements can additionally or alternatively be spaced away from the edges of the leaflet and can extend onto other portions of the leaflets, including the main body of the leaflet.

Figure 46:
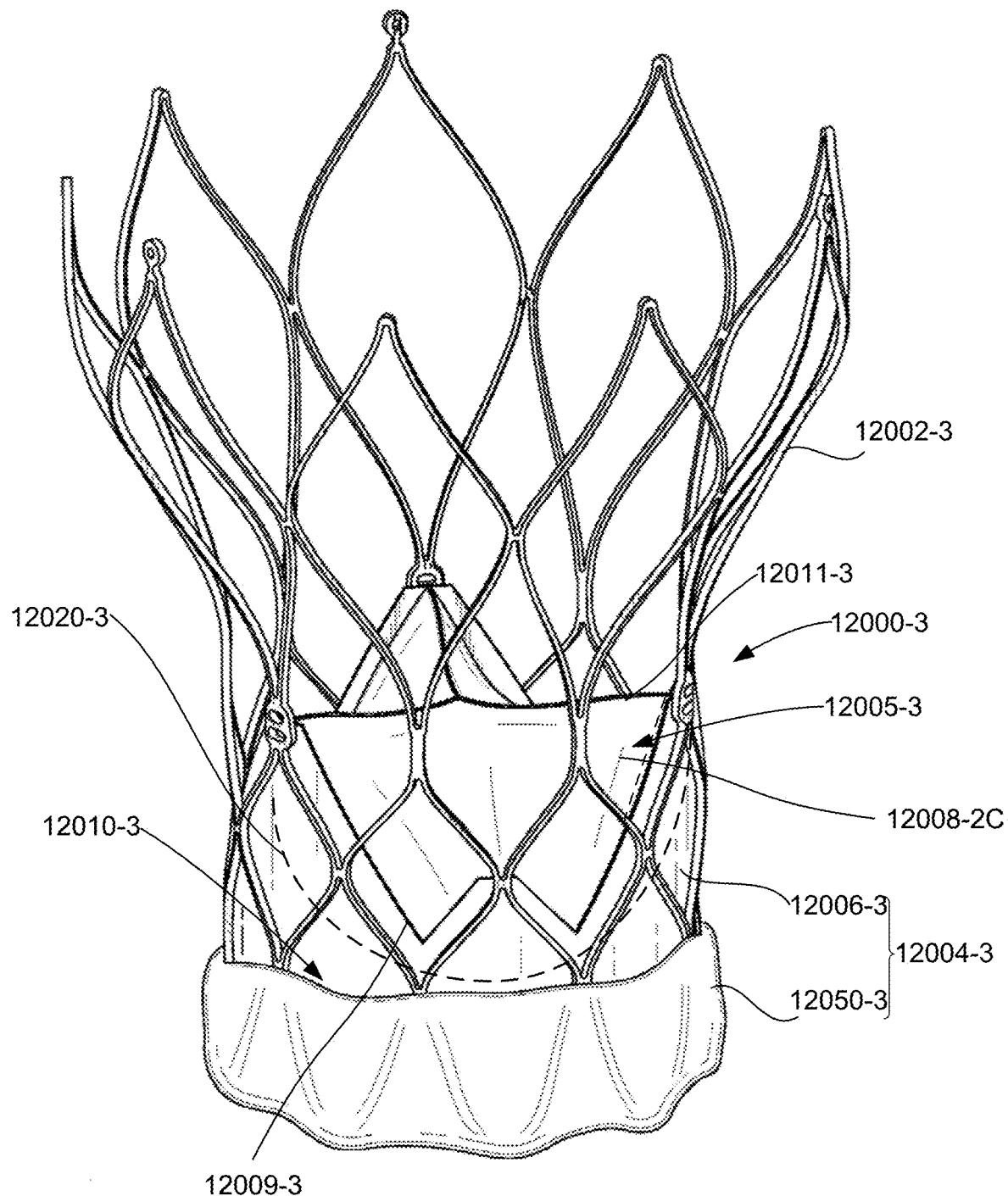
FIG. 46 is a perspective view of a prosthetic heart valve according to another embodiment of the disclosure.
Figure 47:
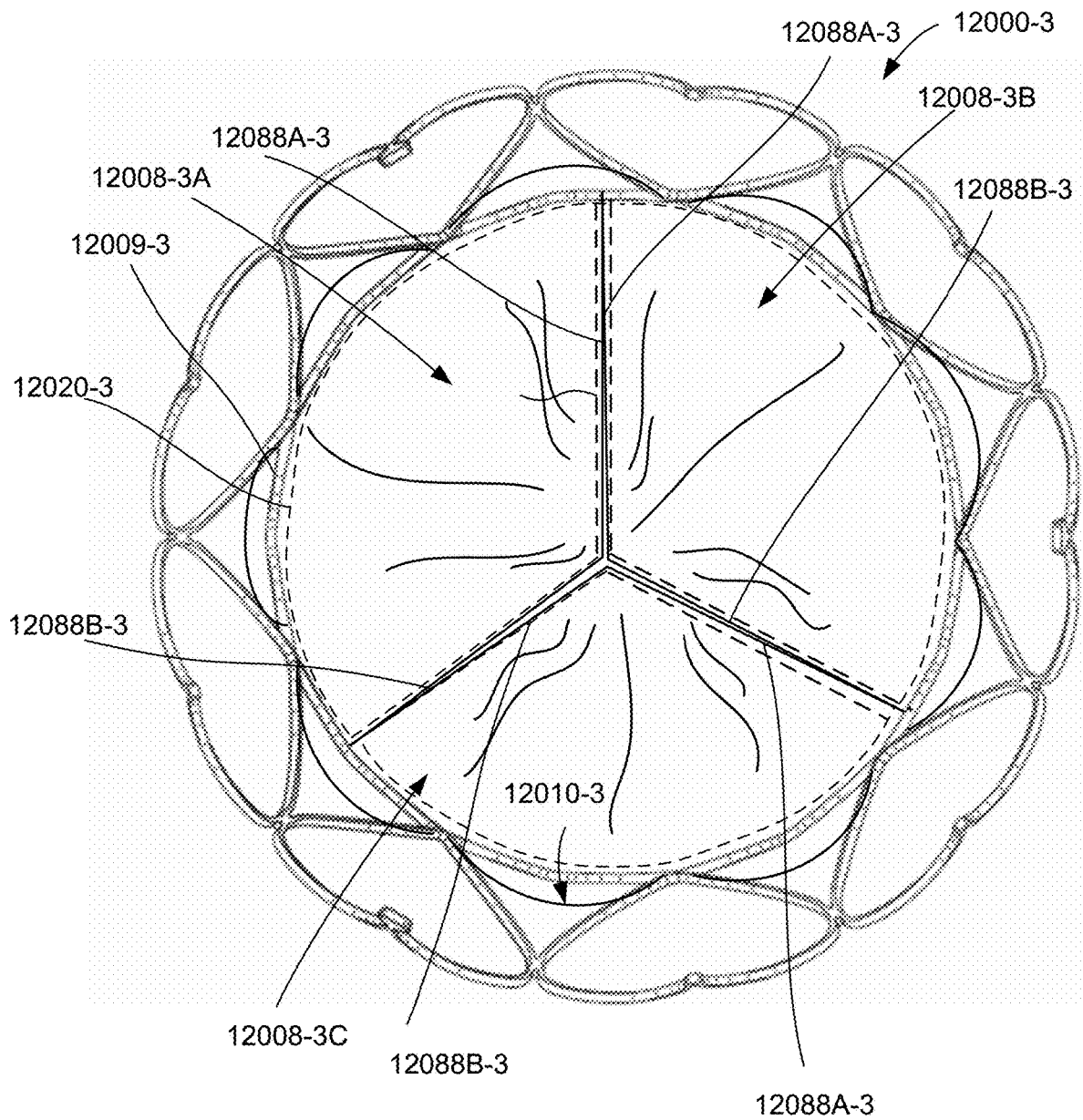
FIG. 47 is a schematic top view of the prosthetic heart valve of FIG. 46.

Radiopaque elements in the form of radiopaque sutures may alternatively or additionally be provided on one or more leaflets and on any portion of the one more leaflets. FIGS. 46-47 illustrate one example of radiopaque sutures provided on all of the leaflets within the heart valve assembly. As shown, a stent supported heart valve 12000-3 is substantially similar to the previous prosthetic heart valves disclosed herein, except for the inclusion of radiopaque sutures on the leaflets. Stent supported heart valve 12000-3 includes a heart valve assembly 12005-3, and a cuff 12004-3, which in this example includes both an inner cuff 12006-3 and an outer cuff 12050-3 with pockets 12010-3. The valve assembly 12005-3 further includes two or more leaflets, and in this example, three leaflets 12008-3A, 12008-3B, 12008-3C. Each of the three leaflets includes an edge 12020-3 attached to the cuff 12004-3, and particularly the inner cuff 12006-3, as well as two free edge portions 12088A-3, 12088B-3.

Radiopaque sutures 12020-3 may be provided along any of the respective edges of the three leaflets 12008-3A, 12008-3B, 12008-3C and, in fact, may be used to attach the leaflet to the cuff 12004-3. For example, a first leaflet 12008-3A includes a radiopaque suture along the edge 12009-3 of the leaflet closest to the stent 12002-3 (the "attached edge"), as well as along the free edge portions 12088A-3 and 12088B-3 of the leaflet. Placing radiopaque sutures along the entire free edge portions of the leaflets enables the surgeon to observe the coaptation of the leaflets and, in particular, to determine whether the leaflets are coapting properly with one another. Moreover, as the radiographic suture material may be lighter than the radiopaque rivets or swages, they are less likely to interfere with the proper opening and closing of the leaflets. In other examples, the radiopaque sutures 12020-3 may be provided along only the attached edge 12009-3, or alternatively along only the two free edge portions 12088A-3, 12088B-3, or alternatively along only one of the two free edge portions 12088A-3, 12088B-3. Similarly, the sutures can be provided on any portion of the leaflets and need not extend along an entire edge. In this example, each of the remaining leaflets 12008-3B, 12008-3C are shown as including radiopaque sutures along the same edges as the first leaflet 12008-3A, but in other examples the radiopaque sutures on either or both of the leaflets 12008-3B and 12008-3C may differ.

Additional radiopaque elements can be provided on the leaflets in combination with the radiopaque sutures. For example, the leaflets can further include one or more radiopaque elements attached to the leaflets, such as the radiopaque elements 12020-2A through 12020-2F shown in FIG. 45 that are positioned adjacent the edges of the leaflets.

The leaflet configuration of the valve assemblies 12005-2 and 12005-3 are examples of a valve configuration having three leaflets. In other examples, there may be only two leaflets, or more than three leaflets. The radiopaque elements may be attached or provided on one leaflet, two leaflets, or more than two leaflets, such as three or more leaflets, using any known means, including those disclosed herein. For example, each radiopaque element may be sutured to a leaflet or attached to a leaflet by an adhesive and the like, the radiopaque element may be the suture itself, or radiopaque suture may be used to attach another radiopaque element to the leaflet. Further, a radiopaque element of any type, shape, or size can be utilized, including those radiopaque elements disclosed herein.

In other examples, the radiopaque elements can be positioned on any portion of the one or more leaflets and in any configuration. The radiopaque elements can be positioned adjacent one or more edges of the leaflets, including free edge portions and the attached edge directly adjacent the stent. Radiopaque elements can additionally or alternatively be spaced away from the edges of the leaflet and can extend on other portions of the leaflets. Finally, the radiopaque elements as previously described herein can be provided on any one or more of the leaflets, in addition to one or more of the stent and the cuff, including either or both of the inner cuff and the outer cuff.

Combinations of Radiopaque Elements

The radiopaque elements may be positioned on any portion or portions of the prosthetic heart valve, including those arrangements disclosed herein. The radiopaque elements may also be positioned on multiple components of the prosthetic heart valve, including one or more of the cuff, the stent, and one or more leaflets. As previously discussed, radiopaque elements may be positioned or disposed on at least two or more components of a prosthetic heart valve in any one of the following combinations:

radiopaque elements disposed on the stent and the cuff (for example, a combination of radiopaque elements on any portion of the stent, including those examples shown and discussed in connection with FIGS. 23A-42, and radiopaque elements on the cuff, including those examples shown and discussed in connection with FIGS. 4-11B, 13-22D, and 43); or radiopaque elements disposed on the cuff and one or more leaflets (for example, a combination of radiopaque elements on the cuff, such as the examples shown and discussed in connection with FIGS. 4-11B, 13-22D, and 43, and radiopaque elements on one or more of the leaflets, such as the examples shown and discussed in connection with FIGS. 44-47); or radiopaque elements disposed on the stent and one or more leaflets (for example, a combination of radiopaque elements on any portion of the stent, including the examples shown and discussed in connection with FIGS. 23A-43, and radiopaque elements on one or more of the leaflets, including the examples shown and discussed in connection with FIGS. 44-47); or radiopaque elements disposed on all three of the cuff, the stent and one or more of the leaflets (including the examples shown and discussed in connection with any one of the preceding examples).

When the radiopaque elements are positioned on the cuff, as disclosed in the examples herein, the radiopaque element may be positioned on the inner cuff or the outer cuff or both, depending on the structure of the prosthetic heart valve. For example, in embodiments in which there is only a single cuff (as opposed to an inner cuff and an outer cuff), the radiopaque elements may be provided on an interior surface of the cuff, an exterior surface of the cuff or on both the interior and exterior surfaces of the cuff. In embodiments in which there is both an inner cuff and an outer cuff, the radiopaque elements may be positioned on the interior and/or exterior surfaces of the inner cuff, including being positioned within an interior of the pocket formed in the space between the inner cuff and the outer cuff. The radiopaque elements may additionally or alternatively be positioned on the outer cuff. For example, the radiopaque elements can be positioned on an exterior surface of the outer cuff and/or an interior surface of the outer cuff, including being positioned within an interior of the pocket formed in the space between the inner cuff and the outer cuff or in pockets formed on the exterior or interior surface of the outer cuff. In examples where the prosthetic heart valve includes both an inner cuff and an outer cuff, radiopaque elements may be provided on both the inner cuff and the outer cuff.

According to an aspect of the disclosure, a prosthetic heart valve for replacing a native valve includes a stent having an inflow end, an outflow end, a plurality of cells formed by cell struts, a collapsed condition and an expanded condition; a valve assembly disposed within the stent, the valve assembly including a plurality of leaflets, a first cuff having a proximal edge facing toward the inflow end of the stent and a distal edge facing toward the outflow end of the stent, the first cuff being annularly disposed adjacent the stent, and a second cuff having a proximal edge facing toward the inflow end of the stent and a distal edge facing toward the outflow end of the stent, the second cuff being annularly disposed about the stent radially outward of the first cuff and radially outward of the stent; and a radiopaque element disposed on the second cuff such that the radiopaque element is moveable relative to the stent; and/or the second cuff has an inner surface facing toward an abluminal surface of the stent and an outer surface facing away from the abluminal surface of the stent, and the radiopaque element is positioned on the outer surface of the second cuff; and/or the radiopaque element is moveable in at least two planes; and/or the radiopaque element is moveable in three planes; and/or the proximal edge of the first cuff is coupled to the proximal edge of the second cuff substantially continuously along a circumference of the inflow end of the stent; and/or the radiopaque element is positioned between cell struts forming a single cell of the plurality of the cells; and/or the radiopaque element is positioned at an inflow end of the prosthetic heart valve between cell struts of directly adjacent cells of the plurality of the cells; and/or the cuff includes a first portion and a second portion, the second portion having a proximal edge facing toward the inflow end of the stent and a distal edge facing toward the outflow end of the stent, the second portion being annularly disposed about the stent radially outward of the first portion of the cuff and radially outward of the stent, wherein pockets are formed in areas between the first portion of the cuff and the second portion of the cuff, and when the prosthetic heart valve is in the collapsed condition, the second cuff and the at least one pocket form a flap configured to be wrapped around the collapsed prosthetic heart valve; and/or the second cuff has an inner surface facing toward an abluminal surface of the stent and an outer surface facing away from the abluminal surface of the stent, and the radiopaque element is positioned on the inner surface of the second cuff, such that the radiopaque element is positioned between the second cuff and the first cuff; and/or the second cuff has an inner surface facing toward an abluminal surface of the stent and an outer surface facing away from the abluminal surface of the stent, the distal edge of the second cuff is attached to the stent at one or more locations around a circumference of the stent, and the radiopaque element includes a plurality of radiopaque elements attached to the outer surface of the second cuff; and/or the first and second cuffs are formed from one continuous piece of fabric material that wraps around the inflow end of the stent; and/or the prosthetic heart valve further includes at least one of an additional radiopaque element attached to the stent or an additional radiopaque element attached to the leaflets; and/or the radiopaque element comprises at least one of a suture or a metal marker.

According to another aspect of the disclosure, a prosthetic heart valve for replacing a native valve includes a stent extending in a longitudinal direction between an inflow end and an outflow end, the stent including a plurality of cells formed by cell struts and having a collapsed condition and an expanded condition; a valve assembly disposed within the stent, the valve assembly including a plurality of leaflets, and a cuff annularly disposed adjacent the stent; and a plurality of radiopaque elements attached to the cuff; and/or the plurality of radiopaque elements are attached to the cuff at circumferential positions, the circumferential positions being at least one of (1) between cell struts forming respective ones of the plurality of cells, or (2) between two adjacent cells of the plurality of cells; and/or at least one of the plurality of radiopaque elements is positioned between cell struts forming respective ones of the plurality of the cells; and/or at least one of the plurality of radiopaque elements is positioned at an inflow end of the prosthetic heart valve between cell struts of directly adjacent cells of the plurality of the cells; and/or the cuff is positioned adjacent a luminal surface of the stent; and/or at least a portion of the cuff faces an abluminal surface of the stent; and/or the cuff includes a first portion and a second portion, the second portion having a proximal edge facing toward the inflow end of the stent and a distal edge facing toward the outflow end of the stent, the second portion being annularly disposed about the stent radially outward of the first portion of the cuff and radially outward of the stent; and/or pockets are formed in areas between the first portion of the cuff and the second portion of the cuff; and/or the stent further includes a plurality of commissure attachment features, at least one of the plurality of radiopaque elements being aligned in the longitudinal direction with one of the plurality of commissure attachment features; and/or the plurality of radiopaque elements are attached to at least one of an outer surface of the second portion of the cuff an inner surface of the second portion of the cuff; and/or at least one of the plurality of radiopaque elements includes a radiopaque suture positioned on at least one of the cuff or the plurality of leaflets; and/or pockets are formed in areas between the first portion of the cuff and the second portion of the cuff, and a radiopaque suture extends along at least one of an edge of one of the plurality of leaflets or an edge of the pockets; and/or a portion of the first portion of the cuff and a portion of the second portion of the cuff are joined together to form a receiving pocket, and at least one of the plurality of radiopaque elements is disposed within the receiving pocket; and/or the portion of the first portion of the cuff and the portion of the second portion of the cuff are joined together by at least one of ultrasonic welding or suturing; and/or the inflow end of the stent includes tips extending circumferentially in a plane, and at least one of the plurality of radiopaque elements has an edge extending in the plane; and/or the inflow end of the stent includes tips extending circumferentially in a plane, and an edge of at least one of the plurality of radiopaque elements is positioned 3 mm away from the plane; and/or a top edge of at least one radiopaque element of the plurality of radiopaque elements is positioned 3 mm away from the plane; and/or a bottom edge of at least one radiopaque element of the plurality of radiopaque elements is positioned 3 mm away from the plane.

According to still another aspect of the disclosure, a prosthetic heart valve for replacing a native valve includes a stent having an inflow end, an outflow end, a plurality of cells formed by cell struts, a collapsed condition and an expanded condition; a valve assembly disposed within the stent, the valve assembly including a plurality of leaflets, a first cuff having a proximal edge facing toward the inflow end of the stent and a distal edge facing toward the outflow end of the stent, the first cuff being annularly disposed adjacent the stent, and a second cuff having a proximal edge facing toward the inflow end of the stent and a distal edge facing toward the outflow end of the stent, the second cuff being annularly disposed about the stent radially outward of the first cuff and radially outward of the stent, wherein the proximal edge of the first cuff is coupled to the proximal edge of the second cuff substantially continuously along a circumference of the inflow end of the stent so that a pocket is formed between the first cuff and the second cuff; and a radiopaque element disposed within the pocket; and/or the radiopaque element is attached to the first cuff or the second cuff; and/or the radiopaque element is attached to the first cuff and the second cuff; and/or the first cuff has an outer surface facing toward a luminal surface of the stent and an inner surface facing away from the luminal surface of the stent, the radiopaque element being positioned on the inner surface of the first cuff; and/or the radiopaque element is positioned between the second cuff and an abluminal surface of the stent.

According to another aspect of the disclosure, a prosthetic heart valve for replacing a native valve includes a stent having an inflow end, an outflow end, a plurality of cells formed by cell struts, a collapsed condition and an expanded condition; a valve assembly disposed within the stent, the valve assembly including a plurality of leaflets, and a cuff annularly disposed adjacent the stent; and a plurality of radiopaque elements disposed on at least one of the cuff, one of the plurality of leaflets, or the stent; and/or a first group of the radiopaque elements are attached to the valve assembly; and/or a second group of the radiopaque elements are attached to the leaflets; and/or a second group of the radiopaque elements are provided on the stent; and/or others of the radiopaque elements are provided on the cuff.

According to yet another aspect of the disclosure, a prosthetic heart valve for replacing a native valve includes a stent extending in a longitudinal direction between an inflow end and an outflow end, the stent including a plurality of cells formed by cell struts and a plurality of commissure attachment features and having a collapsed condition and an expanded condition; a valve assembly disposed within the stent, the valve assembly including a plurality of leaflets, and a cuff having a proximal edge facing toward the inflow end of the stent and a distal edge facing toward the outflow end of the stent, the cuff being annularly disposed adjacent the stent; and a radiopaque element positioned on the cuff in alignment with one of the plurality of commissure attachment features along an axis extending in the longitudinal direction through the one of the plurality of commissure attachment feature; and/or the cuff has an interior surface facing toward a longitudinal axis of the stent and an outer surface facing away from the longitudinal axis of the stent, and the radiopaque element is disposed on the interior surface of the cuff; and/or the cuff has an interior surface facing toward a longitudinal axis of the stent and an outer surface facing away from the longitudinal axis of the stent, and the radiopaque element is disposed on the outer surface of the cuff; and/or the cuff includes a first cuff and a second cuff, the second cuff being annularly disposed about the stent radially outward of the first cuff and radially outward of the stent, and the radiopaque element is positioned on the second cuff; and/or the second cuff has an interior surface facing toward an abluminal surface of the stent and an outer surface facing away from the abluminal surface of the stent, and the radiopaque element is disposed on the interior surface of the second cuff; and/or the second cuff has an interior surface facing toward an abluminal surface of the stent and an outer surface facing away from the abluminal surface of the stent, and the radiopaque element is disposed on the outer surface of the second cuff; and/or a pocket is formed in a space between the first cuff and the second cuff, and a portion of the first cuff and a portion of the second cuff are joined together to form a receiving pocket, and the radiopaque element is disposed within the receiving pocket; and/or the portion of the first cuff and the portion of the second cuff are joined together by at least one of ultrasonic welding or suturing; and/or the inflow end of the stent includes tips extending circumferentially in a plane, and the radiopaque element has an edge extending in the plane; and/or the inflow end of the stent includes tips extending circumferentially in a plane, and an edge of the radiopaque element is positioned 3 mm away from the plane; and/or a top edge of the radiopaque element is positioned 3 mm away from the plane; and/or a bottom edge of the radiopaque element is positioned 3 mm away from the plane.

According to another aspect of the disclosure, a prosthetic heart valve for replacing a native valve includes a stent, a valve assembly, and a radiopaque element. The stent has an inflow end, an outflow end, a plurality of cells formed by cell struts, a plurality of commissure attachment features, and a collapsed condition and an expanded condition. The valve assembly may be disposed within the stent and further include a plurality of leaflets, a first cuff and a second cuff. The first cuff may have a proximal edge relatively close to the inflow end of the stent and a distal edge relatively distant from the inflow end. The first cuff being may be annularly disposed adjacent the stent. The second cuff has a proximal edge relatively close to the inflow end of the stent and a distal edge relatively distant from the inflow end. The second cuff may be annularly disposed about the stent radially outward of the first cuff and radially outward of the stent, wherein the proximal edge of the first cuff is coupled to the proximal edge of the second cuff substantially continuously along a circumference of the inflow end of the stent so that a pocket is formed between the first cuff and the second cuff. The radiopaque element is disposed within the pocket and aligned in a longitudinal direction of the stent with at least one of the plurality of commissure attachment features; and/or the radiopaque element is sutured to the first cuff; and/or
the radiopaque element is sutured to the second cuff; and/or
the radiopaque element is sutured to the first cuff and the second cuff; and/or
sutures extend through the first cuff and the second cuff adjacent a peripheral edge of the radiopaque element; and/or
the sutures are arranged in a suture pattern forming a shape of a cross; and/or
the radiopaque element includes an opening and the sutures extend through the opening; and/or
the sutures extend around a peripheral edge of the radiopaque element; and/or
the radiopaque element has a circular body with an opening extending through a thickness of the circular body; and/or
the inflow end of the stent includes a plurality of tips defining a plane, and an edge or lowermost point of the radiopaque element is positioned 3 mm away from the plane; and/or
the plurality of commissure attachment features comprises three commissure attachment features, the radiopaque element comprises three radiopaque elements, and each of the three radiopaque elements is aligned in a longitudinal direction of the stent with a corresponding one of the three commissure attachment features; and/or the inflow end of the stent includes a plurality of tips defining a plane, and an edge of each of the three radiopaque elements is positioned 3 mm away from the plane; and/or the inflow end of the stent includes a plurality of tips defining a plane, and an edge of the radiopaque element is positioned 3 mm away from the plane; and/or the radiopaque element comprises a plurality of radiopaque elements, and each one of the plurality of radiopaque elements is aligned in a longitudinal direction of the stent with a corresponding one of the plurality of commissure attachment features; and/or each of the plurality of radiopaque elements is sutured to the first cuff and/or the second cuff, the inflow end of the stent includes a plurality of tips defining a plane, and an edge of each of the plurality of radiopaque elements are circumferentially aligned with one another at a same distance away from the plane; and/or the radiopaque element comprises a plurality of radiopaque elements, each of the plurality of radiopaque elements is aligned in a longitudinal direction of the stent with a corresponding one of the plurality of commissure attachment features, each of the plurality of radiopaque elements is sutured to the first cuff and/or the second cuff, the inflow end of the stent includes a plurality of tips defining a plane, an edge of each of the plurality of radiopaque elements are circumferentially aligned with one another at a same distance away from the plane; and/or the sutures are comprised of radiopaque material; and/or
additional sutures comprised of a radiopaque material are provided on the prosthetic heart valve; and/or
the additional sutures comprised of the radiopaque material are provided on the leaflets.

According to another aspect of the disclosure, a prosthetic heart valve for replacing a native valve includes a stent, a valve assembly, and a plurality of radiopaque elements. The stent extends in a longitudinal direction of the stent between an inflow end and an outflow end. The stent has a plurality of cells formed by cell struts, a plurality of commissure attachment features, and a collapsed condition and an expanded condition. The valve assembly may be disposed within the stent and include a plurality of leaflets; and a cuff annularly disposed adjacent the stent. The plurality of radiopaque elements may be attached to the cuff, and each of the plurality of radiopaque elements may be aligned in a longitudinal direction of the stent with a corresponding one of the plurality of commissure attachment features. The inflow end of the stent includes a plurality of tips defining a plane, and edges of at least two of the plurality of radiopaque elements are positioned a same distance away from the plane; and/or the plurality of radiopaque elements are disposed in an area between adjacent cells of the plurality of cells or between cells that are vertically adjacent one another; and/or in the edges of the at least two of the plurality of radiopaque elements are positioned 3 mm away from the plane; and/or the plurality of radiopaque elements are three radiopaque elements comprised of tantalum; and/or the cuff comprises an outer cuff and an inner cuff, and wherein the plurality of radiopaque elements are sutured to the cuff with a suture pattern in the shape of a cross; and/or the sutures are comprised of radiopaque material; and/or additional sutures comprised of a radiopaque material are provided on the prosthetic heart valve; and/or the additional sutures comprised of the radiopaque material are provided on the leaflets.

According to another aspect of the disclosure, a prosthetic heart valve includes a stent, a valve assembly, and a plurality of radiopaque elements. The stent has an inflow end, an outflow end, a plurality of cells formed by cell struts, a plurality of commissure attachment features, and a collapsed condition and an expanded condition, wherein the inflow end of the stent includes a plurality of tips defining a plane. The valve assembly is disposed within the stent and includes a plurality of leaflets and first and second cuffs. The first cuff has a proximal edge relatively close to the inflow end of the stent and a distal edge relatively distant from the inflow end. The first cuff is annularly disposed adjacent the stent. The second cuff has a proximal edge relatively close to the inflow end of the stent and a distal edge relatively distant from the inflow end. The second cuff is annularly disposed about the stent radially outward of the first cuff and radially outward of the stent. The proximal edge of the first cuff is coupled to the proximal edge of the second cuff substantially continuously along a circumference of the inflow end of the stent so that a pocket is formed between the first cuff and the second cuff. The plurality of radiopaque elements are sutured to the first cuff and/or the second cuff and each aligned in a longitudinal direction of the stent with a corresponding one of the plurality of commissure attachment features. An edge of each of the plurality of radiopaque elements is circumferentially aligned with one another at a same distance away from the plane; and/or the radiopaque element is sutured to the first cuff; and/or the plurality of radiopaque elements are sutured to the second cuff; and/or the plurality of radiopaque elements are sutured to the first cuff and the second cuff; and/or sutures extend through the first cuff and the second cuff adjacent a peripheral edge of the plurality of radiopaque elements; and/or the sutures are arranged in a suture pattern forming a shape of a cross; and/or the plurality of radiopaque elements includes an opening and the sutures extend through the opening; and/or the sutures extend around a peripheral edge of the plurality of radiopaque elements; and/or the radiopaque elements have a circular body with an opening extending through a thickness of the circular body; and/or the inflow end of the stent includes a plurality of tips defining a plane, and an edge or lowermost point of each of the plurality of radiopaque elements is positioned 3 mm away from the plane; and/or the plurality of commissure attachment features comprises three commissure attachment features, the plurality of radiopaque elements comprises three radiopaque elements, and each of the three radiopaque elements is aligned in a longitudinal direction of the stent with a corresponding one of the three commissure attachment features; and/or the inflow end of the stent includes a plurality of tips defining a plane, and an edge of each of the three radiopaque elements is positioned 3 mm away from the plane; and/or the inflow end of the stent includes a plurality of tips defining a plane, and an edge of each of the plurality of radiopaque elements is positioned 3 mm away from the plane; and/or each one of the plurality of radiopaque elements is aligned in a longitudinal direction of the stent with a corresponding one of the plurality of commissure attachment features; and/or the sutures are comprised of radiopaque material; and/or additional sutures comprised of a radiopaque material are provided on the prosthetic heart valve; and/or the additional sutures comprised of the radiopaque material are provided on the leaflets.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims. For example, features of one embodiment described above may be combined with features of other embodiments described above.

The invention claimed is:

1. A prosthetic heart valve for replacing a native valve, comprising:
    a stent having an inflow end, an outflow end, a plurality of cells formed by cell struts, a plurality of commissure attachment features, and a collapsed condition and an expanded condition, each of the commissure attachment features including an eyelet for attaching leaflets to the stent;
    a valve assembly disposed within the stent, the valve assembly comprising:
        a plurality of leaflets;
        a first cuff having a proximal edge relatively close to the inflow end of the stent and a distal edge relatively distant from the inflow end, the first cuff being annularly disposed adjacent the stent; and
        a second cuff having a proximal edge relatively close to the inflow end of the stent and a distal edge relatively distant from the inflow end, the second cuff being annularly disposed about the stent radially outward of the first cuff and radially outward of the stent, wherein the proximal edge of the first cuff is coupled to the proximal edge of the second cuff substantially continuously along a circumference of the inflow end of the stent so that a pocket is formed between the first cuff and the second cuff; and
    a radiopaque element disposed within the pocket and connected by sutures only to the first cuff or only to the second cuff and aligned in a longitudinal direction of the stent with at least one of the plurality of commissure attachment features.

2. The prosthetic heart valve of claim 1, wherein the radiopaque element is sutured only to the first cuff.

3. The prosthetic heart valve of claim 1, wherein the radiopaque element is sutured only to the second cuff.

4. The prosthetic heart valve of claim 1, wherein the sutures are arranged in a suture pattern forming a shape of a cross.

5. The prosthetic heart valve of claim 4, wherein the radiopaque element includes an opening and the sutures extend through the opening.

6. The prosthetic heart valve of claim 1, wherein the sutures extend around a peripheral edge of the radiopaque element.

7. The prosthetic heart valve of claim 6, wherein the radiopaque element has a circular body with an opening extending through a thickness of the circular body.

8. The prosthetic heart valve of claim 1, wherein the inflow end of the stent includes a plurality of tips defining a plane, and an edge or lowermost point of the radiopaque element is positioned 3 mm away from the plane.

9. The prosthetic heart valve of claim 8, wherein the plurality of commissure attachment features comprises three commissure attachment features, the radiopaque element comprises three radiopaque elements, and each of the three radiopaque elements is aligned in a longitudinal direction of the stent with a corresponding one of the three commissure attachment features.

10. The prosthetic heart valve of claim 9, wherein the inflow end of the stent includes a plurality of tips defining a plane, and an edge of each of the three radiopaque elements is positioned 3 mm away from the plane.

11. The prosthetic heart valve of claim 1, wherein the inflow end of the stent includes a plurality of tips defining a plane, and an edge of the radiopaque element is positioned 3 mm away from the plane.

12. The prosthetic heart valve of claim 1, wherein the radiopaque element comprises a plurality of radiopaque elements, and each one of the plurality of radiopaque elements is aligned in a longitudinal direction of the stent with a corresponding one of the plurality of commissure attachment features.

13. A prosthetic heart valve for replacing a native valve, comprising:
a stent extending in a longitudinal direction between an inflow end and an outflow end, the stent having a plurality of cells formed by cell struts, a plurality of commissure attachment features, a collapsed condition and an expanded condition;
a valve assembly disposed within the stent, the valve assembly comprising:
a plurality of leaflets; and
a cuff annularly disposed adjacent the stent; and
a plurality of radiopaque elements attached to the cuff in areas between adjacent cells of the plurality of cells and not within any of the plurality of cells, each of the plurality of radiopaque elements being aligned in a longitudinal direction of the stent with a corresponding one of the plurality of commissure attachment features,
wherein the inflow end of the stent includes a plurality of tips defining a plane, and edges of at least two of the plurality of radiopaque elements are positioned a same distance away from the plane.

14. The prosthetic heart valve of claim 13, wherein the edges of the at least two of the plurality of radiopaque elements are positioned 3 mm away from the plane.

15. The prosthetic heart valve of claim 14, wherein the plurality of radiopaque elements are three radiopaque elements comprised of tantalum.

16. The prosthetic heart valve of claim 13, wherein the cuff comprises an outer cuff and an inner cuff, and wherein the plurality of radiopaque elements are sutured to the cuff with a suture pattern in a shape of a cross.

17. A prosthetic heart valve, comprising:
a stent having an inflow end, an outflow end, a plurality of cells formed by cell struts, a plurality of commissure attachment features, a collapsed condition and an expanded condition, wherein the inflow end of the stent includes a plurality of tips defining a plane and each of the commissure attachment features includes an eyelet for attaching leaflets to the stent;
a valve assembly disposed within the stent, the valve assembly comprising:
a plurality of leaflets;
a first cuff having a proximal edge relatively close to the inflow end of the stent and a distal edge relatively distant from the inflow end, the first cuff being annularly disposed adjacent the stent; and
a second cuff having a proximal edge relatively close to the inflow end of the stent and a distal edge relatively distant from the inflow end, the second cuff being annularly disposed about the stent radially outward of the first cuff and radially outward of the stent, wherein the proximal edge of the first cuff is coupled to the proximal edge of the second cuff substantially continuously along a circumference of the inflow end of the stent so that a pocket is formed between the first cuff and the second cuff; and
a plurality of radiopaque elements, each radiopaque element being sutured only to the first cuff or only to the second cuff and ones of the radiopaque elements being aligned in a longitudinal direction of the stent with a corresponding one of the plurality of commissure attachment features, wherein edges of the plurality of radiopaque elements are circumferentially aligned with one another at a same distance away from the plane.

* * * * *